United States Patent

Gold et al.

[11] Patent Number: 5,998,142
[45] Date of Patent: *Dec. 7, 1999

[54] SYSTEMATIC EVOLUTION OF LIGANDS BY EXPONENTIAL ENRICHMENT: CHEMI-SELEX

[75] Inventors: Larry Gold; Bruce Eaton; Drew Smith; Matthew Wecker, all of Boulder, Colo.; Kirk Jensen, New York, N.Y.

[73] Assignee: NeXstar Pharmaceuticals, Inc., Boulder, Colo.

[*] Notice: This patent is subject to a terminal disclaimer.

[21] Appl. No.: 08/894,578

[22] Filed: Aug. 21, 1997

Related U.S. Application Data

[63] Continuation-in-part of application No. 08/400,440, Mar. 8, 1995, Pat. No. 5,705,337, application No. 08/117,991, Sep. 8, 1993, abandoned, application No. 08/123,935, Sep. 17, 1993, abandoned, application No. 08/199,507, Feb. 22, 1994, Pat. No. 5,472,841, application No. 08/234,997, Apr. 28, 1994, Pat. No. 5,683,867, and application No. 08/309,245, Sep. 20, 1994, Pat. No. 5,723,289, said application No. 08/400,440, is a continuation-in-part of application No. 07/714,131, Jun. 10, 1991, Pat. No. 5,475,096, which is a continuation-in-part of application No. 07/536,428, Jun. 11, 1990, abandoned.

[51] Int. Cl.⁶ .............................. C12Q 1/68; C12P 19/34; C07H 21/04; C07H 21/02
[52] U.S. Cl. ........................ 435/6; 435/91.2; 536/23.1; 536/24.3; 536/25.4; 935/77; 935/78
[58] Field of Search ................ 435/6, 91.2; 536/23.1, 536/25.4, 24.3; 935/77, 78

[56] References Cited

U.S. PATENT DOCUMENTS

| 4,959,309 | 9/1990 | Dattagupta et al. | 435/6 |
| 5,270,163 | 12/1993 | Gold et al. | 435/6 |
| 5,763,177 | 6/1998 | Gold et al. | 435/6 |
| 5,763,595 | 6/1998 | Gold et al. | 536/22.1 |

FOREIGN PATENT DOCUMENTS

| 2 183 661 | 6/1987 | United Kingdom . |
| WO89/06694 | 7/1989 | WIPO . |
| WO91/14696 | 10/1991 | WIPO . |
| WO91/19813 | 12/1991 | WIPO . |
| WO92/14843 | 9/1992 | WIPO . |
| WO94/01448 | 1/1994 | WIPO . |

*Primary Examiner*—Stephanie Ztonmer
*Attorney, Agent, or Firm*—Swanson & Bratschun LLC

[57] ABSTRACT

This application provides methods for identifying nucleic acid ligands capable of covalently interacting with targets of interest. The nucleic acids can be associated with various functional units. The method also allows for the identification of nucleic acids that have facilitating activities as measured by their ability to facilitate formation of a covalent bond between the nucleic acid, including its associated functional unit, and its target.

5 Claims, No Drawings

SYSTEMATIC EVOLUTION OF LIGANDS BY EXPONENTIAL ENRICHMENT: CHEMI-SELEX

This application is a Section 371 filing of PCT/US96/03097, filed Mar. 5, 1996, which is a Continuation-in-Part of U.S. patent application Ser. No. 08/400,440, filed Mar. 8, 1995, entitled "Systematic Evolution of Ligands by Exponential Enrichment: Chemi-SELEX", now issued as U.S. Pat. No. 5,705,337, which is a Continuation-in-Part of U.S. patent application Ser. No. 07/714,131, filed Jun. 10, 1991, entitled "Nucleic Acid Ligands", now issued as U.S. Pat. No. 5,475,096, which was filed as a Continuation-in-Part of U.S. patent application Ser. No. 07/536,428, filed Jun. 11, 1990, entitled "Systematic Evolution of Ligands by Exponential Enrichment", now abandoned. This application is also a Continuation-in-Part of U.S. patent application Ser. No. 08/117,991, filed Sep. 8, 1993, entitled "High Affinity Nucleic Acid Ligands Containing Modified Nucleotides", now abandoned; U.S. patent application Ser. No. 08/123,935, filed Sep. 17, 1993, entitled "Photoselection of Nucleic Acid Ligands", now abandoned; U.S. patent application Ser. No. 08/199,507, filed Feb. 22, 1994, entitled "Nucleic Acid Inhibitors of Human Neutrophil Elastase", now issued as U.S. Pat. No. 5,472,841; U.S. patent application Ser. No. 08/234,997, filed Apr. 28, 1994, entitled "Systematic Evolution of Ligands by Exponential Enrichment: Blended SELEX", now issued as U.S. Pat. No. 5,683,867; and U.S. patent application Ser. No. 08/309,245, filed Sep. 20, 1994, entitled "Parallel SELEX", now issued as U.S. Pat. No. 5,723,289.

FIELD OF THE INVENTION

Described herein is a method for generating nucleic acid ligands having various desirable properties. The desirable properties include, but are not limited to, the ability to attach a nucleic acid to its target covalently; the ability to attach a nucleic acid to its target non-covalently with a very high specificity; the ability to facilitate an interaction between a functional unit associated with the nucleic acid and a desirable target; and the ability to subtractively partition a nucleic acid having desirable properties from the remainder of a candidate mixture.

The method of this invention takes advantage of the method for identifying nucleic acid ligands referred to as the SELEX combinatorial chemistry process. The term SELEX is an acronym for Systematic Evolution of Ligands by EXponential enrichment. The method of identifying nucleic acids, preferably associated with other functional units, which have the facilitative activity described herein is termed the Chemi-SELEX process. The nucleic acid ligands of the present invention consist of at least one nucleic acid region and not necessarily, but preferably at least one functional unit. The nucleic acid region(s) of the nucleic acid ligand serve in whole or in part as ligands to a given target. Conversely, the nucleic acid region may serve to facilitate a covalent interaction between the attached functional unit and a given target. The functional unit(s) can be designed to serve in a large variety of functions. For example, the functional unit may independently or in combination with the nucleic acid unit have specific affinity for the target, and in some cases may be a ligand to a different site of interaction with the target than the nucleic acid ligand. Functional unit(s) may be added for a variety of purposes which include, but are not limited to, those which covalently react and couple the ligand to the target molecule, catalytic groups may be added to aid in the selection of protease or nuclease activity, and reporter molecules such as biotin or fluorescein may be added for use as diagnostic reagents. Examples of functional units that may be coupled to nucleic acids include chemically-reactive groups, photoreactive groups, active site directed compounds, lipids, biotin, proteins, peptides and fluorescent compounds. Particularly preferred functional units are chemically-reactive groups, including photoreactive groups.

BACKGROUND OF THE INVENTION.

A method for the in vitro evolution of nucleic acid molecules with highly specific binding to target molecules has been developed. This method, Systematic Evolution of Ligands by EXponential enrichment, termed the SELEX combinatorial chemistry process, is described in U.S. patent application Ser. No. 07/536,428, filed Jun. 11, 1990, entitled "Systematic Evolution of Ligands by Exponential Enrichment", now abandoned, U.S. patent application Ser. No. 07/714,131, filed Jun. 10, 1991, entitled "Nucleic Acid Ligands", now U.S. Pat. No. 5,475,096, U.S. patent application Ser. No. 07/931,473, filed Aug. 17, 1992, entitled "Nucleic Acid Ligands", now U.S. Pat. No. 5,270,163 (see also WO91/19813), each of which is herein specifically incorporated by reference. Each of these applications, collectively referred to herein as the SELEX Patent Applications, describes a fundamentally novel method for making a nucleic acid ligand to any desired target molecule. The SELEX process provides a class of products which are referred to as nucleic acid ligands, such ligands having a unique sequence, and which have the property of binding specifically to a desired target compound or molecule. Each SELEX-identified nucleic acid ligand is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size can serve as targets.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX method demonstrates that nucleic acids as chemical compounds can form a wide array of shapes, sizes and configurations, and are capable of a far broader repertoire of binding and other functions than those displayed by nucleic acids in biological systems.

The dogma for many years was that nucleic acids had primarily an informational role. Through the application of the SELEX process it has become clear to the present inventors that nucleic acids have three dimensional structural diversity not unlike proteins. As such, the present inventors have recognized that the SELEX process or SELEX-like processes could be used to identify nucleic acids which can facilitate any chosen reaction in a manner similar to that in which nucleic acid ligands can be identified for any given target. In theory, within a candidate mixture of approximately $10^{13}$ to $10^{18}$ nucleic acids, the present inventors postulate that at least one nucleic acid exists with the appropriate shape to facilitate a broad variety of physical and chemical interactions.

Studies to date have identified only a few nucleic acids which have only a narrow subset of facilitating capabilities. A few RNA catalysts are known (Cech,1987. *Science* 236:1532–1539 and McCorkle and Altman 1987. *J: of Chemical Education* 64:221–226). These naturally occurring RNA enzymes (ribozymes) have to date only been shown to act on oligonucleotide substrates (see U.S. Pat. Nos. 4,987,071; 5,354,855; 5,180,818; 5,116,742; 5,093,246; 5,037,746 and European Patent 291 533). Further, these molecules perform over a narrow range of chemical possibilities, which are thus far related largely to phosphodiester bond condensation/hydrolysis, with the exception of the possible involvement of RNA in protein biosynthesis. Despite intense recent investigation to identify RNA or DNA catalysts, few successes have been identified. Phosphodiester cleavage (Beaudry and Joyce, 1992. *Science* 257:635), hydrolysis of aminoacyl esters (Piccirilli et al.,1992. *Science* 256:1420–1424), self-cleavage (Pan et al., 1992. *Biochemistry* 31:3887), ligation of an oligonucleotide with a 3' OH to the 5' triphosphate end of the catalyst (Bartel et al.,1993. *Science* 261:1411–1418), biphenyl isomerase activity (Prudent et al.,1994. *Science* 264:1924–1927), and polynucleotide kinase activity (Lorsch et al.,1994. *Nature* 371:31∓36) have been observed. The nucleic acid catalysts known to date have certain shortcomings associated with their effectiveness in bond forming/breaking reactions. Among the drawbacks are that they act slowly relative to protein enzymes, and as described above, they perform over a somewhat narrow range of chemical possibilities.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," now abandoned (See also, U.S. Pat. No. 5,707,796) describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned (See also, U.S. Pat. No. 5,763,177) describes a SELEX based method for selecting nucleic acid ligands containing photoreactive groups capable of binding and/or photo-crosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," now abandoned (See also, U.S. Pat. No. 5,580,737) describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX," now abandoned (See also, U.S. Pat. No. 5,567,588) describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," now abandoned (See also, U.S. Pat. No. 5,660,985) that describes oligonucleotides containing nucleotide derivatives chemically modified at the 5-and 2'-positions of pyrimidines. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2'-Modified Nucleosides by Intramolecular Nucleophilic Displacement", now issued as U.S. Pat. No. 5,756,703, describes oligonucleotides containing various 2'-modified nucleosides.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" now issued as U.S. Pat. No. 5,637,459 and U.S. patent application Ser. No. 08/234,997, filed Apr. 28, 1994, entitled "Systematic Evolution of Ligands by Exponential Enrichment: Blended SELEX," now issued as U.S. Pat. No. 5,683,867, respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

BRIEF SUMMARY OF THE INVENTION

The present invention describes the use of a SELEX-like process where the enrichment and identification of nucleic acids is based on the ability of the nucleic acid to facilitate a chemical reaction. Nucleic acids having facilitative properties are capable of mediating chemical reactions such as bond formation. In the primary embodiment of this invention, the reaction being facilitated is between the nucleic acid and a target. In this embodiment, the nucleic acid candidate mixture preferably is made up of nucleic acids that are associated with one or more functional units. In this aspect, the invention requires that the facilitative nucleic acids direct an interaction between the nucleic acid or its attached functional unit and a given target. When the method of the present invention is used to identify nucleic acid sequences that facilitate the reaction between a functional group associated with the nucleic acid and the target, the process is referred to as Chemi-SELEX.

In one embodiment of the invention, a method is provided for identifying nucleic acid ligands of a target molecule from a candidate mixture of nucleic acids, said method comprising: preparing a candidate mixture of nucleic acids; contacting said candidate mixture with said target molecule, wherein nucleic acid ligands that bind covalently with said target may be partitioned from the remainder of the candidate mixture; partitioning the nucleic acids that bind covalently with said target from the remainder of the candidate mixture; and amplifying the nucleic acids that bind covalently with said target, whereby the nucleic acid ligands that bind covalently with the target molecule may be identified. The invention also provides nucleic acid ligands that bind covalently with a target molecule produced by the method of the invention.

In another embodiment, the invention provides a method for identifying nucleic acid ligands having a facilitating activity from a candidate mixture of nucleic acids, said method comprising: contacting the candidate mixture with a target, wherein nucleic acids having a facilitating activity, as indicated by a covalent bond being formed between said target and said nucleic acid, relative to the candidate mixture may be partitioned from the remainder of the candidate mixture; partitioning the nucleic acids having a facilitating activity from the remainder of the candidate mixture; and amplifying the nucleic acids having a facilitating activity, whereby the nucleic acids having a facilitating activity may be identified.

The functional unit can be added to provide the nucleic acid region with additional functional capabilities. The functional capabilities imparted by the functional unit include additional binding affinity between the nucleic acid ligand and the target in the form of a covalent interaction or a non-covalent interaction, ability to crosslink the functional unit with the target in a covalent or non-covalent manner, and ability to interact with the target in a reversible or irreversible manner.

The present invention provides a method for identifying nucleic acids having facilitative abilities. The ability of the nucleic acids to facilitate a chemical reaction being considered may arise from one or a combination of factors. In some instances, the nucleic acid may simply be selected based on its ability to bind the target species thereby allowing the functional unit spatial access to the target. In other instances, the nucleic acid may be selected due to its ability to present the functional unit in a particular orientation and environment which allows the functional unit to either react with the target or to have its facilitative effect of the target.

The present invention encompasses nucleic acid ligands coupled to a non-nucleic acid functional unit. The nucleic acid and functional unit interact with the target in a synergistic manner.

In another embodiment, this invention provides a method for the subtractive separation of desirable ligands from less desirable ligands. This embodiment takes advantage of the strong interaction between the nucleic acid and/or it associated functional unit and the target to partition the covalently attached or strongly non-covalently attached nucleic acid-target complexes from free nucleic acids.

In another embodiment, subtractive separation is further exploited to automate the entire selection process. This embodiment makes the selection process much less labor intensive and provides the methods and apparatus to accomplish said automation.

DETAILED DESCRIPTION OF THE INVENTION

The present invention provides a method for identifying nucleic acids which have the ability to facilitate a chemical reaction. In the most preferred embodiment, the nucleic acids comprise a nucleic acid region and a functional unit. However, unmodified nucleic acids are within the scope of the present invention. The desirable properties that the nucleic acids derived by this method display are numerous and include, but are not limited to, the ability to facilitate a covalent interaction or strong non-covalent interaction between the nucleic acid or its associated functional unit and a given target, the ability to enhance the interaction between a nucleic acid ligand and a given target, and the ability to subtractively partition the nucleic acid ligand from the remainder of the nucleic acid candidate mixture.

The methods herein described are based on the SELEX method. The SELEX process is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, now issued as U.S. Pat. No. 5,475,096, U.S. patent application Ser. No. 07/931,473, filed Aug. 17, 1992, entitled Nucleic Acid Ligands, now U.S. Pat. No. 5,270,163 (see also WO91/19813). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for certain interaction, preferably binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets wherein the protein is and is not a nucleic acid binding protein.

The basic SELEX method has been modified to achieve specific objectives. U.S. patent application Ser. No. 08/123,935, filed Sep. 17, 1993, entitled "Photoselection of Nucleic Acid Ligands" now abandoned (See also, U.S. Pat. No. 5,763,177), describes a SELEX-based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine",now abandoned (See also, U.S. Pat. No. 5,580,737), describes a method for identifying highly specific nucleic acid ligands able to discriminate between closely related molecules, termed "Counter-SELEX." U.S. patent application Ser. No. 08/143,564, filed Oct. 25, 1993, entitled "Systematic Evolution of Ligands by EXponential Enrichment: Solution SELEX", now abandoned (See also, U.S. Pat. No. 5,567,588), describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or delivery. Examples of such modifications include chemical substitutions at the ribose and/or phosphate and/or base positions. Specific SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," now abandoned (See also, U.S. Pat. No. 5,660,985) that describes oligonucleotides containing nucleotide derivatives chemically modified at the 5-and 2'-positions of pyrimidines, as well as specific RNA ligands to thrombin containing 2'-amino modifications. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). The above-mentioned SELEX improvement patent applications are herein incorporated by reference.

An example of Chemi-SELEX was described in co-pending WO95/08003, filed Sep. 19, 1994 which is a CIP of U.S. patent application Ser. No. 08/123,935, filed Sep. 17, 1993, entitled "Photoselection of Nucleic Acid Ligands" supra. In that application, specifically incorporated by reference, certain nucleic acid sequences that contained 5-iodouracil residues were identified that covalently bind to HIV-1 Rev protein. In that example of Chemi-SELEX, the functional group associated with all of the members of the candidate mixture was 5-iodouracil.

In an additional embodiment of the present invention, the nucleic acid sequences identified will be selected on the basis of the ability of the functional unit associated with the nucleic acids to facilitate a reaction to the target. Such a reaction might be a bond cleavage or the reaction of the target with another chemical species. An example of the embodiment of the present invention is described in co-pending and commonly assigned patent application U.S. patent application Ser. No. 08/254,997, filed Apr. 28, 1994, entitled "Systematic Evolution of Ligands by Exponential Enrichment: Blended SELEX" now issued as U.S. Pat. No. 5,683,867. In that application, specifically incorporated by reference, a nucleic acid ligand to human neutrophil elastase was identified wherein a functional unit was associated with the nucleic acid ligand. In this instance, the functional unit was a valyl phosphonate that bound covalently to the elastase target.

Another example of this embodiment is described in co-pending and commonly assigned patent application U.S. patent application Ser. No. 08/309,245, filed Sep. 20, 1994, entitled "Parallel SELEX" now issued as U.S. Pat. No. 5,723,289. In that application, specifically incorporated herein by reference, the covalent reaction between two reactants to form a product is specifically facilitated by a member of a pool of nucleic acids attached to one of the reactants.

The present invention includes the Chemi-SELEX method for generating nucleic acid ligands to specific target molecules with various desirable properties. The desirable properties associated with the nucleic acid ligands of the present invention include, but are not limited to, high affinity binding, specific binding, high potency (even when associated with a moderate to modest affinity), high specificity inhibition or potentiation, etc. The method generates nucleic acid molecules preferably comprising at least one functional unit. The functional unit is associated with the nucleic acid region of the nucleic acid by any number of the methods described below. The generation of the nucleic acid ligands generally follows the SELEX process described above, however, the functional unit can impart enhanced functionalities to the ligand that the nucleic acid alone is not capable of.

In another embodiment, facilitative nucleic acids are provided. Nucleic acids having facilitative properties are capable of mediating chemical reactions such as bond formation or bond cleavage. The nucleic acids can be modified in various ways to include other chemical groups that provide additional charge, polarizability, hydrogen bonds, electrostatic interaction, and fluxionality which assist in chemical reaction mediation. The other chemical groups can include, inter alia, alkyl groups, amino acid side chains, various cofactors, and organometallic moieties. The invention requires that the facilitative nucleic acids direct an interaction between the attached functional unit and a given target. The interaction is either covalent or non-covalent. The preferred interaction is a covalent bond formed between the nucleic acid (with or without an associated functional unit) and its target.

I. DEFINITIONS

Certain terms used to describe the invention herein are defined as follows:

"Nucleic acid" means either DNA, RNA, single-stranded or double-stranded and any chemical modifications thereof. Many of the modifications of the nucleic acid include the association of the nucleic acid with a functional unit as described herein. However, some modifications are directed to properties other than covalent attachment (i.e., stability, etc.). Modifications include, but are not limited to, those which provide other chemical groups that incorporate additional charge, polarizability, hydrogen bonding, electrostatic interaction, and fluxionality to the individual nucleic acid bases or to the nucleic acid as a whole. Such modifications include, but are not limited to, modified bases such as 2'-position base modifications, 5-position pyrimidine modifications, 8-position purine modifications, modifications at cytosine exocyclic amines, substitution of 5-bromouracil; backbone modifications, methylations, unusual base-pairing combinations such as the isobases isocytidine and isoguanidine and the like. Modifications can also include 3' and 5' modifications such as capping. Modifications that occur after each round of amplification are also compatible with this invention. Post-amplification modifications can be reversibly or irreversibly added after each round of amplification. One example of an irreversible post-amplification modification is the Splint-SELEX process described in Examples 2 and 3. For Splint-SELEX, the modification (typically a functional unit) is introduced to the nucleic acid ligand via a hybridization reaction with a portion of the nucleic acid ligand, usually the fixed regions. In Splint-SELEX, usually one or more functional units are attached to a nucleic acid sequence that hybridizes with a portion of the fixed region to become the modified nucleic acid ligand. Virtually any modification of the nucleic acid is contemplated by this invention.

A nucleic acid can take numerous forms including, but not limited to, those in which a nucleic acid region has 1) a single modification or functional unit attached at either the 5' or 3' end of nucleic acid sequence, 2) modifications or functional units at both the 5' and 3' ends of the nucleic acid sequence, 3) modifications or functional units added to individual nucleic acid residues, 4) modifications or functional units attached to all or a portion of all pyrimidine or purine residues, or modifications or functional units attached to all or a portion of all nucleotides of a given type, and 5) no modifications at all. The modifications or functional units may also be attached only to the fixed or to the randomized regions of each nucleic acid sequence of the candidate mixture. Any of these modifications may be introduced via the Splint-SELEX method described above, as well as by any other method known to one skilled in the art. Another embodiment of this invention for introducing a non-nucleic acid functional unit at random positions and amounts is by use of a template-directed reaction with non-traditional base pairs. This method uses molecular evolution to select the best placement of the non-nucleic acid group on the SELEX identified ligand. For example, a X-dY base pair could be used, where X is a derivatizable ribonucleotide and the deoxynucleotide dY would pair only with X. The X-RNA would contain the non-nucleic acid functional unit only at positions opposite dY in the dY-DNA template; the derivatized X base could be positioned in either the fixed or random regions or both, and the amount of X at each position could vary between 0–100%. The sequence space of non-evolved SELEX ligands would be increased from $N^4$ to $N^5$ by substituting this fifth base without requiring changes in the SELEX protocol. The attachment between the nucleic acid region and the functional unit can be covalent or non-covalent, direct or with a linker between the nucleic acid and the functional unit. The methods for synthesizing the nucleic acid, i.e., attaching such functional units to the nucleic acid, are well known to one of ordinary skill in the art.

Incorporation of non-nucleic acid functional units to produce nucleic acid ligands increases the repertoire of structures and interactions available to produce high affinity binding ligands. Various types of functional units can be incorporated to produce a spectrum of molecular structures. At one end of this structural spectrum are normal poly-nucleic acids where the ligand interactions involve only nucleic acid functional units. At the other, are fully substituted nucleic acid ligands where ligand interactions involve only non-nucleic acid functional units. Since the nucleic acid topology is determined by the sequence, and sequence partitioning and amplification are the basic SELEX process steps, the best ligand topology is selected by nucleic acid evolution.

"Nucleic acid test mixture" or "Nucleic acid candidate mixture" is a mixture of nucleic acids comprising differing, randomized sequence. The source of a "nucleic acid test mixture" can be from naturally-occurring nucleic acids or fragments thereof, chemically synthesized nucleic acids, enzymatically synthesized nucleic acids or nucleic acids made by a combination of the foregoing techniques, including any of the modifications described herein. In a preferred embodiment, each nucleic acid has fixed sequences surrounding a randomized region to facilitate the amplification process. The length of the randomized section of the nucleic acid is generally between 8 and 250 nucleotides, preferably between 8 and 60 nucleotides.

"Functional Unit" refers to any chemical species not naturally associated with nucleic acids, and may have any number of functions as enumerated herein. Specifically, any moiety not associated with the five standard DNA and RNA nucleosides can be considered a functional unit. Functional units that can be coupled to nucleotides or oligonucleotides include chemically-reactive groups, such as, photoreactive groups, active site directed compounds, lipids, biotin, proteins, peptides and fluorescent compounds. Often, the functional unit is recognizable by the target molecule. These non-nucleic acid components of oligonucleotides may fit into specific binding pockets to form a tight binding via appropriate hydrogen bonds, salt bridges, or van der Waals interactions. In one aspect, functional unit refers to any chemical entity that could be involved in a bond forming reaction with a target which is compatible with the thermal and chemical stability of nucleic acids, including the modifications described above. A functional unit may or may not be amplifiable with the nucleic acid region during the amplification step of the SELEX process. A functional unit typically has a molecular weight in the range of 2 to 1000 daltons, preferably about 26 to 500. Particularly preferred functional units include small organic molecules such as alkenes, alkynes, alcohols, aldehydes, ketones, esters, carboxylic acids, aromatic carbocycles, heterocycles, dienes, thiols, sulfides, disulfides, epoxides, ethers, amines, imines, phosphates, amides, thioethers, thioates, sulfonates and halogenated compounds. Inorganic functional units are also contemplated by this invention. However, in some embodiments of the invention, larger functional units can be included, such as polymers or proteins.

"Nucleic acid having facilitating properties" or "facilitating nucleic acid" or "facilitative nucleic acid" or "nucleic acid facilitator" refers to any nucleic acid which is capable of mediating or facilitating a chemical reaction. The chemical reaction can be a bond formation or bond cleavage reaction. The preferred embodiments of this invention are directed to bond formation reactions. The nucleic acid does not necessarily need to show catalytic turnover to be considered to have facilitating properties. The reaction rate of product formation can be increased by the presence of the nucleic acid, however, increased reaction rate is not a requirement for facilitating properties. A facilitating nucleic acid folds such that its three-dimensional structure facilitates a specific chemical reaction. The nucleic acid can mediate the chemical reaction either alone, in combination with another catalytic moiety coupled directly with the nucleic acid, or in combination with another catalytic moiety which could be found in solution. The other catalytic moieties can include organometallic moieties, metal ions, etc. The nucleic acid can cause different stereoisomers to be formed. The nucleic acid can mediate formation or cleavage of a variety of bond types, including, but not limited to, condensation/hydrolysis reactions, cycloaddition reactions (such as the Diels-Alder and Ene reaction), 1,3 dipolar conjugate addition to α,β-unsaturated compounds, Aldol condensations, substitution reactions, elimination reactions, glycosylation of peptides, sugars and lipids.

"Target" refers to any compound upon which a nucleic acid can act in a predetermined desirable manner. A target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, etc., without limitation. Virtually any biological effector would be a suitable target. Molecules of any size can serve as targets. A target can also be modified in certain ways to enhance the likelihood of an interaction between the target and the nucleic acid.

Targets can include, but are not limited to, bradykinin, neutrophil elastase, the HIV proteins, including tat, rev, gag, int, RT, nucleocapsid etc., VEGF, bFGF, TGFβ, KGF, PDGF, thrombin, theophylline, caffeine, substance P, IgE, sPLA$_2$, red blood cells, glioblastomas, fibrin clots, PBMCs, hCG, lectins, selectins, cytokines, ICP4, complement proteins, etc.

"Covalent Interaction" between a target and a nucleic acid means that a covalent bond is formed between the nucleic acid (with or without an associated functional unit) and its target. A covalent bond is a chemical bond formed between atoms by the sharing of electrons. A covalent interaction is not easily disrupted.

"Partitioning" means any process whereby members of the nucleic acid test mixture can be separated from the bulk of the test mixture based on the ability of the nucleic acid to bind to or interact with the target, the ability of the nucleic acid to facilitate a reaction involving its associated functional unit. Partitioning can be accomplished by various methods known in the art. Filter binding, affinity chromatography, liquid-liquid partitioning, HPLC, filtration, gel shift, density gradient centrifugation are all examples of suitable partitioning methods. The choice of partitioning method will depend on properties of the target and the product and can be made according to principles and properties known to those of ordinary skill in the art.

"Subtractive partitioning" refers to partitioning the bulk of the test mixture away from the nucleic acids involved in the interaction with the target. The desirable nucleic acids remain involved in the interaction with the target while the uninteracted nucleic acids are partitioned away. The uninteracted nucleic acids can be partitioned away based on a number of characteristics. These characteristics include, but are not limited to, the fact that the nucleic acids did not bind to the target, the fact the nucleic acid still has a functional unit that did not interact with the target and therefore that functional unit is still available for additional interaction, etc. This partitioning method is particularly useful for automating the selection process.

"Amplifying" means any process or combination of process steps that increases the amount or number of copies of a molecule or class of molecules. In preferred embodiments, amplification occurs after members of the test mixture have been partitioned, and it is the facilitating nucleic acid associated with a desirable product that is amplified. For example, amplifying RNA molecules can be carried out by a sequence of three reactions: making cDNA copies of selected RNAs, using the polymerase chain reaction to increase the copy number of each cDNA, and transcribing the cDNA copies to obtain RNA molecules having the same sequences as the selected RNAs. Any reaction or combination of reactions known in the art can be used as appropriate, including direct DNA replication, direct RNA amplification and the like, as will be recognized by those skilled in the art. The amplification method should result in the proportions of the amplified mixture being essentially representative of the proportions of different sequences in the mixture prior to amplification. It is known that many modifications to nucleic acids are compatible with enzymatic amplification. Modifications that are not compatible with amplification can be made after each round of amplification, if necessary.

"Randomized" is a term used to describe a segment of a nucleic acid having, in principle, any possible sequence over a given length. Randomized sequences will be of various lengths, as desired, ranging from about eight to more than one hundred nucleotides. The chemical or enzymatic reactions by which random sequence segments are made may not yield mathematically random sequences due to unknown biases or nucleotide preferences that may exist. The term "randomized" is used instead of "random" to reflect the possibility of such deviations from non-ideality. In the techniques presently known, for example sequential chemical synthesis, large deviations are not known to occur. For short segments of 20 nucleotides or less, any minor bias that might exist would have negligible consequences. The longer the sequences of a single synthesis, the greater the effect of any bias.

A bias may be deliberately introduced into a randomized sequence, for example, by altering the molar ratios of precursor nucleoside (or deoxynucleoside) triphosphates in the synthesis reaction. A deliberate bias may be desired, for example, to affect secondary structure, to introduce bias toward molecules known to have facilitating activity, to introduce certain structural characteristics, or based on preliminary results.

"SELEX" methodology involves the combination of selection of nucleic acid ligands which interact with a target in a desirable manner, for example binding to a protein, with amplification of those selected nucleic acids. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to amplify the nucleic acid associated with a desirable product.

"Chemi-SELEX" is a method wherein nucleic acids in a nucleic acid test mixture are capable of facilitating an interaction with a target. Preferably, but not necessarily, the nucleic acids are associated with a functional unit and the interaction is a covalent bond. The nucleic acid is contacted with a target under conditions favorable for ligand binding either directly or through facilitated bond formation. The nucleic acid or the functional unit must interact with the target in order to fall within the scope of Chemi-SELEX. The nucleic acid ligands having predetermined desirable characteristics are then identified from the test mixture. The nucleic acid can be identified by its ability to act on a given target in the predetermined manner (e.g., bind to the target, modify the target in some way, etc.). The desirable nucleic acids can then be partitioned away from the remainder of the test mixture. The nucleic acid, with or without its associated functional unit, can be amplified as described in the SELEX method. The amplified nucleic acids are enriched for the nucleic acids which have desirable properties. If a functional unit was associated with the nucleic acid, the amplified nucleic acids are then recoupled to the functional unit (if the functional unit is non-amplifiable), recontacted with the target, and the iterative cycling of the selection/amplification steps of the SELEX process are incorporated to synthesize, select and identify desirable nucleic acids.

In one aspect, the present invention depends on the ability of a nucleic acid to mediate an interaction between the functional unit and the target of interest. The method requires the initial preparation of a nucleic acid test mixture. In general, the rationale and methods for preparing the nucleic acid test mixture are as outlined in the SELEX Patent Applications described earlier which are herein incorporated by reference. Briefly, a nucleic acid test mixture of differing sequences is prepared. Each nucleic acid in the test mixture generally includes regions of fixed sequences (i.e., each of the members of the test mixture contains the same sequences in the same location) and regions of randomized sequences. The fixed sequence regions are selected either: (a) to assist in the amplification steps described in detail in the SELEX patents, (b) to mimic a sequence known to mediate a reaction, or (c) to enhance the concentration of nucleic acids of a given structural arrangement in the test mixture. The randomized sequences can be totally randomized (i.e., the probability of finding a base at any position being one in four) or only partially randomized (e.g., the probability of finding a base at any location can be selected at any level between 0 and 100 percent). The nucleic acids found in the nucleic acid test mixture will include those capable of proper folding in order to specifically facilitate various chemical reactions, such as reactions between the target and the associated functional unit; those capable of interacting directly with the target, the specificity of which will be enhanced by the associated functional unit.

The nucleic acid test mixture can be modified in various ways to enhance the probability of the nucleic acids having facilitating properties or other desirable properties, particularly those which enhance the interaction between the nucleic acid and the target. The modifications contemplated by this invention are any modifications which introduce other chemical groups (functional units) that have the correct charge, polarizability, hydrogen bonding, electrostatic interaction, or fluxionality and overall can adopt the shape needed to stabilize the reaction transition state and facilitate specific chemical reactions, without limitation. The modifications that may enhance the active site of the nucleic acid include hydrophilic moieties, hydrophobic moieties, metal atoms in various oxidation states, rigid structures, functional groups found in protein enzyme active sites such as imidazoles, primary alcohols, carboxylates, guanidinium groups, amino groups, thiols and the like. Additionally, organometallic and inorganic metal catalysts can be incorporated as the other chemical group of the nucleic acid, as can redox reactants.

The individual components of a nucleic acid test mixture can be modified in various ways. Suitable modifications include, but are not limited to, modifications on every residue of the nucleic acid, on random residues, on all pyrimidines or purines, or all specific bases (i.e., G, C, A, T or U), or one modification per nucleic acid. It is also recognized that certain molecules (e.g., metal catalysts and the like) can be in solution, not attached to the nucleic acid, and be useful in mediating the reaction in concert with the mediating action of the nucleic acid. It is believed that as long as the nucleic acid coupled to the functional unit is in some way associated with the interaction between the nucleic acid and the target, that the method and resulting nucleic acids fall within the scope of this invention. It is also recognized that modification is not a prerequisite for facilitating activity or binding ability of the nucleic acids of the invention.

As described earlier, the nucleotides can be modified in any number of ways, including modifications of the ribose and/or phosphate and/or base positions. Certain modifications are described in copending U.S. patent applications Ser. No. 08/117,991 entitled "High Affinity Nucleic Acid Ligands Containing Modified Nucleotides", now abandoned (See also, U.S. Pat. No. 5,660,985) U.S. Ser. No. 08/076,735 entitled "Method for Palladium Catalyzed Carbon-Carbon Coupling and Products", now issued as U.S. Pat. No. 5,428, 149, U.S. Ser. No. 08/264,029 entitled "Novel Method of Preparation of Known and Novel 2' Modified by Pyrimidines Nucleosides Intramolecular Nucleophilic Displacement" now issued as U.S. Pat. No. 5,756,703, and U.S. Ser. No. 08/347,600 entitled "Purine Nucleoside Modifications by Palladium Catalyzed Methods", now issued as U.S. Pat. No. 5,580,972, which are herein incorporated by reference. In one embodiment, modifications are those wherein another chemical group is attached to the 5-position of a pyrimidine, the 8-position of a purine, or the 2' position of a sugar. There is no limitation on the type of other chemical group that can be incorporated on the individual nucleotides. In the preferred embodiments, the resulting modified nucleotide is amplifiable or can be modified subsequent to the amplification steps.

As an example, which is not meant to limit the invention in any way, one can envision a biomimetic nucleic acid. One choice for modification of the nucleic acids includes modification which would make certain bases appear more like proteins in their chemical and physical properties. Certain modifications of pyrimidine and purine nucleotide bases can be made to make the nucleic acid appear to have "side chains" similar to the amino acid side chains of proteins.

Several synthetic methods are available to attach other chemical groups, in this case amino acid derivatives, to the 5-position of a pyrimidine or the 8-position of a purine. Methods for modifying pyrimidines at the 5-position have been described in U.S. patent application Ser. No. 08/076, 735 supra as well as other published procedures. Numerous published procedures are known for modifying nucleic acids including, but not limited to the following (Limbach, P A, et al.,1994. *Nucleic Acids Res.* 22:2183–2196 and references cited therein; Hayakawa H, et al., 1985. *Tetrahedron* 41:1675–83; Crouch G J et al., 1994. *Nucleosides Nucleotides* 13:939–44; Scheit K H, 1966. *Chem. Ber.* 98:3884; Bergstrom and Ruth, 1976. *J. Am. Chem. Soc.* 98:1587–89; Bergstrom D E et al., 1978. *J. Am. Chem. Soc.* 100:8106–12; Bergstrom D E et al., 1978. *J. Org. Chem.* 43:2870; Bergstrom D E et al.,1981. *J. Org. Chem.* 46:1432–41; Bergstrom D E. 1982. *Nucleosides Nucleotides* 1:1–34; Crisp G T et al.,1990. *Tetrahedron Lett.* 31:1347–50; Hobbs F W Jr. 1989. *J Org. Chem.* 54:3420–22; Hirota K et al.,1993. *Synthesis* 213–5; Nagamachi T et al.,1974. *J. Med. Chem.* 17:403–6; Barton D H R et al., 1979. *Tetrahedron Lett.* 3:279–80; Hirota K et al., 1992. *J. Org. Chem.* 57:5268; Mamos P et al., 1992. *Tetrahedron Lett.* 33:2413–16; Sessler J L et al., 1993. *J. Am. Chem. Soc.* 115:10418–19; Long R A et al., 1967. *J. Org. Chem.* 32:2751–56; Prakash T P et al., 1993. *Tetrahedron* 49:4035; Jankowski A J et al., 1989. *Nucleosides Nucleotides* 8:339; Kumar and Buncel, 1984. *J. Inorg. Biochem.* 22:11–20; Moffatt J G. 1979. in *Nucleoside Analogues*, eds. R T Walker, E De Clercq, F Eckstein pp. 71–163 New York: Plenum Press; Townsend L B. 1988. *Chemistry of Nucleosides and Nucleotides* pp.59–67 New York: Plenum Press; Verheyden J P H et al., 1971. *J. Org. Chem.* 36:250–54; Wagner D, et al., 1972. *J. Org. Chem.* 37:1876–78; Sproat B S et al., 1991. in *Oligonucleotides and Analogues A Practical Approach*, ed. F. Eckstein pp.49–86. New York: Oxford University Press; Lesnik E A et al., 1993. *Biochemistry* 32:7832–38; Sproat B S et al., 1991. *Nucleic Acids Res.* 19:733–38; Matsuda A et al., 1991. *J. Med. Chem.* 34:234–39; Schmit C. 1994. *Synlett* 238–40; Imazawa M et al., 1979. *J. Org. Chem.* 44:2039–4; Schmit C. 1994. *Synlett* 241–42; McCombie S W et al., 1987. *Tetrahedron Let.* 28, 383–6; Imazawa M, et al., 1975. *Chem. Pharm. Bull.* 23:604–10; Divakar K J et al., 1990. *J. Chem. Soc., Perkin Trans.*1 969–74; Marriott J H et al., 1991 *Carbohydrate Res.* 216:257–69; Divakar K J et al., 1982. *J. Chem. Soc., Perkin Trans.* 1 1625–28; Marriott J H et al., 1990. *Tetrahedron Lett.* 31:7485)

Nucleotides modified with other chemical groups in place of the above-described amino acids are also contemplated by this invention. Oftentimes, a working assumption can be made about which modified nucleotides would be most desirable for addition to the nucleic acid test mixture.

The methods described herein do not include all of the schemes for introducing non-nucleic acid functional units, such as peptides, into an oligonucleotide. However, such methods would be well within the skill of those ordinarily practicing in the art. Putting a peptide on every uridine, for example, has several advantages as compared with other methods for use in the SELEX procedure. First, the peptide is introduced throughout both the random and fixed regions, so that evolved RNA ligands could bind close to the peptide binding site. Second, distributing the peptide at multiple sites does not restrict the geometry of RNA and does not interfere with SELEX process identification of the optimal peptide position. Third, one can use pre-derivatized nucleotides in the SELEX process. Post-transcription modification may require additional time and expertise and introduces the additional variable of coupling efficiency.

In one embodiment of the invention, referred to as splint SELEX, the functional unit is attached to a nucleic acid by first attaching the functional unit to a nucleic acid that is complementary to a region of the nucleic acid sequence of the ligand and then allowing the nucleic acid with functional unit to hybridize to the nucleic acid. This splint nucleic acid is then subjected to the SELEX process. In the preferred embodiment, the functional unit oligonucleotide is DNA, and hybridizes to the fixed region of the nucleic acid ligand or at least a region of the nucleic acid ligand that is not involved in the binding or facilitating reaction to the target.

In one variation of this embodiment, the SELEX process is accomplished by the preparation of a candidate mixture of nucleic acid sequences comprised of fixed and randomized regions. The candidate mixture also contains an oligonucleotide attached to a selected functional group. The oligonucleotide is complementary to the fixed region of the nucleic acid candidate mixture, and is able to hybridize under the conditions employed in SELEX for the partitioning of high affinity ligands from the bulk of the candidate mixture. Following partitioning, the conditions can be adjusted so that the oligo-functional unit dissociates from the nucleic acid sequences.

Advantages to this embodiment include the following: 1) it places a single functional unit, such as a peptide analog, at a site where it is available for interaction with the random region of nucleic acid sequences of the candidate mixture; 2) because the functional unit is coupled to a separate molecule, the coupling reaction must only be performed once, whereas when the functional unit is coupled directly to the SELEX ligand, the coupling reaction must be performed at every SELEX cycle. (aliquots from this reaction can be withdrawn for use at every cycle of SELEX); 3) the coupling chemistry between the functional unit and the oligonucleotide need not be compatible with RNA integrity or solubility—thus simplifying the task of coupling; 4) in cases where the functional unit forms a covalent complex with the target, the SELEX derived nucleic acid ligand portion of the selected members of the candidate mixture can be released from the target for amplification or identification; and 5) following the successful identification of a nucleic ligand, the tethered portion of nucleic acid can be made into a hairpin loop to covalently attach the two portions of the nucleic acid ligand.

Due to the nature of the strong interaction between the nucleic acid and the target (i.e., covalent bond), the entire selection procedure can be accomplished in a single tube, thereby allowing the process (including partitioning) to be automated.

The ligands identified by the method of the invention have various therapeutic, prophylactic and diagnostic purposes. They are useful for the diagnosis and/or treatment of diseases, pathological or toxic states.

The examples below describe methods for generating the nucleic acid ligands of the present invention. As these examples establish, nucleotides and oligonucleotides containing a new functional unit are useful in generating nucleic acid ligands to specific sites of a target molecule.

Example 1 describes the ability of a nucleic acid ligand to facilitate a covalent reaction between a 5' guanosine monophosphorothioate functional unit and a bradykinin target.

Examples 2 and 3 demonstrate that nucleic acid ligands can be evolved with can facilitate a reaction between a valyl phosphonate functional unit that is attached via the splint-SELEX process to a nucleic acid test mixture and neutrophil elastase. Example 3 describes the first DNA sequences known to have this facilitating property.

Example 4 describes the ability of a nucleic acid ligand to facilitate a covalent reaction between its associated 5-iodouracil residue functional units and the target protein HIV-1 Rev.

EXAMPLE 1

5'-phosphorothioate-modified RNA binding to N-bromoacetyl-bradykinin

This example describes a Chemi-SELEX procedure wherein RNA is modified with a 5' guanosine monophosphorothioate (GMPS) functional unit and the target for which a ligand is obtained is N-bromoacetylated-bradykinin (BrBK). This example describes the selection and analysis of a 5' guanosine monophosphorothioate-substituted RNA (GMPS-RNA) which specifically recognizes N-bromoacetylated-bradykinin (BrBK) and accelerates the formation of a thioether bond between the RNA and the BrBK peptide. Previous work in this area showed that it was difficult to obtain ligands to bradykinin both in free solution and conjugated to a support matrix. As will be described below, RNA showing a 6700-fold increase in $k_{cat}/K_m$ and a 100-fold increase in binding affinity for N-bromoacetyl-bradykinin relative to the starting pool was identified. This RNA binds its substrate with high specificity, requiring both the amino- and carboxy-terminal arginine residues of the peptide for optimal activity.

A. The Chemi-SELEX

The Chemi-SELEX reaction was carried out using 5' guanosine monophosphorothioate (GMPS) as the functional unit attached to an RNA test mixture and bromoacetylated bradykinin (BrBK) as the target. GMPS-RNA is selected for the ability to rapidly substitute the thioate group of the RNA for the bromide group of BrBK. The product, BK-S-RNA, is then partitioned subtractively from the remaining unreacted GMPS-RNA and re-amplified prior to continuing with another selection cycle.

1. GMPS-RNA

The Chemi-SELEX was performed with an initial random repertoire of approximately $5 \times 10^{13}$ GMPS-RNA molecules of length 76 nucleotides having a central region of 30 randomized nucleotides (30N1) (SEQ ID NO: 1), described in detail by Schneider et al., (FASEB, 7, 201 (1993)), with the non-random regions serving as templates for amplification. The nucleic acid was formed by inclusion of GMPS in the initial and all subsequent transcription reactions such that it was preferentially utilized over equimolar GTP in the priming of transcription by T7 RNA polymerase such that approximately 80% of the full length product was initiated by GMPS. GMPS-RNA was transcribed and purified by Amicon Microcon-50 spin separation to remove excess GMPS. GMPS-RNA is purified away from non-GMPS RNA using Thiopropyl Sepharose 6B, eluted from the matrix with dithiothreitol (DTT) and purified from the DTT with another Microcon-50 spin separation. Thiopropyl sepharose 6B (Pharmacia) was pre-washed in column buffer (500 mM NaCl, 20 mM HEPES pH 7.0) and then spun dry at 12,000 g prior to use. For GMPS-RNA purification, Microcon-50 column-purified RNA was brought to a final concentration of 500 mM NaCl, 10 mM EDTA and 20 mM HEPES pH 7.0 and added to matrix at a measure of 25 µL per 60 µL void volume. The mix was then reacted at 70° C. for 5 minutes, spun at 12,000 g, spin-washed with four column volumes of 90% formamide, 50 mM MES pH 5.0 at 70° C., spin-washed with four column volumes of 500 mM NaCl in 50 mM MES, pH 5.0 and spin-eluted with four column volumes of 100 mM DTT in 50 mM MES, pH 5.0. These conditions were optimized for the retention and subsequent elution of only GMPS-RNA.

2. Bromoacetylated bradykinin

Bromoacetylated bradykinin (BrBK) was used as the target in this example. BrBK was synthesized by reacting 50 µL of 5 mM bradykinin with three successive 250 µL portions of 42 mM bromoacetic acid N-hydroxysuccinimide ester at 12 minute intervals at room temperature. Excess bromoacetic acid N-hydroxysuccinimide ester was removed by filtration over 5 µL of aminoethyl acrylamide (five minutes of reaction at room temperature), followed by separation of the BrBK over GS-10 sepharose. BrBK concentration was determined at 220 nm using an absorption coefficient of 12,000 $cm^{-1}M^{-1}$.

3. The selection reaction

Those species of GMPS-RNA which are most capable of carrying out the reaction with BrBK are selected iteratively through multiple rounds of SELEX. Rounds of selection were carried out in reaction buffer with 1.1 mM BrBK and with the GMPS-RNA concentrations for the given times and temperatures indicated in Table I. During the selection, the BrBK peptide concentration was kept at 1.1 mM, a concentration 12-fold lower than the $K_m$ of the round 0 pool with BrBK. Proceeding through the selection, reaction time was restricted and temperature of the reaction was decreased in order to limit the reaction to 5% or less of the total GMPS-RNA. The object was to maintain second-order reaction conditions in order to select for improvements in both binding and chemistry. Activity of the BrBK was assayed at 12.5 µM BrBK with 25 µM GMPS-RNA; when the reaction was carried out to completion, 50% of the RNA was covalently bound by BrBK indicating that bromoacetylation of the peptide was essentially complete.

Reactions were quenched with a final concentration of either 235 mM sodium thiophosphate (rounds 1–8) or sodium thiosulfate (rounds 9–12) and subtractively partitioned either on denaturing 7 M urea 8% polyacrylamide APM gels (rounds 1–6) or by affinity chromatography (rounds 7–12). % RNA reacted refers to the percent of the total GMPS-RNA present as BK-S-RNA from acrylamide gel partitioning, or, as freely eluting BK-S-RNA in affinity column partitioning. Background was subtracted from the recovered RNA in both of these cases; background refers to the amount of RNA recovered from a control treatment where the reaction was quenched prior to the addition of the BrBK. The background ratio is the ratio of reacted RNA to that present as background. An attempt was made to keep this ratio between 2 and 10 throughout the rounds of SELEX by adjusting the reaction time.

The subtractive partitioning was accomplished either by subtraction of the GMPS-RNA upon Thiopropyl Sepharose 6B, or by separation of the two species on an APM polyacrylamide gel. [(N-Acryloylamino)phenyl]mercuric Chloride (APM) was synthesized and used at a concentration of 25 µM in denaturing polyacrylamide gel electrophoresis for the retardation of thiol-containing RNA as reported by G. L. Igloi, *Biochemistry* 27, 3842 (1988). GMPS-RNA was purified from APM-polyacrylamide by elution in the presence of 100 mM DTT. In concurrence with the cited literature, it was found that freshly purified, APM-retarded GMPS-RNA when re-run on an APM gel gave a free band of non-retarded RNA consisting of approximately three percent of the total GMPS-RNA applied. Free-running RNA was problematic in that it ran very closely to BK-RNA (regardless of the percent acrylamide used in the gel) and thus increased the background during partitioning. When this free-running RNA was purified from the gel and rerun on an APM gel, approximately 50% of this RNA remained free-running, with the balance of RNA running as GMPS-RNA. The amount of free-running RNA was proportional to the amount of time spent during precipitation, but was not dependent on the effect of pH, the presence or absence of either DTT, magnesium acetate, formamide, urea, or heat.

Reverse transcription and polymerase chain reaction were carried out as reported by Schneider et al., (FASEB, 7, 201 (1993)). The $k_{obs}$ value of the GMPS-RNA pool increased 100-fold between rounds 4 and 6, increasing only 2-fold with further rounds. Reactions to determine $k_{obs}$ values were carried out at 0° C. in reaction buffer (50 mM HEPES, pH 7.0, 5 mM $MgCl_2$, 150 mM NaCl) at 2 µM GMPS-RNA and 130 µM BrBK, with monitoring at 0, 1, 3, 10, 30, and 90 minutes. GMPS-RNA was denatured at 70° C. for 3 minutes and allowed to slow cool at room temperature prior to dilution to final reaction buffer conditions, transfer to ice, and addition of BrBK. Reactions were quenched on ice with 235 mM sodium thiosulfate and run on a denaturing 7 M urea 8% polyacrylamide APM gel. $k_{obs}$ values were determined as the negative slope of the linear range of data points from plots relating the concentration of unreacted GMPS- RNA vs. time. Round 10 and round 12 pools were used for cloning and sequencing.

B. The Clones

Fifty six independent clones were sequenced, which resulted in 29 different sequences shown in Table II (SEQ ID NOs: 2–37). Approximately ⅓ of the total sequences have the core consensus 5'UCCCC(C)G 3' (SEQ ID NO: 38) positioned freely along the length of the randomized region. Computer modeling of sequences containing this motif invariably had this consensus region base paired with the 5' terminal GGGA (see reactant 12.16, (SEQ ID NO: 3)). Conceivably, such base-pairing fixes the terminal GMPS nucleotide, coordinating the thioate group for reaction with the acetyl α-carbon of BrBK. Clones which did not contain the 5'UCCCC(C)G 3 motif, such as reactant 12.1 (SEQ ID NO: 33), did not usually have the 5'GMPS base-paired in computer-generated structures. Sixteen reactants were compared with the 30N1 bulk pool for reactivity with BrBK; all tested reactants show a 10- to 100-fold increase in $k_{obs}$ relative to the original pool. Reactant 12.1 was chosen for further kinetic analysis based on three criteria: (i) in a preliminary study of reaction inhibition with competing bradykinin it had the lowest $K_i$ for bradykinin (data not shown); (ii) it was the most frequently represented molecule in the round 12 population; and (iii), it had the second fastest $k_{obs}$ of the reactants tested.

The selected increase in $k_{obs}$ of reactant 12.1 is attributable to increases in both reactivity and binding. In reaction with BrBK, reactant 12.1 shows a 67-fold increase in $k_{cat}$ over that of bulk 30N1 GMPS-RNA, with a 100-fold reduction in $K_m$, giving an overall 6700-fold increase in $k_{cat}/K_m$ (see Table 1).

C. Specificity

Structural elements of BrBK required for optimal binding by reactant 12.1 were studied through inhibition of the reaction by bradykinin analogs. While inhibition by BK is not measurable in the reaction of bulk 30N1 GMPS-RNA with BrBK (data not shown), native bradykinin (BK) has a $K_i$ of 140±60 µM for the reaction between reactant 12.1 and BrBK. This value is nearly identical to the $K_m$ of the uninhibited reaction. Des-Arg$^9$-BK (a BK analog lacking the carboxyl terminal arginine) has a $K_i$ of 2.6±0.5 mM. Thus, the lack of the carboxy terminal arginine decreases the binding between BK and reactant 12.1 approximately 18-fold. Furthermore, des-Arg$^1$-BK (a BK analog lacking the amino terminal arginine) does not show any measurable inhibition of the reaction between reactant 12.1 and BrBK, indicating that the amino-terminal arginine is absolutely required for the observed binding between reactant 12.1 and BrBK. Recognition of arginine must be in the context of the peptide, however, since free L-arginine alone does not measurably inhibit the reaction. Thus, the increase in affinity of reactant 12.1 over that of the bulk 30N1 GMPS-RNA for BrBK is in part attributable to reactant recognition of the amino terminal arginine of BrBK, and to a lesser extent the carboxy terminal arginine.

The intrinsic reaction activity of reactant 12.1 was studied using N-bromoacetamide (BrAcNH$_2$) as a minimal bromoacetyl structure. As shown in Table III, the $K_m$ and $k_{cat}$ values in the reactions of reactant 12.1 and the 30N1 RNA pool with BrAcNH$_2$ are approximately the same. Therefore, the enhanced reaction rate of reactant 12.1 with BrBK is apparently due not to increased nucleophilicity of the thioate group, but is rather a result of steric and/or entropic factors in the positioning of the two substrates.

EXAMPLE 2

Splint SELEX to Identify Elastase Inhibitors

Highly potent and specific inhibitors of human neutrophil elastase were produced by an approach that incorporates the technologies of medicinal and combinatorial chemistry. A small-molecule covalent inhibitor of elastase (the valyl phosphonate functional unit) was coupled to a randomized pool of RNA, and this assembly was iteratively selected for sequences that promote a covalent reaction with the elastase target active site. The winning sequences increase both the binding affinity and reactivity over that of the small molecule functional unit alone; the overall increase in the second-order rate of inactivation was ~10$^4$-fold. The rate of cross-reaction with another serine protease, cathepsin G, was reduced >100-fold. These compounds inhibit elastase expressed from induced human neutrophils, and prevent injury in an isolated rat lung model of ARDS. This strategy is generally useful for increasing the potency and specificity of small molecule ligands.

The splint SELEX process was performed by preparing a standard SELEX candidate mixture and a single compound containing a valyl phosphonate functional unit attached to a nucleic acid sequence that hybridizes to a portion of the fixed region of the candidate mixture of nucleic acid sequences.

Functional Unit Synthesis

The diphenylphosphonovaline co-ligand 3 may be synthesized from the known Cbz-protected diphenylphosphonovaline 1 as outlined in Scheme 1. Condensation of isobutyraldehyde, benzyl carbamate and triphenylphosphite gave compound 1 in 55% yield. The Cbz group was removed with 30% HBr/AcOH and the resulting HBr salt converted to the free amine 2 in 86% overall yield. Treatment of 2 with N,N'-disuccinimidyl carbonate (DSC) in acetonitrile provides the desired co-ligand 3 which may be conjugated to the amino-DNA splint via the NHS ester moiety.

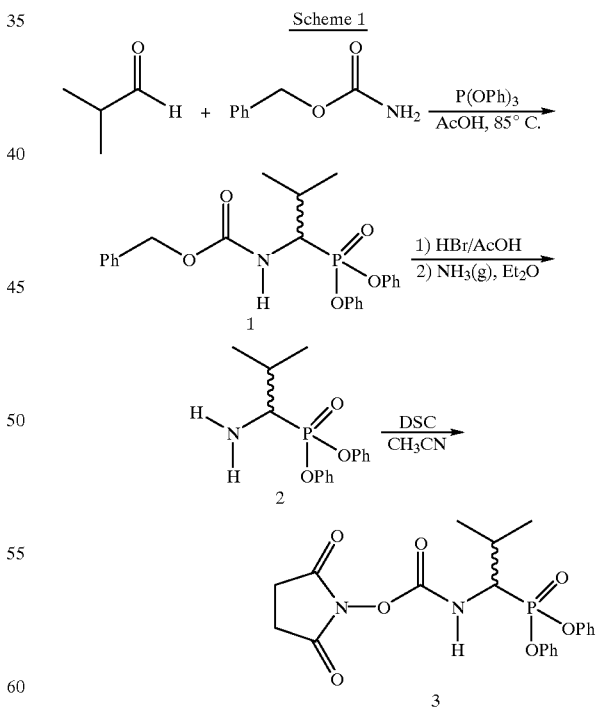

Synthesis of N-Benzyloxycarbonyl-O,O'-Diphenylphosphono-valine(1)

Benzyl carbamate (30.23 g, 0.20 mol), isobutyraldehyde (27.25 mL, 0.30 mol) and triphenylphosphite (52.4 mL, 0.20 mol) were dissolved in 30 mL of glacial acetic acid in a 250 mL round bottom flask. After stirring at room temperature for 5 minutes, the solution was heated to 80–85° C. in an oil bath for 3 hours. The mixture was concentrated to an oil on a rotary evaporator equipped with a vacuum pump and using a bath temperature of 90–95° C. The oil was subsequently dissolved in 250 mL of boiling methanol, filtered and chilled to −15° C. to promote crystallization. The crystalline solid was filtered, washed with cold methanol, air dried and then dried overnight in a vacuum desiccator to give 48.2 g (55%) of the product: $^1$H NMR (d$_6$-DMSO) δ 1.05(d, 6H, J=6.7 Hz), 2.28 (dq, 1H, J=6.2, 6.7 Hz), 4.22 (ddd, 1H, J$_{HH}$=6.2, 10.2 Hz, J$_{HP}$=17 Hz), 5.13 (d, 1H, J=12.6 Hz), 5.13 (d, 1H, J=12.6 Hz), 7.11–7.42 (ArH, 15H), 8.09 (d, 1H, J=10.2 Hz).

Synthesis of O,O'-Diphenylphosphonovaline(2)

N-Benzyloxy-carbonyl-O,O'-diphenylphosphonovaline (21.97 g, 50.0 mmol) was treated with 18 mL of 30% HBr/HOAc. After 1 hour, the solidified reaction mixture was suspended in 25 mL of glacial acetic acid and concentrated to an orange solid. The solid was triturated with 50 mL of ether overnight, filtered and washed with ether until off-white. A total of 17.5 g (91%) of the HBr salt was obtained. This salt was suspended in 150 mL of ether and gaseous ammonia bubbled through the suspension for 15 minutes. The ammonium bromide was filtered off and washed with ether. The filtrate was concentrated and the solid residue dried under vacuum to give 13.05 g (86% overall) of the desired free amine 2: $^1$H NMR (d$_6$-DMSO) δ 1.03(d, 3H, J=7.0 Hz), 1.06 (d, 3H, J=7.1 Hz), 1.93 (br, 2H, —NH$_2$), 2.16–2.21 (m, 1H), 3.21 (dd, 1H, J$_{HH}$=3.7 Hz, J$_{HP}$=14.5 Hz), 7.17–7.23 (ArH, 6H), 7.33–7.41 (ArH, 4H).

Synthesis of N-Succinimidyloxycarbonyl-O,O'-Diphenylphosphonovaline(3)

N,N'-Disuccinimidyl carbonate (243 mg, 0.95 mmol) was dissolved in 5 mL of dry acetonitrile. A solution of O,O'-diphenylphosphonovaline (289 mg, 0.95 mmol) in 5 mL of dry acetonitrile was added and the mixture stirred at room temperature for 2 hours. The precipitated product was filtered, washed with dry acetonitrile and dried under vacuum to give 229 mg (54%) of a white solid: $^1$H NMR (d$_6$-DMSO) δ 1.06 (d, 3H, J=6.5 Hz), 1.08 (d, 3H, J=6.7 Hz), 2.25–2.39 (m, 1H), 2.81 (br s, 4H), 4.12 (ddd, 1H, J$_{HH}$=6.0, 10.0 Hz, J$_{HP}$=18 Hz), 7.14–7.29 (ArH, 6H), 7.36–7.45 (ArH, 4H), 9.18 (d, 1H, J=10.0 Hz); $^{13}$C NMR (d$_6$-DMSO) δ 18.28 (d, J$_{CP}$=7.4 Hz), 19.82 (d, J$_{CP}$=10.4 Hz), 25.21, 28.69 (d, J$_{CP}$=4.3 Hz), 54.61 (d, J$_{CP}$=56.1 Hz), 120.43, 120.48, 125.16, 125.33, 129.73, 129.85, 149.54 (d, J$_{CP}$=9.6 Hz), 149.70 (d, J$_{CP}$=10.1 Hz), 152.72, 170.56; $^{31}$P NMR (d$_6$-DMSO, 85% H$_3$PO$_4$ reference) δ 18.02 ppm; Anal Calcd for C$_{21}$H$_{23}$N$_2$O$_7$P: C, 56.50; H, 5.19; N, 6.28; P, 6.94. Found: C, 56.35; H, 5.16; N, 6.29; P, 6.52.

Ligand Selection

The valyl phosphonate was activated via an NHS ester. This compound was coupled to the 5' hexyl amine linker of a 19-mer DNA oligo complementary to the 5'-fixed region of 40N7.1(SEQ ID NO: 38)) candidate mixture.

Synthesis of the starting RNA pool used 70 pmol of 40N7.1 DNA as template. This DNA was produced by PCR amplification from 10 pmol of synthetic DNA. The transcription buffer is 80 mM HEPES pH 7.5, 12 mM MgCl$_2$, 2 mM spermidine, 40 mM DTT, 1 mM GTP, 0.5 mM ATP, 1.5 μM α-$^{32}$P-ATP" (800 Ci/mmol, New England Nuclear), 2 mM each uridine- and cytosine-2'-amino nucleoside triphosphate, 0.01 unit/μl inorganic pyrophosphatase (Sigma), ~0.5 μM T7 RNA polymerase. Transcription was at 37° C. for 10–14 hrs. Full-length transcripts were purified by electrophoresis on an 8% acrylamide/7M urea TBE-buffered polyacrylamide gel.

Purified RNA was mixed with a 1.1-fold excess of splint DNA, and annealed by heating to 65° C. followed by cooling to 35° C. over 5 min. This hybrid was mixed with hNE (Calbiochem) at a 5- to 20-fold excess of RNA, and allowed to react for 5–15 minutes at 37° C. The reaction was quenched by addition of sodium dodecyl sulfate (SDS) to 0.1%. Volumes less than 200 μl were loaded directly on a 4% polyacrylamide gel with SDS added to 0.025%, and buffered with TBE. Larger volumes were concentrated by ultrafiltration through a Centripor 50 K MWCO filter cartridge centrifuged at 3000×g at 10° C., then loaded on the gel. The gel was run at 300V for 2 hr, and the bands of conjugated and unconjugated RNA were visualized by autoradiography. The band corresponding to the RNA:splint DNA:hNE complex was excised, crushed, and eluted in a buffer of 50 mM Tris pH7.5/4M guanidinium isothiocyanate/10 mM EDTA/2% sodium sarcosyl/1% β-mercaptoethanol at 70° C. for 30 minutes. The eluate was recovered by centrifugation through Spin-X 0.45 μm cellulose acetate microcentrifuge filter cartridges. The RNA was then ethanol precipitated and resuspended in 50 μl H$_2$O.

To the 50 μl RNA, 6 μl of 10×RT buffer (1×=50 mM HEPES pH7.5/50 mM NaCl/10 mM MgCl$_2$/5 mM DTT), 100 pmol each of the 5' and 3' primers, and 0.67 mM each dNTP were added. The mixture was heated to 65° C., then cooled to 35° C. over 5 minutes. The reaction was initiated by addition of 40 units AMV reverse transcriptase (Life Sciences), and incubation continued at 35° C. for 5 minutes. The temperature was then raised by 2° C. per minute for 15 minutes to 65° C. At 52–55° C., another 40 unit reverse transcriptase was added.

The polymerase chain reaction was initiated by adding 2 μl 1M potassium acetate, 10 μl 40% acetamide, 30 μl H$_2$O, and 2.5 units TaqDNA polymerase (Promega). 16 cycles were carried out at 92° C./30 sec→62° C./(20+n×10) sec (where n is the cycle number)→72° C./40 sec. The DNA was ethanol precipitated and resuspended in 100 μlH$_2$O. 10 μl of this reaction was used as a transcription template in the next round of SELEX.

Ten Cycles of SELEXion were Carried out Using this Protocol.

Sequence/Structure of Ligands

The sequences of 64 RNAs from the round 10 pool were determined and shown in TABLE IV. 12 of these are clones, or "psuedo-clones" of other sequences. Pseudo-clones are sequences that differ at only one or two positions from other sequences, and probably arose by errors in replication or transcription. Three features of these sequences are apparent by inspection. First, the mononucleotide composition of the randomized regions are not biased toward G (0.19 mol fraction G). PolyG is known to bind and inhibit elastase. Second, virtually all clones (61/64) extend the length of the splint helix by 2 or 3 base-pairs, usually with the sequence "CA" or "CAG". Third, 23/64 clones share the sequence "GUGCC" at the 3' end of the random region. Because of the positioning of this sequence, it is expected that it forms a structure with the 3' fixed region.

Computer-assisted RNA folding studies suggest a common structural motif. About half of the sequences studied (19/39) are capable of forming a perfect (i.e., without bulges or internal loops) hairpin at the 5' end of the random region, immediately 3' to the splint helix, or separated from the splint helix by a U (5/19). The stems of these potential hairpins range in length from 4 to 9 base-pairs, with 7 base-pairs being the most common length. There is no apparent sequence conservation in the stem. The loops of these hairpins range in size from 4 to 7 bases, with no apparent sequence conservation. The conserved position of these hairpins suggest they form a coaxial stack on the splint helix.

Most of the computer-generated foldings suggest base-pairing with the 5' end of the splint DNA. The formation of some structure in this region is to be expected, since it contains the active-site reagent. However, the likelihood of finding a 3-base complement to the 5' sequence (i.e. GRY) within a 40 nt random region by chance is high, and so the significance of the pairings generated is problematic. There are two types of evidence for some interaction with this region. The 5' end of the DNA is protected from digestion by S1 nuclease by several of the selected RNAs, as compared to the unselected pool. Second, removing the valyl phosphonate from the splint oligo reduces the $T_M$ of RNA 10.14 by 3° C. This indicates an interaction between the valyl phosphonate and RNA that stabilizes the RNA secondary or tertiary structure.

Activity Assays

Protease Inhibition Assay

A colorimetric assay was used to monitor the peptide hydrolysis activity of human neutrophil elastase. 34 of the selected RNAs were surveyed for hNE inhibitory activity using the peptide hydrolysis assay. An excess of RNA:splint DNA hybrid, at a series of concentrations is added to hNE, and hydrolysis of a chromogenic peptide is monitored by absorbance at 405 nm. The slope of the plot of $A_{405}$ vs. time represents elastase activity. As the inhibitor reacts with hNE over time, the slope approaches 0.

The concentrations of the reactants were: N-methoxysuccinyl-Ala-Ala-Pro-Val-p-nitroanilide (AAPV-NA, Sigma), 200 or 300 $\mu$M; hNE, 2–5 nM; RNA, 10-250 nM; N-Boc-valine phosphonate diphenyl ester, 2–50 $\mu$M. The reactions were buffered with Hank's buffered saline (Sigma) plus 20 mM Tris pH7.5 and 0.01% human serum albumin (Sigma). Reaction volumes were 200 or 300 $\mu$L. Reactions were mixed in polystyrene 96-well microtiter plates, and monitored at 405 nm in a BioTek EL312e microtiter plate reader at 37° C. After a 2 minute delay, readings were taken every minute for 30 minutes. A plot of $A_{405}$ vs. time was fitted to equation (1) (Kaleidagraph, Synergy Software).

$$A_{405} = v_0(1 - e^{[k_{obs}t]}) + A_t \quad (1)$$

$v_0$ is the steady-state rate of peptide hydrolysis by elastase, $k_{obs}$ is the observed rate of inactivation of elastase by inhibitor, and $A_t$ is a displacement factor which corrects for the delay between the reaction start and data collection. The second-order rate constant for inhibition, $k_{obs}/[I]$, was obtained from the slope of a replot of $k_{obs}$ vs. inhibitor concentration. $V_{max}$ and $K_M$ values for peptide hydrolysis were obtained from plots of $v_0$ vs. [AAPV-NA], fitted to equation (2)

$$v_0 = \frac{V_{max}[AAPV \cdot NA]}{K_M + [AAPV \cdot NA]} \quad (2)$$

Thrombin and cathepsin G inhibition were measured by a similar assay. Thrombin (Enzyme Research, Inc.) was at 0.5 nM, and its substrate, S-2238, was at 75 $\mu$M. Cathepsin G (Calbiochem) was at 40 nM, and its substrate, N-methoxysuccinyl-Ala-Ala-Pro-Phe-p-nitroanilide (Sigma) was at 200 $\mu$M.

Preparation of Human Neutrophils 25 ml of blood from volunteers was withdrawn into EDTA-treated vacuum tubes. This blood was immediately layered on a double-density gradient of 15 ml Histopaque (Sigma) 1.119 g/ml and 10 ml 1.077 g/ml in a 50 ml Falcon disposable conical tube. The tube was centrifuged for 30 minutes at 2000 g in a Beckman TJ-6 centrifuge at room temperature. Granulocytes, which are >80% neutrophils, are held up at the interface between the two layers of Histopaque. This layer was withdrawn and washed three times in 25 ml HBSS by centrifugation at 700 g for 10 minutes at room temperature. Between washes, contaminating red blood cells were lysed by resuspending the cell pellet in 5 ml cold distilled water, and vortexing for 30 seconds, after which 25 ml HBSS was added, and the cells pelleted. Live cells were counted by trypan blue exclusion in a hemocytometer.

Elastase activity was determined by adding $10^5$–$10^6$ cells to a well of a microtiter plate in 0.3 ml HBSS, inducing with 0.1 $\mu$g/ml phorbol myristyl acetate (Sigma), and monitoring AAPV-NA hydrolysis as described above. The results of this assay are provided in Table V.

Denaturing Gel Assay

The covalent reaction between elastase and the splint DNA was assayed by denaturing gel electrophoresis. The splint oligo, modified with the valine phosphonate, was 3' end-labelled using terminal deoxynucleotidyl transferase and $\alpha$-$^{32}$P cordycepin (New England Nuclear). The labelled splint oligo and RNA were mixed and annealed as described above, and the reaction was initiated by adding a $\geq$five-fold excess of hNE. Reactions were at 37C. for 10–60 seconds. 2–5 time points were taken for each elastase concentration. The reaction was quenched by addition of an aliquot to 2.5 volumes of 0.1M MES pH6.3/10M urea/1% SDS at 50 C. The elastase-oligo conjugate was resolved from the free oligo by denaturing electrophoresis in a TBE/7M urea/ 0.05% SDS polyacrylamide gel. A Fuji Phosphor Imager was used to visualize dried gels, and quantify the conjugated and free oligo.

$k_{obs}$ for each elastase concentration was calculated by linear regression of a plot of $\ln(S_t/S_0)$ vs. time, where $S_t$ is the amount of free oligo remaining at a given time, and $S_0$ is the total amount of reactive oligo. $S_0$ is calculated as the maximum extent of the reaction from an extended time course at high elastase concentration. The extent varied between 0.42 and 0.45 of total oligo. Because the valine phosphonate used was a racemate, and the elastase active site is specific for (L)-valine, a maximum extent of 0.5 is expected. The kinetic constants $k_{cat}$ and $K_M$ for the covalent reaction of oligo with hNE were obtained by replotting $k_{obs}$ vs. [hNE], and fitting to equation (2).

EXAMPLE 3

Splint SELEX to Identify Additional Elastase Inhibitors

Highly potent and specific inhibitors of human neutrophil elastase were produced by an approach similar to that used in Example 2. The splint SELEX process was performed by preparing a standard SELEX candidate mixture and a single compound containing a valyl phosphonate functional unit attached to a nucleic acid sequence that hybridizes to a portion of the fixed region of the candidate mixture of nucleic acid sequences. In this example two sets of selections were performed. The first used purified human neutrophil elastase to obtain nucleic acid ligands from DNA and 2' NH$_2$-pyrimidine RNA libraries. The second used activated human neutrophils as the source of elastase and the obtained nucleic acid ligands were DNA.

Synthesis of the Human Neutrophil Elastase Chiral Co-ligand

The valyl phosphonate functional unit that was attached via the Splint SELEX method to each of the nucleic acid libraries was prepared as follows. The Cbz derivative of racemic 1-amino-2-methylpropane-phosphonous acid was resolved as its chiral salt with (−)-α-methylbenzylamine ((+)-salt) to give the (+)-enantiomer and with (+)-α-methylbenzylamine ((−)-salt) to give the (−)-enantiomer. After five rounds of recrystallization the optical rotations and melting points of the salts had converged to constant values. The salts were converted to the free phosphonous acids R-(+)-4a and S-(−)-4b (Scheme 2).

The subsequent oxidation 4a–b proceeded in high yield upon treat with bromine in aqueous sodium hydroxide solution to give the corresponding phosphonic acids 5a–b. Esterification of 5a–b to the diphenyl esters 6a–b was achieved using diphenylsulfinate in pyridine at 60° C. It was found to be more efficient to convert crude 6a–b directly to the hydrobromide salt of 7a–b with 30% hydrogen bromide in acetic acid which allowed isolation of the salt by precipitation from ether. The salt was then converted to the free base 7a–b with ammonia in ether. Treatment of 7a–b with disuccinimidylcarbonate in acetonitrile resulted in quantitative conversion to the desired carbamates R-(+)-8a and S-(−)-8b. The experimental procedures utilized for these conversions were similar to those described in Example 2.

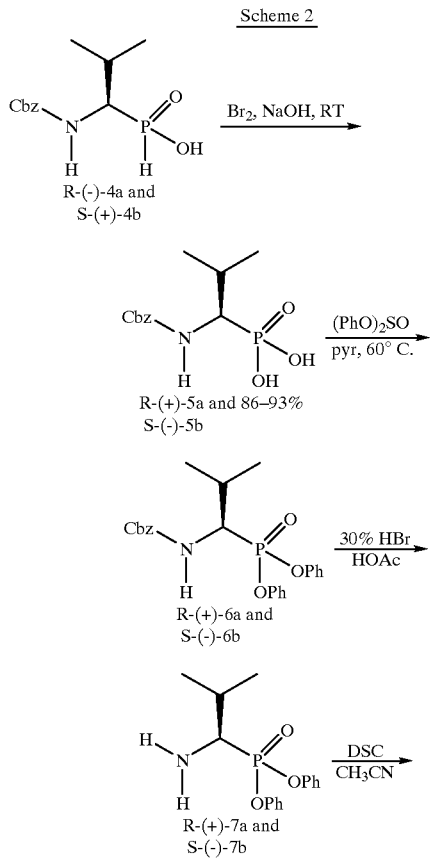

Scheme 2

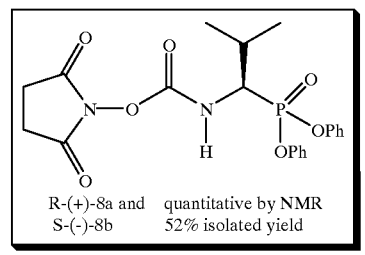

R-(+)-8a and  quantitative by NMR
S-(−)-8b     52% isolated yield

Ligand Selection

The valyl phosphonate was activated via an NHS ester. This compound was coupled to the 5' hexyl amine linker of a 16-mer DNA oligo complementary to the 5'-fixed region of 40N7.1(SEQ ID NO: 38)) candidate mixture.

Two sets of selections were performed: one used activated human neutrophils as the source of elastase, the other used purified human neutrophil elastase. DNA was used as the nucleic acid in the former selection; DNA and 2' NH$_2$-pyrimidine RNA libraries were used in the latter.

Selection Using Purified Elastase:

Synthesis of the starting RNA pool used 50 pmol of 40N7.1DNA (SEQ ID NO: 38) as template. This DNA was produced by PCR amplification from 10 pmol of synthetic DNA. The transcription buffer is 80 mM HEPES pH 7.5, 12 mM MgCl$_2$, 2 mM spermidine, 40 mM DTT, 3 mM guanosine, 0.5 mM GTP, 2 mM ATP, 2 mM each uridine- and cytosine-2'-amino nucleoside triphosphate, 0.01 unit/μl inorganic pyrophosphatase (Sigma), ~0.5 μM T7 RNA polymerase. Transcription was at 37° C. for 10–14 hrs. Full-length transcripts were purified by electrophoresis on an 8% acrylamide/7M urea TBE-buffered polyacrylamide gel.

The starting DNA pool consisted of synthetic 40N7.1 DNA (SEQ ID NO: 38). Subsequent rounds of ssDNA were produced by PCR as described below. The template strand from the PCR is primed by a biotin-containing oligo 3N7.1 (BioBioBioBio-TCCCGCTC GTCGTCTG (SEQ ID NO: 103)). This strand is retarded relative to the ligand strand during denaturing polyacrylamide gel electrophoresis, allowing the ligand strand to be purified as a ssDNA.

Purified DNA or RNA was mixed with a 1.1-fold excess of splint DNA, and annealed by heating to 65° C. followed by cooling to 35° C. over 5 min. This hybrid was mixed with hNE (Calbiochem) at a 5- to 20-fold excess of DNA or RNA in Hank's Buffered Saline Solution (Sigma) supplemented with 25 mM HEPES pH7.5 and 100 mM NaCl, and allowed to react for 5–15 minutes at 37° C. The high salt concentration was used to increase the stringency of the hNE-nucleic acid interaction, and reduce the electrostatic component of this interaction. Soluble elastin (Elastin Products Co.) was used as a competitor at increasing concentrations from rounds 8–18, to further increase the stringency of the selection. The reaction was quenched by addition of sodium dodecyl sulfate (SDS) to 0.1%. Volumes less than 200 μl were loaded directly on a 4% polyacrylamide gel with SDS added to 0.025%, and buffered with TBE. Larger volumes were concentrated by ultrafiltration through a Centripor 50 K MWCO filter cartridge centrifuged at 3000×g at 10° C., then loaded on the gel. The gel was run at 300V for 2 hr, and the bands of conjugated and unconjugated DNA or RNA were visualized by autoradiography. The band corresponding to the DNA or RNA:splint DNA:hNE complex was excised, crushed, and eluted in a 0.1% SDS for 30 minutes. The eluate was recovered by centrifugation through Spin-X 0.45 μm cellulose acetate microcentrifuge filter cartridges. The DNA or RNA was then ethanol precipitated and resuspended in 50 μl H$_2$O. The DNA could be used directly and the RNA was reversed transcribed before PCR.

To the 50 μl RNA, 6 μl of 10×RT buffer (1×=50 mM HEPES pH7.5/50 mM NaCl/10 mM MgCl$_2$/5 mM DTT), 100 pmol each of the 5' and 3' primers, and 0.67 mM each dNTP were added. The mixture was heated to 65° C., then cooled to 35° C. over 5 minutes. The reaction was initiated by addition of 40 units AMV reverse transcriptase (Life Sciences), and incubation continued at 35° C. for 5 minutes. The temperature was then raised by 2° C. per minute for 15 minutes to 65° C. At 52–55° C., another 40 units of reverse transcriptase was added.

The polymerase chain reaction was initiated by adding 40 μl 10×Stoffel buffer (1×=10 mM Tris pH 8.1, 3 mM MgCl$_2$, 10 mM KCl, 0.05% NP-40), 40 μl 40% acetamide, 500 pmol 5N7.1C (GGGAGGACGATGCGG (SEQ ID NO: 104)) (DNA SELEX) or 5N7.1 (TAATACGACTCACTATAGGGAGGACGATGCGG (SEQ ID NO: 105)) (RNA SELEX), 500 pmol 3N7.1bio (SEQ ID NO: 103) (DNA SELEX) or 3N7.1 (TCCCGCTC GTCGTCTG (SEQ ID NO: 106)) (RNA SELEX), dNTP to 1 mM, and 4 U of the Stoffel fragment of Taq DNA polymerase (Perkin Elmer). 16 cycles were carried out of 92° C./30 sec→62° C./(20+n×10) sec (where n is the cycle number)→72° C./40 sec. The DNA was ethanol precipitated and resuspended in 100 μl H$_2$O. 10 μl of this reaction was used as a transcription template in the next round of SELEX in the RNA SELEX, or directly in the DNA SELEX.

A bias against sequences which include the 3' fixed region as part of the core structure was introduced in rounds 16–18 by "dirty" PCR. This method consisted of PCR using the primer "3N7.1D" (TCC(C/D)(G/H)(C/D)(T/V)(C/D)(G/H) (T/V)(C/D) (G/H)(T/V)CTG (SEQ ID NO: 107)) in the reaction. This primer is a derivative of 3N7.1, with the difference that the central 10 nucleotides were synthesized as 79% mol fraction of the parental sequence, and 7% each of the other three nucleotides. PCR with this primer is expected to introduce mutations into the 3' fixed region at a frequency of 1−(0.79$^{10}$)=0.91. Ligands which rely on a specific 3' fixed sequence should be rendered less active by these mutations, and so be selected against.

Eighteen cycles of SELEXion were carried out using this protocol.

ssDNA SELEX To Human Neutrophil Elastase Induced From Human Neutrophils

A round of SELEX consisted of purifying human neutrophils and then inducing them at 37° C. for 10 minutes, followed by a binding reaction at 37° C. with splint-annealed ssDNA (and soluble elastin as a competitor). Reactions were transferred to CoStar Spin X tubes, spun gently then loaded onto gels. Gel shifted ssDNA was extracted from gels using the freeze/squeeze method. PCR was performed using TAQ polymerase and a triple biotinylated primer for ssDNA (SEQ ID NO: 103) separation on denaturing gel. Pure ssDNA was then kinased and annealed to DNA-val-P splint in a 1.2× splint excess.

Neutrophils were prepared as follows. 15–20 mls of blood was obtained from healthy volunteers. Neutrophils were purified by layering blood over a gradient consisting of 2 layers of polysucrose/sodium diatrizoate (Sigma:Histopaque 1077,1119). Neutrophils were counted and assayed for elastase activity by induction with 3 uM phorbal myristate acid and 10 uM A23187 Ca+ ionophore. Activity ranged from 10–27 pmol of hNE per 10$^6$ cells.

Next, 15 rounds of the SELEX process were performed starting with 90 pmol of 40N7.1 ssDNA (SEQ ID NO: 38). All rounds were performed with 25–90 pmol of splint-ssDNA in a 40 to 200 fold ssDNA-splint excess over protein. An appropriate number of freshly prepared neutrophils were used to produce 2.4–0.25 pmol of hNE upon induction. Binding times ranged from 5 min at the beginning rounds to 2 min at later rounds in volumes of 75–100 ul. Elastin was added in Rounds 9–15 at 0.24 mg/ml–1 mg/ml to increase stringency by providing a competitor. To reduce background problems at rounds 8, 11 and 14, splint-ssDNA was run in the absence of hNE and nonshifting ssDNA was purified for further rounds of the SELEX process. Gel shifts were run at 450 volts with conditions ranging from 1×TBE, 0.05% SDS, 4% 19:1 acrylamide @ 22° C. with a fan to 1.5×TBE, 0.05% SDS, 6% 19:1 acrylamide @ 4° C.

Sequence/Structure of Ligands

The sequences of the nucleic acid portion of the nucleic acid ligands to human elastase were determined by standard procedures and are presented in Table VI. The regions believed to be evolved random regions are shown in capital letters and the regions believed to be derived from the originally fixed sequences of SEQ ID NO: 38 are shown in lower case letters.

The sequences of 50 DNAs from the round 18 pool of the high-salt SELEX were determined as shown in Table VI. The sequences are identified by the DD in the ligand name (SEQ ID NO: 108–157). All of these are unique sequences.

The sequence of 29 RNA clones from the round 18 pool of the high-salt SELEX were determined as shown in Table VI. The sequences are identified by the DR in the ligand name (SEQ ID NO: 158–186).

The sequence of 64 DNA clones from the round 15 pool of the activated neutrophil SELEX were determined. These clones represent 38 unique sequences as shown in Table VI. The sequences are identified by the ED in the ligand name (SEQ ID NO: 187–224).

Activity Assays

Protease Inhibition Assay

A fluorometric assay was used to monitor inhibition of the peptide hydrolysis activity of human neutrophil elastase. 25 of the selected DNAs were surveyed for hNE inhibitory activity using the peptide hydrolysis assay. An excess of DNA:splint DNA hybrid, at a series of concentrations is added to hNE, and hydrolysis of a fluorogenic peptide is monitored. The slope of the plot of fluorescence vs. time represents elastase activity. As the inhibitor reacts with hNE over time, the slope approaches 0.

The concentrations of the reactants were: N-methoxysuccinyl-Ala-Ala-Pro-Val-p-aminomethylcoumarin (AAPV-AMC, Enzyme Systems Products), 500 μM ; hNE, 0.3 nM; DNA, 0.4–3 nM. The reactions were buffered with Hank's buffered saline (Sigma) plus 20 mM Tris pH7.5 and 0.01% human serum albumin (Sigma). Reaction volumes were 200 or 300 μL. Reactions were mixed in polystyrene 96-well microtiter plates, and monitored in a CytoFluor II fluorescence multiwell plate reader (PerSeptive BioSystems) at room temperature. Readings were taken every minute for 30 minutes. A plot of fluorescence units vs. time was fitted to equation (3) (Kaleidagraph, Synergy Software).

$$FU = v_0(1 - e^{(-k_{inact\ obs}t)}/k_{inact\ obs}) + F_t \quad (3)$$

$v_0$ is the steady-state rate of peptide hydrolysis by elastase, $k_{inact\ obs}$ is the observed rate of inactivation of elastase by inhibitor, and $F_t$ is a displacement factor which corrects for the delay between the reaction start and data collection. The second-order rate constant for inhibition, $k_{inact}/K_I$, was obtained from the slope of a replot of $k_{inact\ obs}$ vs. inhibitor concentration. This apparent rate constant was corrected for competition of the peptide substrate vs. the inhibitor by multiplying by the factor $[S]/([S]+K_M)$, where $K_M$ is Michaelian constant of AAPV-AMC, measured to be 100 $\mu$M. The assay was conducted as described in Example 2. The results of this assay are shown in Table VII.

EXAMPLE 4

Nucleic Acid Ligands That Bind to HIV-1 Rev Protein

A target protein chosen to illustrate photo-SELEX process described in copending WO95/08003, filed Sep. 16, 1994, which is herein incorporated by reference was the Rev protein from HIV-1. The example provided herein describes that ligands were identified which bound covalently to the Rev protein both with and without irradiation.

Rev's activity in vivo is derived from its association with the Rev-responsive element (RRE), a highly structured region in the HIV-1 viral RNA. Previous RNA SELEX experiments of Rev have allowed the isolation of very high affinity RNA ligands. The highest affinity ligand, known as "Rev 6a," (SEQ ID NO:225) has a $K_d$ of approximately 1 nM. The sequence of Rev 6a is GGGUGCAUUGAGAAA-CACGUUUGUGGACUCUGUAUCU (SEQ ID NO: 225). The secondary structure of 6a, and its interaction with Rev, have been well characterized.

The construction of the nucleic acid test mixture for photo-SELEX was based upon the Rev 6a sequence (SEQ ID NO:225). During the synthesis of the deoxyoligonucle-otide templates for SELEX, the random region of the template was substituted by a "biased randomization" region, in which the ratio of the four input bases was biased in favor of the corresponding base in the Rev 6a sequence. (Actual ratios were 62.5:12.5:12.5:12.5.) For example, if the Rev 6a base for a particular position is G, then the base input mixture for this synthesis step is 62.5% G, and 12.5% of the other three bases. The photoreactive uracil analogue 5-iodouracil (iU), which has been used to generate high-yield, region-specific crosslinks between singly-substituted iU nucleic acids and protein targets (Willis et al. (1993) Science 262:1255) was used for this example. In this case, the 5-iodo acts as a functional unit. This "biased randomization" nucleic acid test mixture contains approximately $10^{14}$ unique sequences. This template was used for in vitro T7 transcription with 5-iUTP to generate fully-substituted iU RNA for selection.

The iU chromophore is reactive under long-wavelength ultraviolet radiation, and may photocouple to the aromatic amino acids of protein targets by the same mechanism as 5-bromouracil (Dietz et al. (1987) J. Am. Chem. Soc. 109:1793). As discussed above, the target for this study is the HIV-1 Rev protein, which is necessary for productive infection of the virus (Feinberg et al. (1986) Cell 46:807) and the expression of the viral structural genes gag, pol and env (Emerman et al. (1989) Cell 57:1155). The interaction of Rev with high affinity RNA ligands is well characterized. A single, high-affinity site within the RRE (the IIB stem) has been identified (Heaphy et al. (1991) Proc. Natl. Acad. Sci. U.S.A. 88:7366). In vitro genetic selection experiments have generated RNA ligands that bind with high affinity to Rev and have helped determine the RNA structural elements necessary for Rev:RNA interactions (Bartel et al. (1991) Cell 67:529; Tuerk et al., *In The Polymerase Chain Reaction* (1994) pp. 233–243; Jensen et al. (1994) J. Mol. Biol. 235:237).

The SELEX procedure alternated between affinity selection for Rev using nitrocellulose partitioning and monochromatic UV irradiation of the nucleoprotein complexes with denaturing polyacrylamide gel partitioning of the crosslinked complexes away from non-crosslinked RNA sequences. The final procedure utilized a simultaneous selection for affinity and crosslinking using competitor tRNA. Each round constitutes a selection followed by the conversion of recovered RNA to cDNA, polymerase chain reaction (PCR) amplification of the DNA, and in vitro transcription to generate a new pool of iU-RNA. To amplify RNA's recovered as covalent nucleoprotein complexes, the appropriate gel slice was isolated and proteinase K treated.

The RNA pool was first subjected to three rounds of affinity selection with Rev protein, with partitioning of the higher affinity sequences by nitrocellulose filters. Next, the evolving RNA pool was subjected to UV laser irradiation in the presence of excess Rev protein to allow those RNA sequences with the ability to crosslink with the protein to do so. Crosslinked RNA sequences were then partitioned using polyacrylamide gel electrophoresis (PAGE). These crosslinked RNAs were recovered from the gel material, the linked Rev protein digested away, and the RNAs used for cDNA synthesis and further amplification for the next round of photo-SELEX. A 308 nm XeCl excimer laser was used for the first round of photocrosslinking; thereafter, a 325 nm HeCd laser was employed.

Following four rounds of selection for laser-induced crosslinking, the RNA pool was again put through three rounds of affinity selection. Finally, the RNA pool was selected simultaneously for its ability to bind Rev with high affinity and to crosslink to the protein. This was accomplished by using high concentrations of a non-specific nucleic acid competitor in the photocrosslinking reaction.

Crosslinked product increased approximately 30-fold from the starting pool to round 13. Under these conditions, the greatest increase in crosslinking is correlated with the greatest increase in affinity -from round 7 to round 10.

After 13 rounds of selection, the PCR products were cloned and 52 isolates sequenced and described in copending WO95/08003. Several of the ligands isolated by this procedure were able to form a stable complex with the target protein resistant to denaturing gel electrophoresis in the absense of UV irradiation. One of these ligands was termed Trunc24 (SEQ ID NO: 226) and has the sequence GGG-GAUUAACAGGCACACCUGUUAACCCU.

Trunc24 (SEQ ID NO:226) photo-independent crosslinking with HIV-1 Rev in the presence of human nuclear extracts was determined as follows: Trunc24 RNA, nuclear extracts, and Rev protein were combined and incubated on ice for 10 min. Samples were mixed 1:1 with 8M urea loading buffer and placed on a 7M urea, 8% polyacrylamide gel for analysis. The experiment showed that the ligand covalently bound to the target protein without photo-crosslinking.

TABLE 1

| Temp. (°C.) | 37 | 30 | 30 | 24 | 24 | 20 | 0 | 0 | 0 | 0 | 0 | 0 |
|---|---|---|---|---|---|---|---|---|---|---|---|---|
| Reaction time (s) | 60 | 60 | 30 | 60 | 30 | 30 | 60 | 60 | 120 | 60 | 30 | 60 |
| [RNA] ($\mu$M) | 40 | 40 | 40 | 40 | 40 | 40 | 20 | 20 | 20 | 20 | 20 | 20 |
| % RNA reacted | 1.3 | 0.7 | 0.8 | 0.7 | 1.9 | 2.5 | 1.2 | 3.4 | 4.5 | 5.0 | 2.5 | 2.8 |
| Background ratio | 3.2 | 3.2 | 3.4 | 1.7 | 2.5 | 3.9 | 3.1 | 4.0 | 4.9 | 10.1 | 9.0 | 4.5 |

TABLE II

| SEQ ID NO | LIGAND # | 30N REGION | FREQ | $K_{obs}$ (s$^{-1}$) |
|---|---|---|---|---|
| CLASS I: | | | | |
| 2 | 12.48 | GGGAGCUCAGAAUAAACGCUCAA CUCCCCCGUGCUGCCUUAGCGCGUAGUUCG UUCGACAUGAGGCCCGGAUCCGGC | 1 | |
| 3 | 12.16 | GGGAGCUCAGAAUAAACGCUCAA CUCCCCGUUAGCGCCUCACUGACGUGUCGA UUCGACAUGAGGCCCGGAUCCGGC | 4 | 1.34e$^{-3}$, 1.4e$^{-3}$ |
| 4 | 10.25 | GGGAGCUCAGAAUAAACGCUCAA CUGAGUCAUGCGGCAGCUCCCCGCCACGC UUCGACAUGAGGCCCGGAUCCGGC | 1 | |
| 5 | 12.2 | GGGAGCUCAGAAUAAACGCUCAA UGCCUUGUUCUUUUACUCCCCCGACGCCUC UUCGACAUGAGGCCCGGAUCCGGC | 2 | |
| 6 | 10.28 | GGGAGCUCAGAAUAAACGCUCAA CGUUUAGGACUCCCCCGUUCGUCGAGCGAA UUCGACAUGAGGCCCGGAUCCGGC | 2 | 1.8e$^{-3}$ |
| 7 | 12.19 | GGGAGCUCAGAAUAAACGCUCAA CGUUUAGGUCUCCCCCGUCCGUCGAGCGAA UUCGACAUGAGGCCCGGAUCCGGC | 1 | |
| 8 | 12.25 | GGGAGCUCAGAAUAAACGCUCAA CUGCGUUACUCCCCCGGACAACUGUUCGUUAUUCGACAUGAGGCCCGGAUCCGGC | 1 | |
| 9 | 12.8 | GGGAGCUCAGAAUAAACGCUCAA UCUUCGUGUUCCCCGUGCUGUGUCGUCACG UUCGACAUGAGGCCCGGAUCCGGC | 2 | |
| 10 | 12.14 | GGGAGCUCAGAAUAAACGCUCAA ACGUCAUUCCGAGUCGGGUUCGUUCCCCGC UUCGACAUGAGGCCCGGAUCCGGC | 1 | 1.7e$^{-3}$ |
| 11 | 12.47 | GGGAGCUCAGAAUAAACGCUCAA UGUGUGAGUGGAUCCGUUCCCCGCCUGGUG UUCGACAUGAGGCCCGGAUCCGGC | 1 | 1.49e$^{-3}$ |
| CLASS II | | | | |
| 12 | 10.19 | GGGAGCUCAGAAUAAACGCUCAA UGGACACAACUCCGUUAUCUCGCUCUCAGC UUCGACAUGAGGCCCGGAUCCGGC | 1 | |
| 13 | 10.21 | GGGAGCUCAGAAUAAACGCUCAA UGAACACAACUUCAUAUCUCGGGACUCACAGUUCGACAUGAGGCCCGGAUCCGGC | 1 | |
| 14 | 12.31 | GGGAGCUCAGAAUAAACGCUCAA UCGACACAACUCGAUCUCCGUGGCUGUCAC UUCGACAUGAGGCCCGGAUCCGGC | 2 | 8.9e$^{-4}$, 1.5e$^{-3}$ |
| 15 | 12.23 | GGGAGCUCAGAAUAAACGCUCAA UCGACACAACUCGAUCUCCGUGUCUGUCAC UUCGACAUGAGGCCCGGAUCCGGC | 1 | |
| 16 | 12.46 | GGGAGCUCAGAAUAAACGCUCAA UGGACACAACUCCAUUCAUCCCGGGACCGCUGUUCGACAUGAGGCCCGGAUCCGGC | 1 | 6.7e$^{-4}$ |
| 17 | 12.28 | GGGAGCUCAGAAUAAACGCUCAA UGGUCACAACUCCAUUAGCUGAGGCCCGUG UUCGACAUGAGGCCCGGAUCCGGC | 1 | |
| 18 | 12.41 | GGGAGCUCAGAAUAAACGCUCAA GCGACACAACUCGAUCUCCGUGGCUGUCAC UUCGACAUGAGGCCCGGAUCCGGC | 1 | |
| 19 | 12.40 | GGGAGCUCAGAAUAAACGCUCAA GUCUCACAACUGGCUUAUCCGGUGCGCACG UUCGACAUGAGGCCCGGAUCCGGC | 1 | 1.4e$^{-3}$, 1.9e$^{-3}$ |
| 20 | 12.21 | GGGAGCUCAGAAUAAACGCUCAA GCCACACAACUGGCUUAUCCUGAACGCGGC UUCGACAUGAGGCCCGGAUCCGGC | 1 | |
| 21 | 12.32 | GGGAGCUCAGAAUAAACGCUCAA CCAUCACAACUUGGUUAUCCGGUACUCUGUGUUCGACAUGAGGCCCGGAUCCGGC | 1 | |
| 22 | 12.39 | GGGAGCUCAGAAUAAACGCUCAA CAUCACAACUUGUUAUCCGCUUCACCGCUC UUCGACAUGAGGCCCGGAUCCGGC | 1 | |
| 23 | 12.3 | GGGAGCUCAGAAUAAACGCUCAA CAUCACAACUUGUUGUCCUGGUCGAUGCC UUCGACAUGAGGCCCGGAUCCGGC | 3 | 7.5e$^{-4}$ |
| 24 | 10.26 | GGGAGCUCAGAAUAAACGCUCAA CAUCACAACUUGUUGUCCCGGUACUUGUGU UUCGACAUGAGGCCCGGAUCCGGC | 1 | |
| 25 | 10.23 | GGGAGCUCAGAAUAAACGCUCAA UGUCACAACUCAUUGUUCGGGAAUUGUGCCAUUCGACAUGAGGCCCGGAUCCGGC | 1 | |
| 26 | 12.24 | GGGAGCUCAGAAUAAACGCUCAA CGUCAGCGGAUCUCCAUUGCGUUAUACGGG UUCGACAUGAGGCCCGGAUCCGGC | 1 | 1.44e$^{-3}$ |
| 27 | 12.4 | GGGAGCUCAGAAUAAACGCUCAA CGAAUCAAUGCGCGGAUCUCAGGAUAUUCG UUCGACAUGAGGCCCGGAUCCGGC | 5 | 1.7e$^{-3}$ |
| 28 | 12.6 | GGGAGCUCAGAAUAAACGCUCAA GCGGUAACAUGCUGGAUCUCAGGAAACCGC UUCGACAUGAGGCCCGGAUCCGGC | 3 | 2.2e$^{-3}$ |
| 29 | 12.45 | GGGAGCUCAGAAUAAACGCUCAA GCGGUAACAUGCUGGAUCUCAGGAAACCGU UUCGACAUGAGGCCCGGAUCCGGC | 1 | 5.1e$^{-3}$ |
| 30 | 12.22 | GGGAGCUCAGAAUAAACGCUCAA UGCCACUUUUGUUCGGAUCUUAGGAAGGCA UUCGACAUGAGGCCCGGAUCCGGC | 1 | 1.2e$^{-3}$ |
| 31 | 12.42 | GGGAGCUCAGAAUAAACGCUCAA UCAUCAUUUGUACCGGAUCUCAGUGUGAUG UUCGACAUGAGGCCCGGAUCCGGC | 1 | |

TABLE II-continued

| SEQ ID NO | LIGAND # | 30N REGION | FREQ | $K_{obs}$ $(s^{-1})$ |
|---|---|---|---|---|
| 32 | 10.24 | GGGAGCUCAGAAUAAACGCUCAA AGCUGUUGGCAGCCCGGAUCUACGCAUGGGAUUCGACAUGAGGCCCGGAUCCGGC | 1 | |
| 33 | 12.1 | GGGAGCUCAGAAUAAACGCUCAA AGCUGUUGGCAGCGCUGGUGAAGGGAUAGGCUUCGACAUGAGGCCCGGAUCCGGC | 6 | $3.0e^{-4}$, $2.6e^{-3}$ |
| CLASS III | | | | |
| 34 | 12.17 | GGGAGCUCAGAAUAAACGCUCAA UGAGAACUCCGUGAUUGAGUCAGGUACGCGCUUCGACAUGAGGCCCGGAUCCGGC | 1 | |
| 35 | 12.30 | GGGAGCUCAGAAUAAACGCUCAA UCCGUGUUGCCACUCCAGUUACUGGACGCC UUCGACAUGAGGCCCGGAUCCGGC | 1 | $5.4e^{-4}$, $9.4e^{-4}$ |
| 36 | 12.9 | GGGAGCUCAGAAUAAACGCUCAA GUGGAGCUUCGUGACUUGGUCGGAGCCGUG UUCGACAUGAGGCCCGGAUCCGGC | 1 | $1.28e^{-3}$ |
| 37 | 12.35 | GGGAGCUCAGAAUAAACGCUCAA UCGUGUCGCCACCAGCCUUUCUCGUGCGCC UUCGACAUGAGGCCCGGAUCCGGC | 1 | |

TABLE III

| GMPS substrate | BrAc substrate | $k_{cat}$ (sec$^{-1}$) | $K_m$ (M) | $k_{cat}/K_m$ (M$^{-1}$ sec$^{-1}$) |
|---|---|---|---|---|
| 30N1 | BrBK | $2.1 \pm 0.4 \times 10^{-4}$ | $1.3 \pm 0.3 \times 10^{-2}$ | $1.6 \times 10^{-2}$ |
| reactant 12.1 | BrBK | $1.4 \pm 0.1 \times 10^{-2}$ | $1.3 \pm 0.3 \times 10^{-4}$ | $1.1 \times 10^{2}$ |
| 30N1 | BrAcNH$_2$ | — | — | — |
| reactant 12.1 | BrAcNH$_2$ | $1.1 \pm 0.1 \times 10^{-4}$ | $2.1 \pm 0.3 \times 10^{-2}$ | $5.2 \times 10^{-3}$ |

TABLE IV

SPLINT-ELASTASE LIGANDS

| SEQ ID No | LIGAND | SEQUENCE |
|---|---|---|
| 39 | 10.1 | gggaggacgaugcggCAUGAUCUAGGUAAAGACAUAUCACUAACCUGAUUGUGCCcagacgacgagcggga |
| 40 | 10.2 | gggaggacgaugcggCAGUAAUCUUUGGUAUCAAGAUUACUGGGAUGUCCGUGCCcagacgacgagcggga |
| 41 | 10.3 | gggaggacgaugcggCAGUAAUCUUUGGUAUCAAGAUUACUGGGAUGUGCGUGCCcagacgacgagcggga |
| 42 | 10.4 | gggaggacgaugcggCAAACCAUCUAAGCUGUGAUAUGACUCCUAAGACAGUGCCcagacgacgagcggga |
| 43 | 10.6 | gggaggacgaugcggCAUCGUCAAUGUAGUAGUACUACGUAAGUCACGUGGUCCCcagacgacgagcggga |
| 44 | 10.7 | gggaggacgaugcggCGAUAAUCUUGGUAUCAAGAUUACUGGGAUGUCGCGUGCCcagacgacgagcggga |
| 45 | 10.8 | gggaggacgaugcggCAUAUCUACAUGUAGGUCCUAAUCGAAAUCCAGUUGUGCCcagacgacgagcggga |
| 46 | 10.10 | gggaggacgaugcggCAUUAGUCCGUAGCAUAGCACUAUCUAAACCAGUUGGGGAcagacgacgagcggga |
| 47 | 10.11 | gggaggacgaugcggCUACAUAGGUUAAGAUUACCUAACCGAAUUAACAUGCAGCcagacgacgagcggga |
| 48 | 10.13 | gggaggacgaugcggUAAGUUACUACCGAUACAACCGAAGUCCUCUACCCGUGGcagacgacgagcggga |
| 49 | 10.14 | gggaggacgaugcggCAUUACUAAGAUUAACAGCUUAGUAUAACAGCCUCCUGUGcagacgacgagcggga |
| 50 | 10.16 | gggaggacgaugcggCACGUACAGUCUAAAAGUGUGUUAGUGUAGCGGUGGUGUGcagacgacgagcggga |
| 51 | 10.17 | gggaggacgaugcggCAGUAGCAAUAAGACUACUGUAGGGUUGAAUCCGUGCUGcagacgacgagcggga |
| 52 | 10.18 | gggaggacgaugcggCAUUACUAAGAUUAACAGCUUAGUAUAACAGCCUCCUGUGcagacgacgagcggga |
| 53 | 10.19 | gggaggacgaugcggUGCAUGCGUACCAGUAUCCUAAAACUAAACCUAGCGUGCCCcagacgacgagcggga |

TABLE IV-continued

SPLINT-ELASTASE LIGANDS

| SEQ ID No | LIGAND | SEQUENCE |
|---|---|---|
| 54 | 10.21 | gggaggacgaugcggGCAGUGUGUAUUGAAGUAUAACUCUGUGAUCACCUGCUGcagacgacgagcggga |
| 55 | 10.22 | gggaggacgaugcggCACUAAGUAUCGUCACUAGCAUCAUGACGGAACCCGUGCCcagacgacgagcggga |
| 56 | 10.23 | gggaggacgaugcggCAGUCCAAAUGUAUAACAAGUAGCUGGUCAAACCCUUGGCcagacgacgagcggga |
| 57 | 10.25 | gggaggacgaugcggCAUGUCAAUACAAGCAUGUAAUCCACUAAGCAUCUGUCCCcagacgacgagcggga |
| 58 | 10.27 | gggaggacgaugcggCAGUAGUCUAGCAGUAUCGUCCCUGAAGGAUCAGGGUGUGcagacgacgagcggga |
| 59 | 10.29 | gggaggacgaugcggCAGUAGAUUGAAUGCAUCGUCACGUAAACUGCGUGGUCCCcagacgacgagcggga |
| 60 | 10.30 | gggaggacgaugcggCACUAAACCUGUAUAGCCGUACUAACAACCUCACCGUGCCcagacgacgagcggga |
| 61 | 10.31 | gggaggacgaugcggCAGAUGUCCUAGAUUUGGAUGUGUAACUAAGGUUGUGGUGcagacgacgagcggga |
| 62 | 10.32 | gggaggacgaugcggCAAUAGCUAGACUCUCAAAGAUGUGUAAAACACCGUUGGCcagacgacgagcggga |
| 63 | 10.33 | gggaggacgaugcggCAGCAUCGACUCUGUAAUCAGAUAAAUCAGGUGGGUGUGcagacgacgagcggga |
| 64 | 10.34 | gggaggacgaugcggCAACAAGUAUCAAUCAAACGUCGUCAUAGGUUACCUUGGCcagacgacgagcggga |
| 65 | 10.36 | gggaggacgaugcggCAGCAUGUAAUCAAUACUGCAGCAUAAACUCCGUGUGCCcagacgacgagcggga |
| 66 | 10.37 | gggaggacgaugcggCAGUAAUCUUGGUAUCAAGAUUACUGGGAUGUGCGUGCCcagacgacgagcggga |
| 67 | 10.38 | gggaggacgaugcggCAUAUCAUGGUGAUCUUGAUCCAAUAACCGUGAUUGUGCcagacgacgagcggga |
| 68 | 10.39 | gggaggacgaugcggCAGUGUGAUUAACAUAGCGGAUUAACAACACUGUCGUGGGcagacgacgagcggga |
| 69 | 10.40 | gggaggacgaugcggGCAAGAUCAAUCGGAUCAACACAACGUUGAUCCGCCUGCCcagacgacgagcggga |
| 70 | 10.41 | gggaggacgaugcggCAGAUCUACAAUCAGAUUGACUAAUCAUGAUCCGCCUGCCcagacgacgagcggga |
| 71 | 10.42 | gggaggacgaugcggCAUGAACUGAUAAUAAGGUUCAUAGCUUGAGGGUGUUGGCcagacgacgagcggga |
| 72 | 10.43 | gggaggacgaugcggCUAAUGAGCUUGAUAACAGGAUGUUAUCAAGCCGGCUGUAcagacgacgagcggga |
| 73 | 10.44 | gggaggacgaugcggCAUGUACAUAGUAUGACUCGUGAUCUGCCUCCAUGGUCCcagacgacgagcggga |
| 74 | 10.45 | gggaggacgaugcggCAGUGGUACCUGAGUACCACUAUAGCUGGAUAUAUGUGUCcagacgacgagcggga |
| 75 | 10.46 | gggaggacgaugcggAUUUUUCAACGCUUUACACGCACACUGAUUUAGUUAUGGGcagacgacgagcggga |
| 76 | 10.47 | gggaggacgaugcggCAUAGCUAAAUAACACUAACUAUGCCAAACGUCCGUGUAcagacgacgagcggga |
| 77 | 10.48 | gggaggacgaugcggCAUGAACUGAUAAUAAGGUUCAUAGCUUGAGGGUGUUGGCcagacgacgagcggga |
| 78 | 10.50 | gggaggacgaugcggUAGGACGAAACAUAGUCUACCAGCAGCCUCCAAGCCCCCCcagacgacgagcggga |
| 79 | 10.51 | gggaggacgaugcggCAGUAAUCUUGGUAUCAAGAUUACUGGGAUCUGUCGUGCCcagacgacgagcggga |
| 80 | 10.52 | gggaggacgaugcggCAAGUAGUGUACAUACAAUGCCAAGUCUCCCGGGUGUAcagacgacgagcggga |
| 81 | 10.54 | gggaggacgaugcggCAGUAAUCUUGGUAUCAAGAUUACUGGGAUCUGUCGUGCCcagacgacgagcggga |
| 82 | 10.55 | gggaggacgaugcggCAGUAGGGAUCUUGAGAAGUACUACUGCAGCCCUGUGCCcagacgacgagcggga |
| 83 | 10.56 | gggaggacgaugcggCAUGAUAAUGGAUUACAUCAUGAAGCUUAAGACUCCUGUGcagacgacgagcggga |
| 84 | 10.57 | gggaggacgaugcggAAUCAAUACCGUAAGUCCCUGUAACUAGUUAGGUUGUGCCcagacgacgagcggga |
| 85 | 10.58 | gggaggacgaugcggCAUGCCAUAGUUAUACCAAUGAUGUGAUGUAGGUGUGCCUcagacgacgagcggga |
| 86 | 10.59 | gggaggacgaugcggCAAUAGAUAUCAAGCAACCUCCUAGUCAUGGACAUGUUCCcagacgacgagcggga |
| 87 | 10.60 | gggaggacgaugcggCUAAUGAGCUUGAUAACAGGAUGUUAUCAAGCCGGCUGUGcagacgacgagcggga |
| 88 | 10.61 | gggaggacgaugcggCAGUAAUCUUGGUAUCAAGAUUACUGGGAUGUGCGUGCCcagacgacgagcggga |
| 89 | 10.62 | gggaggacgaugcggCACCUAUAUGUGCAUAGUUGCAUGAUCUAACCAUGUGCCCcagacgacgagcggga |

TABLE IV-continued

SPLINT-ELASTASE LIGANDS

| SEQ ID No | LIGAND | SEQUENCE |
|---|---|---|
| 90 | 10.63 | gggaggacgaugcggCAUAGUCACAAUUGAUUAGCUAGCUGCAUAGGGUGUUGGAcagacgacgagcggga |
| 91 | 10.64 | gggaggacgaugcggCAUAAGCAUAUGUACAUCCUAACCUCCUGAUGUUGUGCCcagacgacgagcggga |
| 92 | 10.65 | gggaggacgaugcggCAUAUGAAGAGCUUGCAAGUUACCUCCGAAUAAGUGUCCCcagacgacgagcggga |
| 93 | 10.66 | gggaggacgaugcggCAUAGUGUAGUAGAUAUGGAUGCCUGUACGUCCCUGCCcagacgacgagcggga |
| 94 | 10.67 | gggaggacgaugcggCAUAGCUGUAUACCUGAAGUCGAUAAGUACUCCCGUGCCCcagacgacgagcggga |
| 95 | 10.68 | gggaggacgaugcggCAAUACUAACAUAGCGUCCUAGGAUUAGGUCUCCCAUGGCcagacgacgagcggga |
| 96 | 10.69 | gggaggacgaugcggCAUAACGUGAAUAUCUGAGUACUAACCGUGUCGUUGUGCCcagacgacgagcggga |
| 97 | 10.70 | gggaggacgaugcggCAUAUGUGUGUAUAGUCCUACACAUAUGCGUGUGUGUGcagacgacgagcggga |
| 98 | 10.71 | gggaggacgaugcggCAUCCAUAAUACUCCUAAAGACCUCAUCAACUCCUGCUGcagacgacgagcggga |
| 99 | 10.73 | gggaggacgaugcggCAUAAGAUCAGUAUACAGAUAACCGAUAAGACCUUCCCCCcagacgacgagcggga |
| 100 | 10.72 | gggaggacgaugcggCACUGAGAGUGUAAGUAGAUAACCAAGUCCUCUGGGUGCCcagacgacgagcggga |
| 101 | 10.74 | gggaggacgaugcggCUAGUAACCAUGACUAGCUAAUAGGGCUAUCCGUCCUGGCcagacgacgagcggga |
| 102 | 10.75 | gggaggacgaugcggCACAAUUCAAUAAGUGCACCACUAACUAAUAUCGUGCUAcagacgacgagcggga |

TABLE V

Inactivation rate constants

| SEQ ID NO: | Inhibitor | kinact/[I] |
|---|---|---|
|  | nPhe val P | 1.6E + 04 |
|  | DNA:valP | 7.4E + 04 |
| 38 | rdO RNA:DNA:valP | 2.9E + 05 |
| 39 | 10.1 RNA:DNA:valP | 1.9E + 06 |
| 40 | 10.2 RNA:DNA:valP | 1.9E + 06 |
| 43 | 10.6 RNA:DNA:valP | 3.1E + 06 |
| 44 | 10.7 RNA:DNA:valP | 2.9E + 06 |
| 46 | 10.10 RNA:DNA:valP | 2.8E + 06 |
| 47 | 10.11 RNA:DNA:valP | 5.1E + 06 |
| 48 | 10.13 RNA:DNA:valP | 1.8E + 06 |
| 49 | 10.14 RNA:DNA:valP | 4.8E + 06 |
| 50 | 10.16 RNA:DNA:valP | 5.4E + 06 |
| 51 | 10.17 RNA:DNA:valP | 1.4E + 06 |
| 53 | 10.19 RNA:DNA:valP | 2.5E + 06 |
| 54 | 10.21 RNA:DNA:valP | 3.4E + 06 |
| 55 | 10.22 RNA:DNA:valP | 3.5E + 06 |
| 56 | 10.23 RNA:DNA:valP | 3.6E + 06 |
| 57 | 10.25 RNA:DNA:valP | 2.9E + 06 |
| 58 | 10.27 RNA:DNA:valP | 3.0E + 06 |
| 59 | 10.29 RNA:DNA:valP | 4.1E + 06 |
| 60 | 10.30 RNA:DNA:valP | 1.3E + 06 |
| 61 | 10.31 RNA:DNA:valP | 1.2E + 06 |
| 62 | 10.32 RNA:DNA:valP | 1.1E + 06 |
| 63 | 10.33 RNA:DNA:valP | 1.2E + 06 |
| 64 | 10.34 RNA:DNA:valP | 9.9E + 05 |
| 65 | 10.36 RNA:DNA:valP | 2.6E + 06 |
| 67 | 10.38 RNA:DNA:valP | 2.2E + 06 |
| 68 | 10.39 RNA:DNA:valP | 1.3E + 06 |
| 72 | 10.43 RNA:DNA:valP | 1.0E + 06 |
| 74 | 10.45 RNA:DNA:valP | 9.9E + 05 |
| 75 | 10.46 RNA:DNA:valP | 1.0E + 06 |
| 76 | 10.47 RNA:DNA:valP | 1.2E + 06 |
| 78 | 10.50 RNA:DNA:valP | 9.4E + 05 |
| 79 | 10.51 RNA:DNA:valP | 1.4E + 06 |
| 80 | 10.52 RNA:DNA:valP | 1.2E + 06 |
| 84 | 10.57 RNA:DNA:valP | 1.2E + 06 |
| 85 | 10.58 RNA:DNA:valP | 1.9E + 06 |
| 93 | 10.66 RNA:DNA:valP | 1.0E + 06 |
| 100 | 10.72 RNA:DNA:valP | 1.2E + 06 |

TABLE VI

| SEQ ID NO. | | LIGAND SEQUENCE |
|---|---|---|
| DNA SEQUENCES FROM HIGH SALT SELEX | | |
| 108 | DD1 | gggaggacAA CTGACACTTG TGCCGCATCG TCCTCCC |
| 109 | DD3 | gggaggacga tgcggGACAG GTGGTGTGGC AGGGTAGGTC ATGTTACTAA TTCATcagac gacgagcggg |
| 110 | DD4 | gggaggacga tgcggTGGAG AGCAATATGT GTACAAGTTA GCCTAGATGT GTTcagacga cgagcggg |
| 111 | DD5 | gggaggacga tgcggTGACC AAGTACCAGA GTACGCACCA TCTAATTCCC ACACTcagac gacaagcggg |
| 112 | DD6 | gggaggacga tgcggTGACA ACACAGTATC CTATAAAGTC TCACCCTTAT GCCAcagacg acgagcggg |
| 113 | DD7 | gggaggacga tgcggGACTG CGTATCAACG CGGTGAAACC TAACCTCATC TTGATcagac gacgcgggg |
| 114 | DD8 | gggcggacgt agcggTACGT GGCTTTAGCC GGGATTGACA GAATCCCTAT CACACcagac ggcgagcggg |
| 115 | DD9 | gggaggacga tgcggTGGGG GTGATGATAG GTCTAATTAG TCTTACGTGT GGAcagacga cgagcggg |
| 116 | DD10 | ggaggacgat gcggCCTACA CGGAGGTTGT TCTCAATGAA CTATCCTTGT ACCTcagacg acgagcggg |
| 117 | DD11 | gggaggacga tgcggGTGAG AAGGTGAGTT TAGTTTAGAT ATATCAAGTA TGGCcagacg acgagcggg |
| 118 | DD12 | gggaggacga tgcggCACCG CTATGCAGAT CTTATGCACC CATCATGCCA CCACAcagac aacgagcggg |
| 119 | DD13 | gggaggacga tgcggGCCGT AGTGTGTGGT ATGTACAACA ATGCATCTCA CATGcagac acgagcggg |
| 120 | DD14a | cccaggacga tgcggCAACG AGCATGACGT GAATGCCTTA TCGACCCACC CACCAcagac gacgagcggg |
| 121 | DD16 | gggaggacga tgcggTGACG ACATGCCAAT GTAAGAACAT GCTTACCCCT GTTGAcagac ggcgagcggg |
| 122 | DD17 | gggaggacga tgcggTGGAG GTGATGGTGT GATCAAACTT GCCTATTTAG GGAcagacga cgagcggg |
| 123 | DD18 | gggaggacga tgcggCACGA TGGTTAGGCG GGCCTTGAGG CTAATAATGT TGTTAcagac gacgagcggg |
| 124 | DD20 | gggaggacga tgcggTGCTG CGAAGCACTA TGATTAGATA GTGTACCATT TGGAcagacg acgagcggg |
| 125 | DD21 | gggaggacga tgcggTAGTA GGGGGAGATT GTTGTGTTAG GTGAGCTTAG TTTcagacga cgagcggg |
| 126 | DD22 | gggaggacga tgcggTGTCT TGCGGGTTAA GGCATGCTTA CTATGTCGGT GTGACcagac gacgagcggg |
| 127 | DD23 | gggcggacga tgcggCAACC ACAGGATCAC CCTGTCAAAT CGCTACCCAC ACCTAcagac gacgagcggg |
| 128 | DD25 | gggaggacga tgcggCCATG ACAGAATGTC TGCAGAGCTA ATCTTGGTCA CTGATcagac gacgagcggg |
| 129 | DD24 | gggaggacga tgcggTGGGG GTGTTGTATG TGTTATGTGC CAAATGACTT GTAcagacga cgagcggg |
| 130 | DD26 | gggaggacga tgcggTGGGG ACATGGGTGT TATAATTGGT TTGGTTCAAC CATcagacga cgagcggg |
| 131 | DD27 | gggaggacga tgcggACCTG CAAGCACCCT TATCACACAG CCACTCTATA CTCATcagac gaggagcggg |
| 132 | DD28 | gggaggacga tgcggCCTCT GCGGCAGAAG AAGATGTCAC CATCTTTACC TTGGGcagac gaggagcggg |
| 133 | DD30 | gggaggacga tgcggCACCA TCGTACGCAC CACTATTCCA TCAACTCTCT CTGAAcagac AACGAGTATT ACAAATACCA GACCCTTTAG CCCTATCCCT Acagacgacg agcggg |
| 134 | DD29 | gggaggacga tgcggTACGA CAGGCCACGA TAGCTTACGC CACCCACAGC ACTATcagac gacgagcggg |
| 135 | DD31 | gggaggacga tgcggCCCAT GGTGTGGGTG ACAACATGCA TCAGGTAAGA TGCTAcagac gac |
| 136 | DD32 | gggaggacga tgcggCAACG AGTATTACAA ATACCAGACC CTTACCCTAT CCCTAcagac gacgagcggg |
| 137 | DD33 | gggaggacga tgcggTACAG TCGTAAGACA CAAGAAGCAA TCTTGTTATG GTTGAcagac gacgagctgg |
| 138 | DD34 | gggaggacga tgcggTAGGG GGGGTGTAAC TGGGTAATCC ATAAATTGTC TGACTcagac gacgagcggg |
| 139 | DD35 | gggaggacga tgcggTGTGG GTAGGATGAA AGGTCGTTAC ATTGTGGTCT GTAcagacga cgagcggg |
| 140 | DD37 | gggaggacga tgcggCGACG AGAGTGCCAA ACTCCTTTAT CTACCCTCCA CATGAcagac gacgagcggg |
| 141 | DD38 | gggaggacga tgcggTACGG TGGTTAGGCA GGATTAGGTC TTATTTGTTG TGCAAcagac gacgagggg |
| 142 | DD39 | gggaggacga tgcggTACAC CATGACTCAT GGATACTTCG TATTATTACT TCGCAcagac gacgggcggg |
| 143 | DD40 | ggaggacgat gcggTACACA CCACCCAACA ATTCTTATCA CGACAACCAC TTATcagacg acgagcggg |

TABLE VI-continued

| SEQ ID NO. | | LIGAND SEQUENCE |
|---|---|---|
| 144 | DD41 | gggaggacga tgcggTCAAC CATTGATTAT GACTATCACC CTATCACCCA CCCATcagac gccgaggggg |
| 145 | DD42 | gggaggacga tgcggGACTG TGGACTTAGA ACACGCTGTG TGAACAGCTA CCTATcagac gacgggcggg |
| 146 | DD43 | gggaggacga tgcggTGGGG ACAGGTGTTC GTAAGTTGAG TTAGCTGATT GCcagacgac gagcggg |
| 147 | DD44 | gggaggacga tgcggTGGGA TGTACGGTGA ACACAAGNNN ATTATGGATC ATGGTcagac gacgagg |
| 148 | DD45 | gggaggacga tgcggGACGC TACTGGAGCC CTTATAACGC CACATTACAC ACACAcaggc gacgagc |
| 149 | DD46 | gggaggacga tgcggGTGGA GGTGATGTAG TAAGAAATAT AGTAAAGTGT CCTGcagacg acgagcggg |
| 150 | DD47 | gggaggacga tgcggCGCTG TCATATGGCA GTCAATGACG TACCCTGGTA CTACTcagac gacgagcggg |
| 151 | DD48 | gaggacgatg cggTACTGGT CTTACGGTGG GTAAATCTAA CAGACCCGAT CTAcagacgc cgagcggg |
| 152 | DD49 | ggaggacgat gcggCCAGAA GTGATGAACG CGATCTTTTA GATCTATTCC TCTAcagacg gcgagcggg |
| 153 | DD50 | gggaggacga tgcggCTGCA AACTATCGCA GATAGAGCGT TAGATCATTC TTCCAcagac gacgaccggg |
| 154 | DD51 | gggaggacga tgcggCAACG AACAGGTTTA ACCTGACAAC ACTACCCCTA CCATGcagac gacgagcggg |
| 155 | DD52 | gggaggacga tgcggGCACA GACGAAGTCG CAACTTGATT GCTATCCACC AGACAcagac gacgagcggg |
| 156 | DD53 | ggaggacgat gcggTGACGA GGATTACATC CCTACGATAA CAGTACTCTA TCTGcagacg acgagcggg |
| 157 | DD54 | gggaggacga tgcggCACGT CCGGAACATT TATGTGAGTT TTATAACACG TTGAAcagac gacgagcggg |
| RNA SEQUENCES FROM HIGH SALT SELEX | | |
| 158 | DR1 | gggaggacua ugccUGUCAG CCUCUAUGCC GCAUCGUCCU CCCUAUAGUG AGUCGUAUUG GGCUAGAGCG GCCGCCACC |
| 159 | DR2 | gggaggacga ugcggCACAG UGAUGUCAUG AUCAUAGGUA UACAUAUGCG UGAcagacga cgcgcggg |
| 160 | DR3 | gggaggacga ugcggCACCA UGGAUGUAGG GUGAUGGUUC AUGGGACUCA CGUGcagacg acgagcggg |
| 161 | DR4 | gggaggacga ugcggCAUCA UAUGAUAAAC ACAUGUCGCG CCCAACCUGA CCCCAcagac gacgagcggg |
| 162 | DR5 | gggaggacga ugcggCAGUA GCAAUAAGAC UACUGUAGGG UUGAAUCCGU GCUAcagacg acgagcggg |
| 163 | DR6 | gggaggacga ugcggCACUA UGGUGCAGGG UGAUGUGUCA GGUUCUCCAG UAcagacgac gagcggg |
| 164 | DR7 | gggaggacga ugcggUACCG UGAUGUCAUG AUCAUAGGUA UACAUAUGCG UAcagacgac gagcggg |
| 165 | DR8 | gggaggacua ugcggCACCA UGGAUGUAGG GUGAUGGUUC AAGUCCUCCG AUGCcagacg acgagcggg |
| 166 | DR9 | gggaggacga ugcggCAUAG AGAUGCUGAC AGGCAUAGUC CCAUCUCCUA AGUGcagacg acgagcggg |
| 167 | DR10 | gggaggacga ugcggUACCG UGAUGUCAUG AUCAUAGUGA GUCGUAUU |
| 168 | DR12 | gggaggacga ugcggCAUCU AUGACAAACC UAAUGUGGUC GUCCCUCCCG GACCAcagac gacgaggggg |
| 169 | DR13 | gggaggacga ugcggCUGAC UGGGUUGGUU AGGUAAGUAU GUCCGUGUUC AUGAUcagac gacgagcggg |
| 170 | DR14 | gggaggacga ugcggCAGUA GCAAUAAGAC UACUGUAGGG UUGAAUCCGU GCUGcagacg acgagcugg |
| 171 | DR15 | gggaggacga ugcggCAUCU AUGACAAACC UAAUGUGGUC GUCCCUCCCG GACCAcagaa gacgagcggg |
| 172 | DR16a | gggaggacga ugcggCGUAA CAAGCGUGUG UGAGGUCCCC UCCCCUCAC ACCAUcagac gccgagcggg |
| 173 | DR17 | gggaggacga ugcggCUCAU GUAUGAGGUC UAAGUACGCA UAGUCCCAUC GCAGAcagac gacgagcggg |
| 174 | DR19 | gggaggacga ugcggCAGUA GCAAUAAGAC UACUGUAGGG AUUGAAUCCG UGCUAcagac gacgagcggg |
| 175 | DR20 | gggaggacga ugcggCAAUG CAAGCCUGCA UGGUGUGAUG GGACUAUGCC UGUAcagacg acgagcggg |
| 176 | DR22 | gggaggacga ugcggCAAUA AUCUAGUUGC AUAGUCACCA UCGCAUCCGU GCAGGcagac aacgagcggg a |
| 177 | DR23 | gggaggacga ugcggCUCGA AAUGAAGUGU AAGCUCAAAG CCCACAGUGA UGUCcagacg acgagcggg |
| 178 | DR24 | gggaggacga ugcggCAUAG AGAUGCUGAC AGGCAUAGUC CCAUCUCCUA AGUGcagacg acgagcggg |
| 179 | DR25 | gggaggacga ugcggCACAU UGAAGAGUGC AAGUGUGCGG CCCACAGUGA UGUAcagacg acgagcggg |

TABLE VI-continued

| SEQ ID NO. | LIGAND | SEQUENCE |
|---|---|---|
| 180 | DR26 | gggaggacga ugcggCACUA UGGAUGCAGG GUGAUGUGUC AGGUUCUCCG GAAcagacga cgagcggg |
| 181 | DR27 | gggaggacga ugcggCAUAG AGAUGCUGAC AGGCAUAGUC CCAUCUCCUA AGUGCcagac gacgagcggg a |
| 182 | DR28 | gggaggacga ugcggCCUGA UAACCGUCCA GGCUAUUGAG GUGAUAGGUU GGGcagacga ugagcggg |
| 183 | DR29 | gggcggacga ugcggGACGA UUAGUUUGGC AUGUCUGUGG CACCCUCCCC Acagacgac gagcggg |
| 184 | DR30 | gggaggacga ugcggUACCA CGUGAGCUAC UAAAGUGAUC AAGUUGUAUG cagacgacg agcggg |
| 185 | DR31 | gggaggacga ugcggCUCGA AAUGAAGUGU AAGCUCAAAG CCCACAGUGA UGUCcagacg acgagcggg |
| 186 | DR32 | gggaggacga ugcggCAAUG CAAGCCUGCA UUGGUGUGAU GGGACUAUGC CUGUAcagac gacgagcggg a |

DNA SEQUENCES FROM ACTIVATED NEUTROPHIL SELEX

| 187 | ED1 | gggaggacga tgcggCAGCG TCATTTAGGA TTCGTCAGGT TCTACCCGTA GTGTGcagac gacgagcggg a |
| 188 | ED3 | gggaggacga tgcggCCTGT GTTGGTTAGT TAACACGCGA AGCTTCCCCG CTCCCcagac gacgagcggg a |
| 189 | ED5 | gggaggacga tgcggCACGT AAGTATCTAC GCGAGCAACA TGCTCTATCT CTCCCcagac gacgagcggg a |
| 190 | ED6 | gggaggacga tgcggCACGA CTTCCATGGC AGGGATTTCG GTGAGCCCCC TTAATcagac gacgagcggg a |
| 191 | ED7 | gggaggacga tgcggCAGGA AACAGGGGTG CACGGGGAAA TCATGCTTTA TCATCcagac gacgagcggg a |
| 192 | ED8 | gggaggacga tgcggCGACG AAGGTTCCAA CGTGGAATGG TTTTCACCCT ACCCGcagac gacgagcggg a |
| 193 | ED10 | gggaggacga tgcggCCTGC AGCTGATTCT GCGGGCACTA GCCTACATTC GGTAcagacg acgagcggga |
| 194 | ED12 | gggaggacga tgcggCAACG AAGGTTCCCC AGGAATGCGT TACGCTACAG TTGACcagac gacgagcggg a |
| 195 | ED13 | gggaggacga tgcggGGCGG TGTGAGAACA CGACACCTAG TGTCTACCAT CTGACcagac gacgagcggg a |
| 196 | ED15 | gggaggacga tgcggCAGNN GGNNCAGGTA ATGTGAGTAA CCTCTACTAC TCTGcagacg acgagcggga |
| 197 | ED16 | gggaggacga tgcggCACGT AAGCTGTACC AATTGGTTAA TCACACACTC CCCAcagacg acgagcggga |
| 198 | ED21 | gggaggacga tgcggACCAC AGCCACTAGN NGCATCGTCC TCTGCGTCca gacgacgagc ggga |
| 199 | ED24 | gggaggacga tgcggCACGT CAGTGCTACT TCGGTTCTTT GTCAACCTAT TCCAcagacg acgagcggga |
| 200 | ED25 | gggaggacga tgcggTACGC AGAGGACGAT GCGGGCTACT GGCTGTGGTc agacgacgag cggga |
| 201 | ED26 | gggaggacga tgcggCAGGA GACGCTACCC ACCGGTTACA TTGAATATCT CTCCCcagac gacgagcggg a |
| 202 | ED27 | gggaggacga tgcggGGGGC GTAGATGACT TAGAACCCTA TTAGTGGCAC ACGCcagacg acgagcggga |
| 203 | ED30 | gggaggacga tgcggGCACA CAAACACAGT GCGAACGGTA GTTCTAATCC TCCTGcagac gacgagcggg a |
| 204 | ED31 | gggaggacga tgcggTAGCA GCGGAGGACG ATGCGGTCTT TTGCATCCCc agacgacgag cggga |
| 205 | ED33 | gggaggacga tgcggCTTGA CGACGGATGT AGCTACGCGT TGAGTCCACA ACAGGcagac gacgagcggg a |
| 206 | ED34 | gggaggacga tgcggGGCGT TGCGTGACTC CAGTACTGGT CTATTTATCC TCGTCcagac gacgagcggg a |
| 207 | ED38 | gggaggacga tgcggCACGG TAGTGCTACC AGATGGTTAT GTTACTTCAA TCTGcagac gacgagcggg a |
| 208 | ED39 | gggaggacga tgcggGGCGG GATCATGCTA CCAGTTGGTT ATCATCTACT TACCCcagac gacgagcggg a |
| 209 | ED40 | gggaggacga tgcggACGGT AGTGCTACCA GATGGTTATG TTACTTCAAT TCTGcagacg acgagcggga |
| 210 | ED42 | gggaggacga tgcggCAGGG CGGAATTTGA GTGAGCAGTC TTAAAATGTC GTCTGcagac gacgagcggg a |
| 211 | ED43 | gggaggacga tgcggCACGG TAGTGCTACC AGATGGTTAT GTTACTTCAA TTCTGcagac gacgagcggg a |
| 212 | ED45 | gggaggacga tgcggCCTGC GTAACAACGC GGAGGAAACT TCCCTCCTAT CTCTGcagac gacgagcggg a |
| 213 | ED47 | gggaggacga tgcggCAGGA CATGCTACCA ATCGGGTATA TCGACTTCTA CTCTCcagac gacgagcggg a |
| 214 | ED48 | gggaggacga tgcggCACCG TCATTTAGGA TTCGTCAGGC TCTACCCGTA GTGTGcagac gacgagcggg a |
| 215 | ED49 | gggaggacga tgcggTAGGA AACAGGGGTG CACGGGGAAA TCATGCTTTA TCATCcagac gacgagcggg a |

TABLE VI-continued

| SEQ ID NO. | | LIGAND SEQUENCE |
|---|---|---|
| 216 | ED51 | gggaggacga tgcggCAGGA CGACTCGTAG GCACCTAACC TAACAACTAA CGCTAcagac gacgagcggg a |
| 217 | ED54 | gggaggacga tgcggGCCGA CGTAGTGTAC ATTTAAACCA GGGGCCTGCT CTCTAcagac gacgagcggg a |
| 218 | ED57 | gggaggacga tgcggGGGGC AGATGATGTT GTTTGAACCC TAGTACTGGC AGTGCcagac gacgagcggg a |
| 219 | ED59 | gggaggacga tgcggGGGCA GAACCGACAT TTTGCCCTAC ATACGTAGCT TTCCAcagac gacgagcggg a |
| 220 | ED58 | gggaggacga tgcggGGGGT CACGATTTGC GTCTCTCAGT GATTAGCATT CTCGTcagac gacgagcggg a |
| 221 | Ed60 | gggaggacga tgcggCACGA CGGAATTTTT AAGTGAGCAA AGATTGTTAG TGAGcagacg acgagcggga |
| 222 | ED64 | gggaggacga tgcggCACCT TAAGCGTACG CGGGACTTGT TACCTACTCT ACTCcagacg acgagcggga |
| 223 | ED65 | gggaggacga tgcggCACCC GAAGATGCTA CCAATTGGTT CCAGTTTTAT CCCTCcagac gacgagcggg a |
| 224 | ED67 | gggaggacga tgcggCCACT GACGAGACAA CACTTCGGCA GGCGCACGTA ACCCAcagac gacgagcggg a |

TABLE VII

| SEQ ID NO. | ligand | $k_{inact}/K_I$, $M^{-1}$ $min^{-1}$ |
|---|---|---|
| 38 | 40N7.1 | 1.86e + 06 |
| 109 | DD3 | 6.18e + 07 |
| 110 | DD4 | 3.14e + 07 |
| 111 | DD5 | 3.63e + 07 |
| 113 | DD7 | 1.04e + 08 |
| 114 | DD8 | 2.24e + 08 |
| 115 | DD9 | 6.06e + 06 |
| 116 | DD10 | 1.39e + 08 |
| 117 | DD11 | 1.44e + 07 |
| 118 | DD12 | 3.75e + 07 |
| 119 | DD13 | 3.07e + 07 |
| 120 | DD14 | 1.01e + 08 |
| 121 | DD16 | 4.49e + 07 |
| 122 | DD17 | 4.21e + 05 |
| 123 | DD18 | 1.67e + 08 |
| 124 | DD20 | 2.33e + 08 |
| 125 | DD21 | 2.51e + 07 |
| 126 | DD22 | 2.41e + 07 |
| 127 | DD23 | 9.36e + 07 |
| 129 | DD24 | 1.3e + 07 |
| 128 | DD25 | 1.12e + 08 |
| 130 | DD26 | 1.9e + 07 |
| 131 | DD27 | 3.37e + 07 |
| 188 | ED3 | 6.6e + 07 |
| 189 | ED5 | 1e + 08 |
| 190 | ED6 | 6.3e + 08 |
| 191 | ED7 | 1.5e + 08 |
| 192 | ED8 | 1e + 08 |
| 193 | ED10 | 1.4e + 08 |
| 194 | ED12 | 3.5e + 08 |
| 195 | ED13 | 7.9e + 07 |
| 196 | ED15 | 4.8e + 08 |
| 197 | ED16 | 5e + 08 |
| 198 | ED21 | 3.2e + 06 |
| 199 | ED24 | 1.6e + 08 |

We claim:

1. Nucleic acid ligands that bind covalently with a protein, wherein said nucleic acid ligands comprise a chemically reactive functional unit, wherein said nucleic acid ligands are produced by the method comprising the steps of:

a) preparing a candidate mixture of nucleic acids;

b) contacting the candidate mixture with said protein, wherein nucleic acids which bind covalently with said protein may be partitioned from the remainder of the candidate mixture;

c) partitioning the nucleic acids that bind covalently with the protein from the remainder of the candidate mixture; and d) amplifying the nucleic acids that bind covalently with the protein, whereby nucleic acid ligands that bind covalently with the protein may be produced.

2. The nucleic acid ligands of claim 1 which are selected from the sequences listed in Table VI (SEQ ID NOS: 108–224).

3. A facilitating nucleic acid, wherein said nucleic acid comprises a chemically reactive functional unit, identified according to the method comprising the steps of:

a) preparing a candidate mixture of nucleic acids;

b) contacting the candidate mixture with a protein, wherein nucleic acids having a facilitating activity, as indicated by a covalent bond being formed between said protein and said nucleic acid, relative to the candidate mixture may be partitioned from the remainder of the candidate mixture;

c) partitioning the nucleic acids having a facilitating activity from the remainder of the candidate mixture; and d) amplifying the nucleic acids having a facilitating activity, whereby a facilitating nucleic acid may be identified.

4. A method for partitioning nucleic acids from a nucleic acid candidate mixture, wherein said nucleic acid ligands comprise a chemically reactive functional unit, said method comprising:

a) preparing a nucleic acid candidate mixture;

b) contacting the nucleic acid candidate mixture with a protein under conditions wherein nucleic acids form a covalent bond with said protein; and c) partitioning away the remainder of the nucleic acid candidate mixture which did not form a covalent bond with the protein, leaving only nucleic acids which have formed a covalent bond with the protein.

5. A purified and isolated non-naturally occurring nucleic acid ligand which binds covalently with a protein, wherein said nucleic acid ligand comprises a chemically reactive functional unit.

* * * * *

SEQUENCE LISTING (1) GENERAL INFORMATION:

(iii) NUMBER OF SEQUENCES: 226

(2) INFORMATION FOR SEQ ID NO:1:

(i) SEQUENCE CHARACTERISTICS:
      (A) LENGTH: 77 nucleotides
      (B) TYPE: nucleic acid
      (C) STRANDEDNESS: single
      (D) TOPOLOGY: linear (ii) MOLECULE TYPE: RNA (xi) SEQUENCE DESCRIPTION: SEQ ID NO:1:

GGGAGCUCAG AAUAAACGCU CAANNNNNNN NNNNNNNNNN NNNNNNNNNN        50

NNNUUCGACA UGAGGCCCGG AUCCGGC                                 77

(2) INFORMATION FOR SEQ ID NO:2:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:2:

GGGAGCUCAG AAUAAACGCU CAACUCCCCC GUGCUGCCUU AGCGCGUAGU        50

UCGUUCGACA UGAGGCCCGG AUCCGGC                                 77

(2) INFORMATION FOR SEQ ID NO:3:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:3:

GGGAGCUCAG AAUAAACGCU CAACUCCCCG UUAGCGCCUC ACUGACGUGU        50

CGAUUCGACA UGAGGCCCGG AUCCGGC                                 77

(2) INFORMATION FOR SEQ ID NO:4:

(i) SEQUENCE CHARACTERISTICS:
        (A) LENGTH: 76 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:4:

GGGAGCUCAG AAUAAACGCU CAACUGAGUC AUGCGGCAGC UCCCCGCCAC        50

GCUUCGACAU GAGGCCCGGA UCCGGC                                  76

(2) INFORMATION FOR SEQ ID NO:5:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:5:

GGGAGCUCAG AAUAAACGCU CAAUGCCUUG UUCUUUUACU CCCCCGACGC        50

CUCUUCGACA UGAGGCCCGG AUCCGGC                                 77

(2) INFORMATION FOR SEQ ID NO:6:

(i) SEQUENCE CHARACTERISTICS:
        (A) LENGTH: 77 nucleotides
        (B) TYPE: nucleic acid

```
            (C) STRANDEDNESS: single
            (D) TOPOLOGY: linear (ii) MOLECULE TYPE: RNA (xi) SEQUENCE DESCRIPTION: SEQ ID NO:6:

GGGAGCUCAG AAUAAACGCU CAACGUUUAG GACUCCCCCG UUCGUCGAGC          50

GAAUUCGACA UGAGGCCCGG AUCCGGC                                  77

(2) INFORMATION FOR SEQ ID NO:7:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:7:

GGGAGCUCAG AAUAAACGCU CAACGUUUAG GUCUCCCCCG UCCGUCGAGC          50

GAAUUCGACA UGAGGCCCGG AUCCGGC                                  77

(2) INFORMATION FOR SEQ ID NO:8:

(i) SEQUENCE CHARACTERISTICS:
        (A) LENGTH: 78 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:8:

GGGAGCUCAG AAUAAACGCU CAACUGCGUU ACUCCCCCGG ACAACUGUUC          50

GUUAUUCGAC AUGAGGCCCG GAUCCGGC                                 78

(2) INFORMATION FOR SEQ ID NO:9:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:9:

GGGAGCUCAG AAUAAACGCU CAAUCUUCGU GUUCCCCGUG CUGUGUCGUC          50

ACGUUCGACA UGAGGCCCGG AUCCGGC                                  77

(2) INFORMATION FOR SEQ ID NO:10:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:10:

GGGAGCUCAG AAUAAACGCU CAAACGUCAU UCCGAGUCGG GUUCGUUCCC          50

CGCUUCGACA UGAGGCCCGG AUCCGGC                                  77
```

(2) INFORMATION FOR SEQ ID NO:11:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:11:

```
GGGAGCUCAG AAUAAACGCU CAAUGUGUGA GUGGAUCCGU UCCCCGCCUG          50

GUGUUCGACA UGAGGCCCGG AUCCGGC                                   77
```

(2) INFORMATION FOR SEQ ID NO:12:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:12:

```
GGGAGCUCAG AAUAAACGCU CAAUGGACAC AACUCCGUUA UCUCGCUCUC          50

AGCUUCGACA UGAGGCCCGG AUCCGGC                                   77
```

(2) INFORMATION FOR SEQ ID NO:13:

(i) SEQUENCE CHARACTERISTICS:
        (A) LENGTH: 78 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:13:

```
GGGAGCUCAG AAUAAACGCU CAAUGAACAC AACUUCAUAU CUCGGGACUC          50

ACAGUUCGAC AUGAGGCCCG GAUCCGGC                                  78
```

(2) INFORMATION FOR SEQ ID NO:14:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:14:

```
GGGAGCUCAG AAUAAACGCU CAAUCGACAC AACUCGAUCU CCGUGGCUGU          50

CACUUCGACA UGAGGCCCGG AUCCGGC                                   77
```

(2) INFORMATION FOR SEQ ID NO:15:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:15:

```
GGGAGCUCAG AAUAAACGCU CAAUCGACAC AACUCGAUCU CCGUGUCUGU        50

CACUUCGACA UGAGGCCCGG AUCCGGC                                 77
```

(2) INFORMATION FOR SEQ ID NO:16:

(i) SEQUENCE CHARACTERISTICS:
        (A) LENGTH: 79 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:16:

```
GGGAGCUCAG AAUAAACGCU CAAUGGACAC AACUCCAUUC AUCCCGGGAC        50

CGCUGUUCGA CAUGAGGCCC GGAUCCGGC                               79
```

(2) INFORMATION FOR SEQ ID NO:17:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:17:

```
GGGAGCUCAG AAUAAACGCU CAAUGGUCAC AACUCCAUUA GCUGAGGCCC        50

GUGUUCGACA UGAGGCCCGG AUCCGGC                                 77
```

(2) INFORMATION FOR SEQ ID NO:18:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:18:

```
GGGAGCUCAG AAUAAACGCU CAAGCGACAC AACUCGAUCU CCGUGGCUGU        50

CACUUCGACA UGAGGCCCGG AUCCGGC                                 77
```

(2) INFORMATION FOR SEQ ID NO:19:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:19:

```
GGGAGCUCAG AAUAAACGCU CAAGUCUCAC AACUGGCUUA UCCGGUGCGC        50

ACGUUCGACA UGAGGCCCGG AUCCGGC                                 77
```

(2) INFORMATION FOR SEQ ID NO:20:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:20:

GGGAGCUCAG AAUAAACGCU CAAGCCACAC AACUGGCUUA UCCUGAACGC          50

GGCUUCGACA UGAGGCCCGG AUCCGGC          77

(2) INFORMATION FOR SEQ ID NO:21:

(i) SEQUENCE CHARACTERISTICS:
        (A) LENGTH: 78 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:21:

GGGAGCUCAG AAUAAACGCU CAACCAUCAC AACUUGGUUA UCCGGUACUC          50

UGUGUUCGAC AUGAGGCCCG GAUCCGGC          78

(2) INFORMATION FOR SEQ ID NO:22:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:22:

GGGAGCUCAG AAUAAACGCU CAACAUCACA ACUUGUUAUC CGCUUCACCG          50

CUCUUCGACA UGAGGCCCGG AUCCGGC          77

(2) INFORMATION FOR SEQ ID NO:23:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:23:

GGGAGCUCAG AAUAAACGCU CAACAUCACA ACUUGUUGUC CUGGUCGAUG          50

UCCUUCGACA UGAGGCCCGG AUCCGGC          77

(2) INFORMATION FOR SEQ ID NO:24:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:24:

GGGAGCUCAG AAUAAACGCU CAACAUCACA ACUUGUUGUC CCGGUACUUG          50

UGUUUCGACA UGAGGCCCGG AUCCGGC          77

(2) INFORMATION FOR SEQ ID NO:25:

(i) SEQUENCE CHARACTERISTICS:
    (A) LENGTH: 78 nucleotides
    (B) TYPE: nucleic acid
    (C) STRANDEDNESS: single
    (D) TOPOLOGY: linear (ii) MOLECULE TYPE: RNA (xi) SEQUENCE DESCRIPTION: SEQ ID NO:25:

GGGAGCUCAG AAUAAACGCU CAAUGUCACA ACUCAUUGUU CGGGAAUUGU          50

GCCAUUCGAC AUGAGGCCCG GAUCCGGC                                 78

(2) INFORMATION FOR SEQ ID NO:26:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:26:

GGGAGCUCAG AAUAAACGCU CAACGUCAGC GGAUCUCCAU UGCGUUAUAC          50

GGGUUCGACA UGAGGCCCGG AUCCGGC                                  77

(2) INFORMATION FOR SEQ ID NO:27:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:27:

GGGAGCUCAG AAUAAACGCU CAACGAAUCAA UGCGCGGAUC UCAGGAUAU          50

UCGUUCGACA UGAGGCCCGG AUCCGGC                                  77

(2) INFORMATION FOR SEQ ID NO:28:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:28:

GGGAGCUCAG AAUAAACGCU CAAGCGGUAA CAUGCUGGAU CUCAGGAAAC          50

CGCUUCGACA UGAGGCCCGG AUCCGGC                                  77

(2) INFORMATION FOR SEQ ID NO:29:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:29:

GGGAGCUCAG AAUAAACGCU CAAGCGGUAA CAUGCUGGAU CUCAGGAAAC          50

```
CGUUUCGACA UGAGGCCCGG AUCCGGC                                         77

(2) INFORMATION FOR SEQ ID NO:30:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:30:

GGGAGCUCAG AAUAAACGCU CAAUGCCACU UUUGUUCGGA UCUUAGGAAG              50

GCAUUCGACA UGAGGCCCGG AUCCGGC                                       77

(2) INFORMATION FOR SEQ ID NO:31:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:31:

GGGAGCUCAG AAUAAACGCU CAAUCAUCAU UUGUACCGGA UCUCAGUGUG              50

AUGUUCGACA UGAGGCCCGG AUCCGGC                                       77

(2) INFORMATION FOR SEQ ID NO:32:

(i) SEQUENCE CHARACTERISTICS:
        (A) LENGTH: 78 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:32:

GGGAGCUCAG AAUAAACGCU CAAAGCUGUU GGCAGCCCGG AUCUACGCAU              50

GGGAUUCGAC AUGAGGCCCG GAUCCGGC                                      78

(2) INFORMATION FOR SEQ ID NO:33:

(i) SEQUENCE CHARACTERISTICS:
        (A) LENGTH: 78 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:33:

GGGAGCUCAG AAUAAACGCU CAAAGCUGUU GGCAGCGCUG GUGAAGGGAU              50

AGGCUUCGAC AUGAGGCCCG GAUCCGGC                                      78

(2) INFORMATION FOR SEQ ID NO:34:

(i) SEQUENCE CHARACTERISTICS:
        (A) LENGTH: 78 nucleotides
        (B) TYPE: nucleic acid
        (C) STRANDEDNESS: single
        (D) TOPOLOGY: linear (ii) MOLECULE TYPE: RNA
```

(xi) SEQUENCE DESCRIPTION: SEQ ID NO:34:

GGGAGCUCAG AAUAAACGCU CAAUGAGAAC UCCGUGAUUG AGUCAGGUAC           50

GCGCUUCGAC AUGAGGCCCG GAUCCGGC                                  78

(2) INFORMATION FOR SEQ ID NO:35:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:35:

GGGAGCUCAG AAUAAACGCU CAAUCCGUGU UGCCACUCCA GUUACUGGAC           50

GCCUUCGACA UGAGGCCCGG AUCCGGC                                   77

(2) INFORMATION FOR SEQ ID NO:36:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:36:

GGGAGCUCAG AAUAAACGCU CAAGUGGAGC UUCGUGACUU GGUCGGAGCC           50

GUGUUCGACA UGAGGCCCGG AUCCGGC                                   77

(2) INFORMATION FOR SEQ ID NO:37:

(i) SEQUENCE CHARACTERISTICS:
        (A) LENGTH: 77 nucleotides
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:37:

GGGAGCUCAG AAUAAACGCU CAAUCGUGUC GCCACCAGCC UUUCUCGUGC           50

GCCUUCGACA UGAGGCCCGG AUCCGGC                                   77

(2) INFORMATION FOR SEQ ID NO:38:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All C's are 2'-NH2 cytosine (ix) FEATURE:
        (D) OTHER INFORMATION:  All U's are 2'-NH2 uracil (xi) SEQUENCE DESCRIPTION: SEQ ID NO:38:

GGGAGGACGA UGCGGNNNNN NNNNNNNNNN NNNNNNNNNN NNNNNNNNNN           50

NNNNNCAGAC GACGAGCGGG A                                         71

(2) INFORMATION FOR SEQ ID NO:39:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:39:

```
GGGAGGACGA UGCGGCAUGA UCUAGGUAAA GACAUAUCAC UAACCUGAUU          50

GUGCCCAGAC GACGAGCGGG A                                         71
```

(2) INFORMATION FOR SEQ ID NO:40:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:40:

```
GGGAGGACGA UGCGGCAGUA AUCUUUGGUA UCAAGAUUAC UGGGAUGUCC          50

GUGCCCAGAC GACGAGCGGG A                                         71
```

(2) INFORMATION FOR SEQ ID NO:41:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:41:

```
GGGAGGACGA UGCGGCAGUA AUCUUUGGUA UCAAGAUUAC UGGGAUGUGC          50

GUGCCCAGAC GACGAGCGGG A                                         71
```

(2) INFORMATION FOR SEQ ID NO:42:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
    (D) OTHER INFORMATION: All C's are 2'-NH2 cytosine (ix) FEATURE:
    (D) OTHER INFORMATION: All U's are 2'-NH2 uracil (xi) SEQUENCE DESCRIPTION: SEQ ID NO:42:

GGGAGGACGA UGCGGCAAAC CAUCUAAGCU GUGAUAUGAC UCCUAAGACA            50

GUGCCCAGAC GACGAGCGGG A                                          71

(2) INFORMATION FOR SEQ ID NO:43:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:43:

GGGAGGACGA UGCGGCAUCG UCAAUGUAGU AGUACUACGU AAGUCACGUG            50

GUCCCCAGAC GACGAGCGGG A                                          71

(2) INFORMATION FOR SEQ ID NO:44:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:44:

GGGAGGACGA UGCGGCGAUA AUCUUGGUAU CAAGAUUACU GGGAUGUCGC            50

GUGCCCAGAC GACGAGCGGG A                                          71

(2) INFORMATION FOR SEQ ID NO:45:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:45:

GGGAGGACGA UGCGGCAUAU CUACAUGUAG GUCCUAAUCG AAAUCCAGUU            50

```
GUGCCCAGAC GACGAGCGGG A                                              71

(2) INFORMATION FOR SEQ ID NO:46:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:   All C's are 2'-NH2 cytosine (ix) FEATURE:
        (D) OTHER INFORMATION:   All U's are 2'-NH2 uracil (xi) SEQUENCE DESCRIPTION: SEQ ID NO:46:

GGGAGGACGA UGCGGCAUUA GUCCGUAGCA UAGCACUAUC UAAACCAGUU               50

GGGGACAGAC GACGAGCGGG A                                              71

(2) INFORMATION FOR SEQ ID NO:47:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:   All C's are 2'-NH2 cytosine (ix) FEATURE:
        (D) OTHER INFORMATION:   All U's are 2'-NH2 uracil (xi) SEQUENCE DESCRIPTION: SEQ ID NO:47:

GGGAGGACGA UGCGGCUACA UAGGUUAAGA UUACCUAACC GAAUUAACAU               50

GCAGCCAGAC GACGAGCGGG A                                              71

(2) INFORMATION FOR SEQ ID NO:48:

(i) SEQUENCE CHARACTERISTICS:
        (A) LENGTH: 70 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:   All C's are 2'-NH2 cytosine (ix) FEATURE:
        (D) OTHER INFORMATION:   All U's are 2'-NH2 uracil (xi) SEQUENCE DESCRIPTION: SEQ ID NO:48:

GGGAGGACGA UGCGGUAAGU UACUACCGAU ACAACCGAAG UCCUCUACCC               50

GUGGCAGACG ACGAGCGGGA                                                70

(2) INFORMATION FOR SEQ ID NO:49:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear
```

(ii) MOLECULE TYPE: RNA (ix) FEATURE:
             (D) OTHER INFORMATION:  All C's are 2'-NH2 cytosine (ix) FEATURE:
             (D) OTHER INFORMATION:  All U's are 2'-NH2 uracil (xi) SEQUENCE DESCRIPTION: SEQ ID NO:49:

GGGAGGACGA UGCGGCAUUA CUAAGAUUAA CAGCUUAGUA UAACAGCCUC          50

CUGUGCAGAC GACGAGCGGG A                                        71

(2) INFORMATION FOR SEQ ID NO:50:

(i) SEQUENCE CHARACTERISTICS:
             (A) LENGTH: 71 nucleotides
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION:  All C's are 2'-NH2 cytosine (ix) FEATURE:
             (D) OTHER INFORMATION:  All U's are 2'-NH2 uracil (xi) SEQUENCE DESCRIPTION: SEQ ID NO:50:

GGGAGGACGA UGCGGCACGU ACAGUCUAAA AGUGUGUUAG UGUAGCGGUG          50

GUGUGCAGAC GACGAGCGGG A                                        71

(2) INFORMATION FOR SEQ ID NO:51:

(i) SEQUENCE CHARACTERISTICS:
             (A) LENGTH: 70 nucleotides
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION:  All C's are 2'-NH2 cytosine (ix) FEATURE:
             (D) OTHER INFORMATION:  All U's are 2'-NH2 uracil (xi) SEQUENCE DESCRIPTION: SEQ ID NO:51:

GGGAGGACGA UGCGGCAGUA GCAAUAAGAC UACUGUAGGG UUGAAUCCGU          50

GCUGCAGACG ACGAGCGGGA                                          70

(2) INFORMATION FOR SEQ ID NO:52:

(i) SEQUENCE CHARACTERISTICS:
             (A) LENGTH: 71 nucleotides
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION:  All C's are 2'-NH2 cytosine (ix) FEATURE:
             (D) OTHER INFORMATION:  All U's are 2'-NH2 uracil (xi) SEQUENCE DESCRIPTION: SEQ ID NO:52:

GGGAGGACGA UGCGGCAUUA CUAAGAUUAA CAGCUUAGUA UAACAGCCUC          50

```
CUGUGCAGAC GACGAGCGGG A                                              71

(2) INFORMATION FOR SEQ ID NO:53:

(i) SEQUENCE CHARACTERISTICS:
         (A) LENGTH: 71 nucleotides
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION:  All C's are 2'-NH2 cytosine (ix) FEATURE:
         (D) OTHER INFORMATION:  All U's are 2'-NH2 uracil (xi) SEQUENCE DESCRIPTION: SEQ ID NO:53:

GGGAGGACGA UGCGGUGCAU GCGUACCAGU AUCCUAAACU AAACCUAGCG                50

UGCCCCAGAC GACGAGCGGG A                                              71

(2) INFORMATION FOR SEQ ID NO:54:

(i) SEQUENCE CHARACTERISTICS:
         (A) LENGTH: 70 nucleotides
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION:  All C's are 2'-NH2 cytosine (ix) FEATURE:
         (D) OTHER INFORMATION:  All U's are 2'-NH2 uracil (xi) SEQUENCE DESCRIPTION: SEQ ID NO:54:

GGGAGGACGA UGCGGGCAGU GUGUAUUGAA GUAUAACUCU GUGAUCACCU                50

GCUGCAGACG ACGAGCGGGA                                                70

(2) INFORMATION FOR SEQ ID NO:55:

(i) SEQUENCE CHARACTERISTICS:
         (A) LENGTH: 71 nucleotides
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION:  All C's are 2'-NH2 cytosine (ix) FEATURE:
         (D) OTHER INFORMATION:  All U's are 2'-NH2 uracil (xi) SEQUENCE DESCRIPTION: SEQ ID NO:55:

GGGAGGACGA UGCGGCACUA AGUAUCGUCA CUAGCAUCAU GACGGAACCC                50

GUGCCCAGAC GACGAGCGGG A                                              71

(2) INFORMATION FOR SEQ ID NO:56:

(i) SEQUENCE CHARACTERISTICS:
         (A) LENGTH: 71 nucleotides
         (B) TYPE: nucleic acid
         (C) STRANDEDNESS: single
         (D) TOPOLOGY: linear
```

(ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:56:

GGGAGGACGA UGCGGCAGUC CAAAUGUAUA ACAAGUAGCU GGUCAAACCC          50

UUGGCCAGAC GACGAGCGGG A                                         71

(2) INFORMATION FOR SEQ ID NO:57:

(i) SEQUENCE CHARACTERISTICS:
            (A) LENGTH: 71 nucleotides
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:57:

GGGAGGACGA UGCGGCAUGU CAAUACAAGC AUGUAAUCCA CUAAGCAUCU          50

GUCCCCAGAC GACGAGCGGG A                                         71

(2) INFORMATION FOR SEQ ID NO:58:

(i) SEQUENCE CHARACTERISTICS:
            (A) LENGTH: 71 nucleotides
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:58:

GGGAGGACGA UGCGGCAGUA GUCUAGCAGU AUCGUCCCUG AAGGAUCAGG          50

GUGUGCAGAC GACGAGCGGG A                                         71

(2) INFORMATION FOR SEQ ID NO:59:

(i) SEQUENCE CHARACTERISTICS:
            (A) LENGTH: 71 nucleotides
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:59:

```
GGGAGGACGA UGCGGCAGUA GAUUGAAUGC AUCGUCACGU AAACUGCUGG          50

GUCCCCAGAC GACGAGCGGG A                                         71
```

(2) INFORMATION FOR SEQ ID NO:60:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:60:

```
GGGAGGACGA UGCGGCACUA AACCUGUAUA GCCGUACUAA CAACCUCACC          50

GUGCCCAGAC GACGAGCGGG A                                         71
```

(2) INFORMATION FOR SEQ ID NO:61:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:61:

```
GGGAGGACGA UGCGGCAGAU GUCCUAGAUU UGGAUGUGUA ACUAAGGUUG          50

UGGUGCAGAC GACGAGCGGG A                                         71
```

(2) INFORMATION FOR SEQ ID NO:62:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:62:

```
GGGAGGACGA UGCGGCAAUA GCUAGACUCU CAAAGAUGUG UAAAACACCG          50

UUGGCCAGAC GACGAGCGGG A                                         71
```

(2) INFORMATION FOR SEQ ID NO:63:

(i) SEQUENCE CHARACTERISTICS:
        (A) LENGTH: 70 nucleotides
        (B) TYPE: nucleic acid
        (C) STRANDEDNESS: single (D) TOPOLOGY: linear (ii) MOLECULE TYPE: RNA (ix) FEATURE:
          (D) OTHER INFORMATION: All C's are 2'-NH2 cytosine (ix) FEATURE:
          (D) OTHER INFORMATION: All U's are 2'-NH2 uracil (xi) SEQUENCE DESCRIPTION: SEQ ID NO:63:

GGGAGGACGA UGCGGCAGCA UCGACUCUGU AAUCAGAUAA AUCAGGUGGG         50

UGUGCAGACG ACGAGCGGGA                                          70

(2) INFORMATION FOR SEQ ID NO:64:

(i) SEQUENCE CHARACTERISTICS:
          (A) LENGTH: 71 nucleotides
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: All C's are 2'-NH2 cytosine (ix) FEATURE:
          (D) OTHER INFORMATION: All U's are 2'-NH2 uracil (xi) SEQUENCE DESCRIPTION: SEQ ID NO:64:

GGGAGGACGA UGCGGCAACA AGUAUCAAUC AAACGUCGUC AUAGGUUACC         50

UUGGCCAGAC GACGAGCGGG A                                        71

(2) INFORMATION FOR SEQ ID NO:65:

(i) SEQUENCE CHARACTERISTICS:
          (A) LENGTH: 70 nucleotides
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: All C's are 2'-NH2 cytosine (ix) FEATURE:
          (D) OTHER INFORMATION: All U's are 2'-NH2 uracil (xi) SEQUENCE DESCRIPTION: SEQ ID NO:65:

GGGAGGACGA UGCGGCAGCA UGUAAUCAAU ACUGCAGCAU AAACUCCGUG         50

UGCCCAGACG ACGAGCGGGA                                          70

(2) INFORMATION FOR SEQ ID NO:66:

(i) SEQUENCE CHARACTERISTICS:
          (A) LENGTH: 70 nucleotides
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: All C's are 2'-NH2 cytosine (ix) FEATURE:
          (D) OTHER INFORMATION: All U's are 2'-NH2 uracil (xi) SEQUENCE DESCRIPTION: SEQ ID NO:66:

```
GGGAGGACGA UGCGGCAGUA AUCUUGGUAU CAAGAUUACU GGGAUGUGCG        50

UGCCCAGACG ACGAGCGGGA                                         70

(2) INFORMATION FOR SEQ ID NO:67:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION:  All C's are 2'-NH2 cytosine (ix) FEATURE:
         (D) OTHER INFORMATION:  All U's are 2'-NH2 uracil (xi) SEQUENCE DESCRIPTION: SEQ ID NO:67:

GGGAGGACGA UGCGGCAUAU CAUGGUGAUC UUGAUCCAAU AACCGUGAUU        50

GUGCCCAGAC GACGAGCGGG A                                       71

(2) INFORMATION FOR SEQ ID NO:68:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION:  All C's are 2'-NH2 cytosine (ix) FEATURE:
         (D) OTHER INFORMATION:  All U's are 2'-NH2 uracil (xi) SEQUENCE DESCRIPTION: SEQ ID NO:68:

GGGAGGACGA UGCGGCAGUG UGAUUAACAU AGCGGAUUAA CAACACUGUC        50

GUGGGCAGAC GACGAGCGGG A                                       71

(2) INFORMATION FOR SEQ ID NO:69:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION:  All C's are 2'-NH2 cytosine (ix) FEATURE:
         (D) OTHER INFORMATION:  All U's are 2'-NH2 uracil (xi) SEQUENCE DESCRIPTION: SEQ ID NO:69:

GGGAGGACGA UGCGGGCAAG AUCAAUCGGA UCAACACAAC GUUGAUCCGC        50

CUGCCCAGAC GACGAGCGGG A                                       71

(2) INFORMATION FOR SEQ ID NO:70:

(i) SEQUENCE CHARACTERISTICS:
        (A) LENGTH: 71 nucleotides
        (B) TYPE: nucleic acid
```

(C) STRANDEDNESS: single
        (D) TOPOLOGY: linear (ii) MOLECULE TYPE: RNA (ix) FEATURE:
        (D) OTHER INFORMATION:   All C's are 2'-NH2 cytosine (ix) FEATURE:
        (D) OTHER INFORMATION:   All U's are 2'-NH2 uracil (xi) SEQUENCE DESCRIPTION: SEQ ID NO:70:

GGGAGGACGA UGCGGCAGAU CUACAAUCAG AUUGACUAAU CAUGAUCCGC         50

CUGCCCAGAC GACGAGCGGG A                                        71

(2) INFORMATION FOR SEQ ID NO:71:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:   All C's are 2'-NH2 cytosine (ix) FEATURE:
        (D) OTHER INFORMATION:   All U's are 2'-NH2 uracil (xi) SEQUENCE DESCRIPTION: SEQ ID NO:71:

GGGAGGACGA UGCGGCAUGA ACUGAUAAUA AGGUUCAUAG CUUGAGGGUG         50

UUGGCCAGAC GACGAGCGGG A                                        71

(2) INFORMATION FOR SEQ ID NO:72:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:   All C's are 2'-NH2 cytosine (ix) FEATURE:
        (D) OTHER INFORMATION:   All U's are 2'-NH2 uracil (xi) SEQUENCE DESCRIPTION: SEQ ID NO:72:

GGGAGGACGA UGCGGCUAAU GAGCUUGAUA ACAGGAUGUU AUCAAGCCGG         50

CUGUACAGAC GACGAGCGGG A                                        71

(2) INFORMATION FOR SEQ ID NO:73:

(i) SEQUENCE CHARACTERISTICS:
        (A) LENGTH: 70 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:   All C's are 2'-NH2 cytosine (ix) FEATURE:
        (D) OTHER INFORMATION:   All U's are 2'-NH2 uracil (xi) SEQUENCE DESCRIPTION: SEQ ID NO:73:

GGGAGGACGA UGCGGCAUGU ACAUAGUAUG ACUCGUGAUC UGCCUCCAUG         50

GUCCCAGACG ACGAGCGGGA                                          70

(2) INFORMATION FOR SEQ ID NO:74:

(i) SEQUENCE CHARACTERISTICS:
         (A) LENGTH: 71 nucleotides
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:74:

GGGAGGACGA UGCGGCAGUG GUACCUGAGU ACCACUAUAG CUGGAUAUAU         50

GUGUCCAGAC GACGAGCGGG A                                        71

(2) INFORMATION FOR SEQ ID NO:75:

(i) SEQUENCE CHARACTERISTICS:
         (A) LENGTH: 71 nucleotides
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:75:

GGGAGGACGA UGCGGAUUUU UCAACGCUUU ACACGCACAC UGAUUUAGUU         50

AUGGGCAGAC GACGAGCGGG A                                        71

(2) INFORMATION FOR SEQ ID NO:76:

(i) SEQUENCE CHARACTERISTICS:
         (A) LENGTH: 70 nucleotides
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:76:

GGGAGGACGA UGCGGCAUAG CUAAAUAACA CUAACUAUGC CAAACGUCCG         50

UGUACAGACG ACGAGCGGGA                                          70

(2) INFORMATION FOR SEQ ID NO:77:

(i) SEQUENCE CHARACTERISTICS:
         (A) LENGTH: 71 nucleotides (B) TYPE: nucleic acid
         (C) STRANDEDNESS: single
         (D) TOPOLOGY: linear (ii) MOLECULE TYPE: RNA (ix) FEATURE:
         (D) OTHER INFORMATION:  All C's are 2'-NH2 cytosine (ix) FEATURE:
         (D) OTHER INFORMATION:  All U's are 2'-NH2 uracil (xi) SEQUENCE DESCRIPTION: SEQ ID NO:77:

GGGAGGACGA UGCGGCAUGA ACUGAUAAUA AGGUUCAUAG CUUGAGGGUG           50

UUGGCCAGAC GACGAGCGGG A                                         71

(2) INFORMATION FOR SEQ ID NO:78:

(i) SEQUENCE CHARACTERISTICS:
         (A) LENGTH: 71 nucleotides
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION:  All C's are 2'-NH2 cytosine (ix) FEATURE:
         (D) OTHER INFORMATION:  All U's are 2'-NH2 uracil (xi) SEQUENCE DESCRIPTION: SEQ ID NO:78:

GGGAGGACGA UGCGGUAGGA CGAAACAUAG UCUACCAGCA GCCUCCAAGC           50

CCCCCCAGAC GACGAGCGGG A                                         71

(2) INFORMATION FOR SEQ ID NO:79:

(i) SEQUENCE CHARACTERISTICS:
         (A) LENGTH: 71 nucleotides
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION:  All C's are 2'-NH2 cytosine (ix) FEATURE:
         (D) OTHER INFORMATION:  All U's are 2'-NH2 uracil (xi) SEQUENCE DESCRIPTION: SEQ ID NO:79:

GGGAGGACGA UGCGGCAGUA AUCUUGGUAU CAAGAUUACU GGGAUCUGUC           50

GUGCCCAGAC GACGAGCGGG A                                         71

(2) INFORMATION FOR SEQ ID NO:80:

(i) SEQUENCE CHARACTERISTICS:
         (A) LENGTH: 69 nucleotides
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION:  All C's are 2'-NH2 cytosine (ix) FEATURE:
         (D) OTHER INFORMATION:  All U's are 2'-NH2 uracil (xi) SEQUENCE DESCRIPTION: SEQ ID NO:80:

GGGAGGACGA UGCGGCAAGU AGUGUACAUA CAAUGCCAAG UCUCCCGGGU          50

GUACAGACGA CGAGCGGGA                                            69

(2) INFORMATION FOR SEQ ID NO:81:

(i) SEQUENCE CHARACTERISTICS:
            (A) LENGTH: 71 nucleotides
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All C's are 2'-NH2 cytosine (ix) FEATURE:
            (D) OTHER INFORMATION:  All U's are 2'-NH2 uracil (xi) SEQUENCE DESCRIPTION: SEQ ID NO:81:

GGGAGGACGA UGCGGCAGUA AUCUUGGUAU CAAGAUUACU GGGAUCUGUC          50

GUGCCCAGAC GACGAGCGGG A                                         71

(2) INFORMATION FOR SEQ ID NO:82:

(i) SEQUENCE CHARACTERISTICS:
            (A) LENGTH: 70 nucleotides
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All C's are 2'-NH2 cytosine (ix) FEATURE:
            (D) OTHER INFORMATION:  All U's are 2'-NH2 uracil (xi) SEQUENCE DESCRIPTION: SEQ ID NO:82:

GGGAGGACGA UGCGGCAGUA GGGAUCUUGA GAAGUACUAC UGCAGCCCUG          50

UGCCCAGACG ACGAGCGGGA                                           70

(2) INFORMATION FOR SEQ ID NO:83:

(i) SEQUENCE CHARACTERISTICS:
            (A) LENGTH: 71 nucleotides
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All C's are 2'-NH2 cytosine (ix) FEATURE:
            (D) OTHER INFORMATION:  All U's are 2'-NH2 uracil (xi) SEQUENCE DESCRIPTION: SEQ ID NO:83:

GGGAGGACGA UGCGGCAUGA UAAUGGAUUA CAUCAUGAAG CUUAAGACUC          50

CUGUGCAGAC GACGAGCGGG A                                         71

(2) INFORMATION FOR SEQ ID NO:84:

(i) SEQUENCE CHARACTERISTICS:

(A) LENGTH: 71 nucleotides
    (B) TYPE: nucleic acid
    (C) STRANDEDNESS: single
    (D) TOPOLOGY: linear (ii) MOLECULE TYPE: RNA (ix) FEATURE:
    (D) OTHER INFORMATION:  All C's are 2'-NH2 cytosine (ix) FEATURE:
    (D) OTHER INFORMATION:  All U's are 2'-NH2 uracil (xi) SEQUENCE DESCRIPTION: SEQ ID NO:84:

GGGAGGACGA UGCGGAAUCA AUACCGUAAG UCCCUGUAAC UAGUUAGGUU        50

GUGCCCAGAC GACGAGCGGG A        71

(2) INFORMATION FOR SEQ ID NO:85:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All C's are 2'-NH2 cytosine (ix) FEATURE:
        (D) OTHER INFORMATION:  All U's are 2'-NH2 uracil (xi) SEQUENCE DESCRIPTION: SEQ ID NO:85:

GGGAGGACGA UGCGGCAUGC CAUAGUUAUA CCAAUGAUGU GAUGUAGGUG        50

UGCCUCAGAC GACGAGCGGG A        71

(2) INFORMATION FOR SEQ ID NO:86:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All C's are 2'-NH2 cytosine (ix) FEATURE:
        (D) OTHER INFORMATION:  All U's are 2'-NH2 uracil (xi) SEQUENCE DESCRIPTION: SEQ ID NO:86:

GGGAGGACGA UGCGGCAAUA GAUAUCAAGC AACCUCCUAG UCAUGGACAU        50

GUUCCCAGAC GACGAGCGGG A        71

(2) INFORMATION FOR SEQ ID NO:87:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All C's are 2'-NH2 cytosine (ix) FEATURE:

(D) OTHER INFORMATION: All U's are 2'-NH2 uracil (xi) SEQUENCE DESCRIPTION: SEQ ID NO:87:

GGGAGGACGA UGCGGCUAAU GAGCUUGAUA ACAGGAUGUU AUCAAGCCGG          50

CUGUGCAGAC GACGAGCGGG A          71

(2) INFORMATION FOR SEQ ID NO:88:

(i) SEQUENCE CHARACTERISTICS:
        (A) LENGTH: 70 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:88:

GGGAGGACGA UGCGGCAGUA AUCUUGGUAU CAAGAUUACU GGGAUGUGCG          50

UGCCCAGACG ACGAGCGGGA          70

(2) INFORMATION FOR SEQ ID NO:89:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:89:

GGGAGGACGA UGCGGCACCU AUAUGUGCAU AGUUGCAUGA UCUAACCAUG          50

UGCCCCAGAC GACGAGCGGG A          71

(2) INFORMATION FOR SEQ ID NO:90:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:90:

GGGAGGACGA UGCGGCAUAG UCACAAUUGA UUAGCUAGCU GCAUAGGGUG          50

UUGGACAGAC GACGAGCGGG A          71

(2) INFORMATION FOR SEQ ID NO:91:

(i) SEQUENCE CHARACTERISTICS:
    (A) LENGTH: 70 nucleotides
    (B) TYPE: nucleic acid
    (C) STRANDEDNESS: single
    (D) TOPOLOGY: linear (ii) MOLECULE TYPE: RNA (ix) FEATURE:
    (D) OTHER INFORMATION: All C's are 2'-NH2 cytosine (ix) FEATURE:
    (D) OTHER INFORMATION: All U's are 2'-NH2 uracil (xi) SEQUENCE DESCRIPTION: SEQ ID NO:91:

GGGAGGACGA UGCGGCAUAA GCAUAUGUAC AUCCUAACCU CCUGAUGUUG          50

UGCCCAGACG ACGAGCGGGA                                          70

(2) INFORMATION FOR SEQ ID NO:92:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:92:

GGGAGGACGA UGCGGCAUAU GAAGAGCUUG CAAGUUACCU CCGAAUAAGU          50

GUCCCCAGAC GACGAGCGGG A                                        71

(2) INFORMATION FOR SEQ ID NO:93:

(i) SEQUENCE CHARACTERISTICS:
        (A) LENGTH: 69 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:93:

GGGAGGACGA UGCGGCAUAG UGUAGUAGAU AUGGAUGCCU GUACGUCCCU          50

GCCCAGACGA CGAGCGGGA                                           69

(2) INFORMATION FOR SEQ ID NO:94:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
              (D) OTHER INFORMATION:  All U's are 2'-NH2 uracil (xi) SEQUENCE DESCRIPTION: SEQ ID NO:94:

GGGAGGACGA UGCGGCAUAG CUGUAUACCU GAAGUCGAUA AGUACUCCCG        50

UGCCCCAGAC GACGAGCGGG A        71

(2) INFORMATION FOR SEQ ID NO:95:

(i) SEQUENCE CHARACTERISTICS:
              (A) LENGTH: 71 nucleotides
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION:  All C's are 2'-NH2 cytosine (ix) FEATURE:
              (D) OTHER INFORMATION:  All U's are 2'-NH2 uracil (xi) SEQUENCE DESCRIPTION: SEQ ID NO:95:

GGGAGGACGA UGCGGCAAUA CUAACAUAGC GUCCUAGGAU UAGGUCUCCC        50

AUGGCCAGAC GACGAGCGGG A        71

(2) INFORMATION FOR SEQ ID NO:96:

(i) SEQUENCE CHARACTERISTICS:
              (A) LENGTH: 71 nucleotides
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION:  All C's are 2'-NH2 cytosine (ix) FEATURE:
              (D) OTHER INFORMATION:  All U's are 2'-NH2 uracil (xi) SEQUENCE DESCRIPTION: SEQ ID NO:96:

GGGAGGACGA UGCGGCAUAA CGUGAAUAUC UGAGUACUAA CCGUGUCGUU        50

GUGCCCAGAC GACGAGCGGG A        71

(2) INFORMATION FOR SEQ ID NO:97:

(i) SEQUENCE CHARACTERISTICS:
              (A) LENGTH: 69 nucleotides
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION:  All C's are 2'-NH2 cytosine (ix) FEATURE:
              (D) OTHER INFORMATION:  All U's are 2'-NH2 uracil (xi) SEQUENCE DESCRIPTION: SEQ ID NO:97:

GGGAGGACGA UGCGGCAUAU GUGUGUAUAG UCCUACACAU AUGCGUGUGU        50

GUGCAGACGA CGAGCGGGA        69

(2) INFORMATION FOR SEQ ID NO:98:

(i) SEQUENCE CHARACTERISTICS:
    (A) LENGTH: 70 nucleotides
    (B) TYPE: nucleic acid
    (C) STRANDEDNESS: single
    (D) TOPOLOGY: linear (ii) MOLECULE TYPE: RNA (ix) FEATURE:
    (D) OTHER INFORMATION:  All C's are 2'-NH2 cytosine (ix) FEATURE:
    (D) OTHER INFORMATION:  All U's are 2'-NH2 uracil (xi) SEQUENCE DESCRIPTION: SEQ ID NO:98:

GGGAGGACGA UGCGGCAUCC AUAAUACUCC UAAAGACCUC AUCAACUCCU          50

GCUGCAGACG ACGAGCGGGA                                          70

(2) INFORMATION FOR SEQ ID NO:99:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All C's are 2'-NH2 cytosine (ix) FEATURE:
        (D) OTHER INFORMATION:  All U's are 2'-NH2 uracil (xi) SEQUENCE DESCRIPTION: SEQ ID NO:99:

GGGAGGACGA UGCGGCAUAA GAUCAGUAUA CAGAUAACCG AUAAGACCUU          50

CCCCCCAGAC GACGAGCGGG A                                        71

(2) INFORMATION FOR SEQ ID NO:100:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All C's are 2'-NH2 cytosine (ix) FEATURE:
        (D) OTHER INFORMATION:  All U's are 2'-NH2 uracil (xi) SEQUENCE DESCRIPTION: SEQ ID NO:100:

GGGAGGACGA UGCGGCACUG AGAGUGUAAG UAGAUAACCA AGUCCUCUGG          50

GUGCCCAGAC GACGAGCGGG A                                        71

(2) INFORMATION FOR SEQ ID NO:101:

(i) SEQUENCE CHARACTERISTICS:
        (A) LENGTH: 71 nucleotides
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All C's are 2'-NH2 cytosine (ix) FEATURE:
             (D) OTHER INFORMATION: All U's are 2'-NH2 uracil (xi) SEQUENCE DESCRIPTION: SEQ ID NO:101:

GGGAGGACGA UGCGGCUAGU AACCAUGACU AGCUAAUAGG GCUAUCCGUC          50

CUGGCCAGAC GACGAGCGGG A                                         71

(2) INFORMATION FOR SEQ ID NO:102:

(i) SEQUENCE CHARACTERISTICS:
             (A) LENGTH: 70 nucleotides
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION: All C's are 2'-NH2 cytosine (ix) FEATURE:
             (D) OTHER INFORMATION: All U's are 2'-NH2 uracil (xi) SEQUENCE DESCRIPTION: SEQ ID NO:102:

GGGAGGACGA UGCGGCACAA UUCAAUAAGU GCACCACUAA CUAAUAUCGU          50

GCUACAGACG ACGAGCGGGA                                           70

(2) INFORMATION FOR SEQ ID NO:103:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: DNA (ix) FEATURE:
             (D) OTHER INFORMATION: N equal 3 biotin molecule (xi) SEQUENCE DESCRIPTION: SEQ ID NO:103:

NTCCCGCTCG TCGTCTG                                              17

(2) INFORMATION FOR SEQ ID NO:104:

(i) SEQUENCE CHARACTERISTICS:
             (A) LENGTH: 15 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:104:

GGGAGGACGA TGCGG                                                15

(2) INFORMATION FOR SEQ ID NO:105:

(i) SEQUENCE CHARACTERISTICS:
             (A) LENGTH: 32 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:105:

TAATACGACT CACTATAGGG AGGACGATGC GG                             32

(2) INFORMATION FOR SEQ ID NO:106:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:106:

TCCCGCTCGT CGTCTG                                                  16

(2) INFORMATION FOR SEQ ID NO:107:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: N at position 4, 6, 8 and 11 is
            79% C; 7% A; 7% T and 7% G (ix) FEATURE:
        (D) OTHER INFORMATION: N at position 5, 9 and 12 is 79%
            G, 7% A, 7% T and 7% C (ix) FEATURE:
        (D) OTHER INFORMATION: N at position 7, 10 and 13 is
            79% T; 7% A; 7% C and 7% G (xi) SEQUENCE DESCRIPTION: SEQ ID NO:107:

TCCNNNNNNN NNNCTG                                                  16

(2) INFORMATION FOR SEQ ID NO:108:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:108:

GGGAGGACAA CTGACACTTG TGCCGCATCG TCCTCCC                            37

(2) INFORMATION FOR SEQ ID NO:109:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:109:

GGGAGGACGA TGCGGGACAG GTGGTGTGGC AGGGTAGGTC ATGTTACTAA              50

TTCATCAGAC GACGAGCGGG                                              70

(2) INFORMATION FOR SEQ ID NO:110:

(i) SEQUENCE CHARACTERISTICS:
        (A) LENGTH: 68 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:110:

GGGAGGACGA TGCGGTGGAG AGCAATATGT GTACAAGTTA GCCTAGATGT           50

GTTCAGACGA CGAGCGGG                                              68

(2) INFORMATION FOR SEQ ID NO:111:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:111:

GGGAGGACGA TGCGGTGACC AAGTACCAGA GTACGCACCA TCTAATTCCC           50

ACACTCAGAC GACAAGCGGG                                            70

(2) INFORMATION FOR SEQ ID NO:112:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:112:

GGGAGGACGA TGCGGTGACA ACACAGTATC CTATAAAGTC TCACCCTTAT           50

GCCACAGACG ACGAGCGGG                                             69

(2) INFORMATION FOR SEQ ID NO:113:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:113:

GGGAGGACGA TGCGGGACTG CGTATCAACG CGGTGAAACC TAACCTCATC           50

TTGATCAGAC GACGCGCGGG                                            70

(2) INFORMATION FOR SEQ ID NO:114:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:114:

GGGCGGACGT AGCGGTACGT GGCTTTAGCC GGGATTGACA GAATCCCTAT           50

CACACCAGAC GGCGAGCGGG                                            70

(2) INFORMATION FOR SEQ ID NO:115:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:115:

```
GGGAGGACGA TGCGGTGGGG GTGATGATAG GTCTAATTAG TCTTACGTGT          50

GGACAGACGA CGAGCGGG                                             68
```

(2) INFORMATION FOR SEQ ID NO:116:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:116:

```
GGAGGACGAT GCGGCCTACA CGGAGGTTGT TCTCAATGAA CTATCCTTGT          50

ACCTCAGACG ACGAGCGGG                                            69
```

(2) INFORMATION FOR SEQ ID NO:117:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:117:

```
GGGAGGACGA TGCGGGTGAG AAGGTGAGTT TAGTTTAGAT ATATCAAGTA          50

TGGCCAGACG ACGAGCGGG                                            69
```

(2) INFORMATION FOR SEQ ID NO:118:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:118:

```
GGGAGGACGA TGCGGCACCG CTATGCAGAT CTTATGCACC CATCATGCCA          50

CCACACAGAC AACGAGCGGG                                           70
```

(2) INFORMATION FOR SEQ ID NO:119:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:119:

```
GGGAGGACGA TGCGGGCCGT AGTGTGTGGT ATGTACAACA ATGCATCTCA              50

CATGCAGACG ACGAGCGGG                                                 69
```

(2) INFORMATION FOR SEQ ID NO:120:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:120:

```
CCCAGGACGA TGCGGCAACG AGCATGACGT GAATGCCTTA TCGACCCACC              50

CACCACAGAC GACGAGCGGG                                                70
```

(2) INFORMATION FOR SEQ ID NO:121:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:121:

```
GGGAGGACGA TGCGGTGACG ACATGCCAAT GTAAGAACAT GCTTACCCCT              50

GTTGACAGAC GGCGAGCGGG                                                70
```

(2) INFORMATION FOR SEQ ID NO:122:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:122:

```
GGGAGGACGA TGCGGTGGAG GTGATGGTGT GATCAAACTT GCCTATTTAG              50

GGACAGACGA CGAGCGGG                                                  68
```

(2) INFORMATION FOR SEQ ID NO:123:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:123:

```
GGGAGGACGA TGCGGCACGA TGGTTAGGCG GGCCTTGAGG CTAATAATGT              50

TGTTACAGAC GACGAGCGGG                                                70
```

(2) INFORMATION FOR SEQ ID NO:124:

(i) SEQUENCE CHARACTERISTICS:
        (A) LENGTH: 69 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:124:

GGGAGGACGA TGCGGTGCTG CGAAGCACTA TGATTAGATA GTGTACCATT          50

TGGACAGACG ACGAGCGGG                                           69

(2) INFORMATION FOR SEQ ID NO:125:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:125:

GGGAGGACGA TGCGGTAGTA GGGGGAGATT GTTGTGTTAG GTGAGCTTAG          50

TTTCAGACGA CGAGCGGG                                            68

(2) INFORMATION FOR SEQ ID NO:126:

(i) SEQUENCE CHARACTERISTICS:
        (A) LENGTH:  70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:126:

GGGAGGACGA TGCGGTGTCT TGCGGGTTAA GGCATGCTTA CTATGTCGGT          50

GTGACCAGAC GACGAGCGGG                                          70

(2) INFORMATION FOR SEQ ID NO:127:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:127:

GGGCGGACGA TGCGGCAACC ACAGGATCAC CCTGTCAAAT CGCTACCCAC          50

ACCTACAGAC GACGAGCGGG                                          70

(2) INFORMATION FOR SEQ ID NO:128:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:128:

GGGAGGACGA TGCGGCCATG ACAGAATGTC TGCAGAGCTA ATCTTGGTCA          50

CTGATCAGAC GACGAGCGGG                                          70

(2) INFORMATION FOR SEQ ID NO:129:

(i) SEQUENCE CHARACTERISTICS:
    (A) LENGTH: 68 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:129:

GGGAGGACGA TGCGGTGGGG GTGTTGTATG TGTTATGTGC CAAATGACTT        50

GTACAGACGA CGAGCGGG        68

(2) INFORMATION FOR SEQ ID NO:130:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:130:

GGGAGGACGA TGCGGTGGGG ACATGGGTGT TATAATTGGT TTGGTTCAAC        50

CATCAGACGA CGAGCGGG        68

(2) INFORMATION FOR SEQ ID NO:131:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:131:

GGGAGGACGA TGCGGACCTG CAAGCACCCT TATCACACAG CCACTCTATA        50

CTCATCAGAC GAGGAGCGGG        70

(2) INFORMATION FOR SEQ ID NO:132:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:132:

GGGAGGACGA TGCGGCCTCT GCGGCAGAAG AAGATGTCAC CATCTTTACC        50

TTGGGCAGAC GAGGAGCGGG        70

(2) INFORMATION FOR SEQ ID NO:133:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:133:

GGGAGGACGA TGCGGCACCA TCGTACGCAC CACTATTCCA TCAACTCTCT        50

CTGAACAGAC AACGAGTATT ACAAATACCA GACCCTTTAG CCCTATCCCT        100

ACAGACGACG AGCGGG        116

(2) INFORMATION FOR SEQ ID NO:134:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:134:

GGGAGGACGA TGCGGTACGA CAGGCCACGA TAGCTTACGC CACCCACAGC        50

ACTATCAGAC GACGAGCGGG        70

(2) INFORMATION FOR SEQ ID NO:135:

(i) SEQUENCE CHARACTERISTICS:
        (A) LENGTH: 63base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:135:

GGGAGGACGA TGCGGCCCAT GGTGTGGGTG ACAACATGCA TCAGGTAAGA        50

TGCTACAGAC GAC        63

(2) INFORMATION FOR SEQ ID NO:136:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:136:

GGGAGGACGA TGCGGCAACG AGTATTACAA ATACCAGACC CTTACCCTAT        50

CCCTACAGAC GACGAGCGGG        70

(2) INFORMATION FOR SEQ ID NO:137:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:137:

GGGAGGACGA TGCGGTACAG TCGTAAGACA CAAGAAGCAA TCTTGTTATG        50

GTTGACAGAC GACGAGCTGG        70

(2) INFORMATION FOR SEQ ID NO:138:

(i) SEQUENCE CHARACTERISTICS:
        (A) LENGTH: 70 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:138:

GGGAGGACGA TGCGGTAGGG GGGGTGTAAC TGGGTAATCC ATAAATTGTC           50

TGACTCAGAC GACGAGCGGG                                           70

(2) INFORMATION FOR SEQ ID NO:139:

(i) SEQUENCE CHARACTERISTICS:
            (A) LENGTH: 68 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:139:

GGGAGGACGA TGCGGTGTGG GTAGGATGAA AGGTCGTTAC ATTGTGGTCT           50

GTACAGACGA CGAGCGGG                                             68

(2) INFORMATION FOR SEQ ID NO:140:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:140:

GGGAGGACGA TGCGGCGACG AGAGTGCCAA ACTCCTTTAT CTACCCTCCA           50

CATGACAGAC GACGAGCGGG                                           70

(2) INFORMATION FOR SEQ ID NO:141:

(i) SEQUENCE CHARACTERISTICS:
            (A) LENGTH: 68 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:141:

GGGAGGACGA TGCGGTACGG TGGTTAGGCA GGATTAGGTC TTATTTGTTG           50

TGCAACAGAC GACGAGGG                                             68

(2) INFORMATION FOR SEQ ID NO:142:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:142:

GGGAGGACGA TGCGGTACAC CATGACTCAT GGATACTTCG TATTATTACT           50

TCGCACAGAC GACGGGCGGG                                           70

(2) INFORMATION FOR SEQ ID NO:143:

(i) SEQUENCE CHARACTERISTICS:
    (A) LENGTH: 69 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:143:

GGAGGACGAT GCGGTACACA CCACCCAACA ATTCTTATCA CGACAACCAC         50

TTATCAGACG ACGAGCGGG                                          69

(2) INFORMATION FOR SEQ ID NO:144:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:144:

GGGAGGACGA TGCGGTCAAC CATTGATTAT GACTATCACC CTATCACCCA         50

CCCATCAGAC GCCGAGGGGG                                         70

(2) INFORMATION FOR SEQ ID NO:145:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:145:

GGGAGGACGA TGCGGGACTG TGGACTTAGA ACACGCTGTG TGAACAGCTA         50

CCTATCAGAC GACGGGCGGG                                         70

(2) INFORMATION FOR SEQ ID NO:146:

(i) SEQUENCE CHARACTERISTICS:
        (A) LENGTH:  67 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:146:

GGGAGGACGA TGCGGTGGGG ACAGGTGTTC GTAAGTTGAG TTAGCTGATT         50

GCCAGACGAC GAGCGGG                                            67

(2) INFORMATION FOR SEQ ID NO:147:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:147:

GGGAGGACGA TGCGGTGGGA TGTACGGTGA ACACAAGNNN ATTATGGATC         50

```
ATGGTCAGAC GACGAGG                                                       67

(2) INFORMATION FOR SEQ ID NO:148:

(i) SEQUENCE CHARACTERISTICS:
         (A) LENGTH: 67 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:148:

GGGAGGACGA TGCGGGACGC TACTGGAGCC CTTATAACGC CACATTACAC                   50

ACACACAGGC GACGAGC                                                       67

(2) INFORMATION FOR SEQ ID NO:149:

(i) SEQUENCE CHARACTERISTICS:
         (A) LENGTH: 69 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:149:

GGGAGGACGA TGCGGGTGGA GGTGATGTAG TAAGAAATAT AGTAAAGTGT                   50

CCTGCAGACG ACGAGCGGG                                                     69

(2) INFORMATION FOR SEQ ID NO:150:

(i) SEQUENCE CHARACTERISTICS:
         (A) LENGTH: 70 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:150:

GGGAGGACGA TGCGGCGCTG TCATATGGCA GTCAATGACG TACCCTGGTA                   50

CTACTCAGAC GACGAGCGGG                                                    70

(2) INFORMATION FOR SEQ ID NO:151:

(i) SEQUENCE CHARACTERISTICS:
         (A) LENGTH: 68 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:151:

GAGGACGATG CGGTACTGGT CTTACGGTGG GTAAATCTAA CAGACCCGAT                   50

CTACAGACGC CGAGCGGG                                                      68

(2) INFORMATION FOR SEQ ID NO:152:

(i) SEQUENCE CHARACTERISTICS:
         (A) LENGTH: 69 base pairs
         (B) TYPE: nucleic acid
         (C) STRANDEDNESS: single
         (D) TOPOLOGY: linear
```

```
        (ii) MOLECULE TYPE: DNA (xi) SEQUENCE DESCRIPTION: SEQ ID NO:152:

GGAGGACGAT GCGGCCAGAA GTGATGAACG CGATCTTTTA GATCTATTCC            50

TCTACAGACG GCGAGCGGG                                              69

(2) INFORMATION FOR SEQ ID NO:153:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:153:

GGGAGGACGA TGCGGCTGCA AACTATCGCA GATAGAGCGT TAGATCATTC            50

TTCCACAGAC GACGACCGGG                                             70

(2) INFORMATION FOR SEQ ID NO:154:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:154:

GGGAGGACGA TGCGGCAACG AACAGGTTTA ACCTGACAAC ACTACCCCTA            50

CCATGCAGAC GACGAGCGGG                                             70

(2) INFORMATION FOR SEQ ID NO:155:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:155:

GGGAGGACGA TGCGGGCACA GACGAAGTCG CAACTTGATT GCTATCCACC            50

AGACACAGAC GACGAGCGGG                                             70

(2) INFORMATION FOR SEQ ID NO:156:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:156:

GGAGGACGAT GCGGTGACGA GGATTACATC CCTACGATAA CAGTACTCTA            50

TCTGCAGACG ACGAGCGGG                                              69

(2) INFORMATION FOR SEQ ID NO:157:

(i) SEQUENCE CHARACTERISTICS:
```

(A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:157:

GGGAGGACGA TGCGGCACGT CCGGAACATT TATGTGAGTT TTATAACACG           50

TTGAACAGAC GACGAGCGGG                                            70

(2) INFORMATION FOR SEQ ID NO:158:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All C's are 2'-NH2 cytosine (ix) FEATURE:
        (D) OTHER INFORMATION:  All U's are 2'-NH2 uracil (xi) SEQUENCE DESCRIPTION: SEQ ID NO:158:

GGGAGGACUA UGCCUGUCAG CCUCUAUGCC GCAUCGUCCU CCCUAUAGUG           50

AGUCGUAUUG GGCUAGAGCG GCCGCCACC                                  79

(2) INFORMATION FOR SEQ ID NO:159:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All C's are 2'-NH2 cytosine (ix) FEATURE:
        (D) OTHER INFORMATION:  All U's are 2'-NH2 uracil (xi) SEQUENCE DESCRIPTION: SEQ ID NO:159:

GGGAGGACGA UGCGGCACAG UGAUGUCAUG AUCAUAGGUA UACAUAUGCG           50

UGACAGACGA CGCGCGGG                                              68

(2) INFORMATION FOR SEQ ID NO:160:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ix) FEATURE:
        (D) OTHER INFORMATION:  All C's are 2'-NH2 cytosine (ix) FEATURE:
        (D) OTHER INFORMATION:  All U's are 2'-NH2 uracil (ii) MOLECULE TYPE: RNA (xi) SEQUENCE DESCRIPTION: SEQ ID NO:160:

GGGAGGACGA UGCGGCACCA UGGAUGUAGG GUGAUGGUUC AUGGGACUCA           50

```
CGUGCAGACG ACGAGCGGG                                                      69

(2) INFORMATION FOR SEQ ID NO:161:

(i) SEQUENCE CHARACTERISTICS:
          (A) LENGTH: 70 base pairs
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION:  All C's are 2'-NH2 cytosine (ix) FEATURE:
          (D) OTHER INFORMATION:  All U's are 2'-NH2 uracil (xi) SEQUENCE DESCRIPTION: SEQ ID NO:161:

GGGAGGACGA UGCGGCAUCA UAUGAUAAAC ACAUGUCGCG CCCAACCUGA                    50

CCCCACAGAC GACGAGCGGG                                                     70

(2) INFORMATION FOR SEQ ID NO:162:

(i) SEQUENCE CHARACTERISTICS:
          (A) LENGTH: 69 base pairs
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION:  All C's are 2'-NH2 cytosine (ix) FEATURE:
          (D) OTHER INFORMATION:  All U's are 2'-NH2 uracil (xi) SEQUENCE DESCRIPTION: SEQ ID NO:162:

GGGAGGACGA UGCGGCAGUA GCAAUAAGAC UACUGUAGGG UUGAAUCCGU                    50

GCUACAGACG ACGAGCGGG                                                      69

(2) INFORMATION FOR SEQ ID NO:163:

(i) SEQUENCE CHARACTERISTICS:
          (A) LENGTH: 67 base pairs
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION:  All C's are 2'-NH2 cytosine (ix) FEATURE:
          (D) OTHER INFORMATION:  All U's are 2'-NH2 uracil (xi) SEQUENCE DESCRIPTION: SEQ ID NO:163:

GGGAGGACGA UGCGGCACUA UGGUGCAGGG UGAUGUGUCA GGUUCUCCAG                    50

UACAGACGAC GAGCGGG                                                        67

(2) INFORMATION FOR SEQ ID NO:164:

(i) SEQUENCE CHARACTERISTICS:
          (A) LENGTH: 67 base pairs
          (B) TYPE: nucleic acid
          (C) STRANDEDNESS: single
          (D) TOPOLOGY: linear
```

(ii) MOLECULE TYPE: RNA (ix) FEATURE:
             (D) OTHER INFORMATION:  All C's are 2'-NH2 cytosine (ix) FEATURE:
             (D) OTHER INFORMATION:  All U's are 2'-NH2 uracil (xi) SEQUENCE DESCRIPTION: SEQ ID NO:164:

GGGAGGACGA UGCGGUACCG UGAUGUCAUG AUCAUAGGUA UACAUAUGCG          50

UACAGACGAC GAGCGGG                                              67

(2) INFORMATION FOR SEQ ID NO:165:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (ii) MOLECULE TYPE: RNA (ix) FEATURE:
             (D) OTHER INFORMATION:  All C's are 2'-NH2 cytosine (ix) FEATURE:
             (D) OTHER INFORMATION:  All U's are 2'-NH2 uracil (xi) SEQUENCE DESCRIPTION: SEQ ID NO:165:

GGGAGGACUA UGCGGCACCA UGGAUGUAGG GUGAUGGUUC AAGUCCUCCG          50

AUGCCAGACG ACGAGCGGG                                            69

(2) INFORMATION FOR SEQ ID NO:166:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (ii) MOLECULE TYPE: RNA (ix) FEATURE:
             (D) OTHER INFORMATION:  All C's are 2'-NH2 cytosine (ix) FEATURE:
             (D) OTHER INFORMATION:  All U's are 2'-NH2 uracil (xi) SEQUENCE DESCRIPTION: SEQ ID NO:166:

GGGAGGACGA UGCGGCAUAG AGAUGCUGAC AGGCAUAGUC CCAUCUCCUA          50

AGUGCAGACG ACGAGCGGG                                            69

(2) INFORMATION FOR SEQ ID NO:167:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: RNA (ix) FEATURE:
             (D) OTHER INFORMATION:  All C's are 2'-NH2 cytosine (ix) FEATURE:
             (D) OTHER INFORMATION:  All U's are 2'-NH2 uracil (xi) SEQUENCE DESCRIPTION: SEQ ID NO:167:

GGGAGGACGA UGCGGUACCG UGAUGUCAUG AUCAUAGUGA GUCGUAUU            48

(2) INFORMATION FOR SEQ ID NO:168:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:168:

```
GGGAGGACGA UGCGGCAUCU AUGACAAACC UAAUGUGGUC GUCCCUCCCG        50

GACCACAGAC GACGAGGGGG                                         70
```

(2) INFORMATION FOR SEQ ID NO:169:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:169:

```
GGGAGGACGA UGCGGCUGAC UGGGUUGGUU AGGUAAGUAU GUCCGUGUUC        50

AUGAUCAGAC GACGAGCGGG                                         70
```

(2) INFORMATION FOR SEQ ID NO:170:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:170:

```
GGGAGGACGA UGCGGCAGUA GCAAUAAGAC UACUGUAGGG UUGAAUCCGU        50

GCUGCAGACG ACGAGCUGG                                          69
```

(2) INFORMATION FOR SEQ ID NO:171:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
    (D) OTHER INFORMATION: All C's are 2'-NH2 cytosine (ix) FEATURE:
    (D) OTHER INFORMATION: All U's are 2'-NH2 uracil (xi) SEQUENCE DESCRIPTION: SEQ ID NO:171:

GGGAGGACGA UGCGGCAUCU AUGACAAACC UAAUGUGGUC GUCCCUCCCG                50

GACCACAGAA GACGAGCGGG                                                70

(2) INFORMATION FOR SEQ ID NO:172:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:172:

GGGAGGACGA UGCGGCGUAA CAAGCGUGUG UGAGGUCCCC UCCCCCUCAC                50

ACCAUCAGAC GCCGAGCGGG                                                70

(2) INFORMATION FOR SEQ ID NO:173:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:173:

GGGAGGACGA UGCGGCUCAU GUAUGAGGUC UAAGUACGCA UAGUCCCAUC                50

GCAGACAGAC GACGAGCGGG                                                70

(2) INFORMATION FOR SEQ ID NO:174:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:174:

GGGAGGACGA UGCGGCAGUA GCAAUAAGAC UACUGUAGGG AUUGAAUCCG                50

```
UGCUACAGAC GACGAGCGGG                                                    70

(2) INFORMATION FOR SEQ ID NO:175:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All C's are 2'-NH2 cytosine (ix) FEATURE:
        (D) OTHER INFORMATION:  All U's are 2'-NH2 uracil (xi) SEQUENCE DESCRIPTION: SEQ ID NO:175:

GGGAGGACGA UGCGGCAAUG CAAGCCUGCA UGGUGUGAUG GGACUAUGCC                   50

UGUACAGACG ACGAGCGGG                                                     69

(2) INFORMATION FOR SEQ ID NO:176:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All C's are 2'-NH2 cytosine (ix) FEATURE:
        (D) OTHER INFORMATION:  All U's are 2'-NH2 uracil (xi) SEQUENCE DESCRIPTION: SEQ ID NO:176:

GGGAGGACGA UGCGGCAAUA AUCUAGUUGC AUAGUCACCA UCGCAUCCGU                   50

GCAGGCAGAC AACGAGCGGG A                                                  71

(2) INFORMATION FOR SEQ ID NO:177:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All C's are 2'-NH2 cytosine (ix) FEATURE:
        (D) OTHER INFORMATION:  All U's are 2'-NH2 uracil (xi) SEQUENCE DESCRIPTION: SEQ ID NO:177:

GGGAGGACGA UGCGGCUCGA AAUGAAGUGU AAGCUCAAAG CCCACAGUGA                   50

UGUCCAGACG ACGAGCGGG                                                     69

(2) INFORMATION FOR SEQ ID NO:178:

(i) SEQUENCE CHARACTERISTICS:
        (A) LENGTH: 69 base pairs
        (B) TYPE: nucleic acid
        (C) STRANDEDNESS: single
        (D) TOPOLOGY: linear
```

(ii) MOLECULE TYPE: RNA (ix) FEATURE:
            (D) OTHER INFORMATION:  All C's are 2'-NH2 cytosine (ix) FEATURE:
            (D) OTHER INFORMATION:  All U's are 2'-NH2 uracil (xi) SEQUENCE DESCRIPTION: SEQ ID NO:178:

GGGAGGACGA UGCGGCAUAG AGAUGCUGAC AGGCAUAGUC CCAUCUCCUA          50

AGUGCAGACG ACGAGCGGG                                            69

(2) INFORMATION FOR SEQ ID NO:179:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All C's are 2'-NH2 cytosine (ix) FEATURE:
            (D) OTHER INFORMATION:  All U's are 2'-NH2 uracil (xi) SEQUENCE DESCRIPTION: SEQ ID NO:179:

GGGAGGACGA UGCGGCACAU UGAAGAGUGC AAGUGUGCGG CCCACAGUGA          50

UGUACAGACG ACGAGCGGG                                            69

(2) INFORMATION FOR SEQ ID NO:180:

(i) SEQUENCE CHARACTERISTICS:
            (A) LENGTH: 68 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All C's are 2'-NH2 cytosine (ix) FEATURE:
            (D) OTHER INFORMATION:  All U's are 2'-NH2 uracil (xi) SEQUENCE DESCRIPTION: SEQ ID NO:180:

GGGAGGACGA UGCGGCACUA UGGAUGCAGG GUGAUGUGUC AGGUUCUCCG          50

GAACAGACGA CGAGCGGG                                             68

(2) INFORMATION FOR SEQ ID NO:181:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All C's are 2'-NH2 cytosine (ix) FEATURE:
            (D) OTHER INFORMATION:  All U's are 2'-NH2 uracil (xi) SEQUENCE DESCRIPTION: SEQ ID NO:181:

GGGAGGACGA UGCGGCAUAG AGAUGCUGAC AGGCAUAGUC CCAUCUCCUA          50

```
AGUGCCAGAC GACGAGCGGG A                                              71

(2) INFORMATION FOR SEQ ID NO:182:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: RNA FEATURE:
        (D) OTHER INFORMATION:  All C's are 2'-NH2 cytosine (ix) FEATURE:
        (D) OTHER INFORMATION:  All U's are 2'-NH2 uracil (xi) SEQUENCE DESCRIPTION: SEQ ID NO:182:

GGGAGGACGA UGCGGCCUGA UAACCGUCCA GGCUAUUGAG GUGAUAGGUU              50

GGGCAGACGA UGAGCGGG                                                 68

(2) INFORMATION FOR SEQ ID NO:183:

(i) SEQUENCE CHARACTERISTICS:
        (A) LENGTH: 66 base pairs
     (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All C's are 2'-NH2 cytosine (ix) FEATURE:
        (D) OTHER INFORMATION:  All U's are 2'-NH2 uracil (xi) SEQUENCE DESCRIPTION: SEQ ID NO:183:

GGGCGGACGA UGCGGGACGA UUAGUUUGGC AUGUCUGUGG CACCCUCCCC              50

ACAGACGACG AGCGGG                                                   66

(2) INFORMATION FOR SEQ ID NO:184:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All C's are 2'-NH2 cytosine (ix) FEATURE:
        (D) OTHER INFORMATION:  All U's are 2'-NH2 uracil (xi) SEQUENCE DESCRIPTION: SEQ ID NO:184:

GGGAGGACGA UGCGGUACCA CGUGAGCUAC UAAAGUGAUC AAGUUGUAUG              50

CAGACGACGA GCGGG                                                    65

(2) INFORMATION FOR SEQ ID NO:185:

(i) SEQUENCE CHARACTERISTICS:
        (A) LENGTH: 69 base pairs
        (B) TYPE: nucleic acid
        (C) STRANDEDNESS: single
        (D) TOPOLOGY: linear
```

5,998,142

139                                                            140

-continued

```
    (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:185:

GGGAGGACGA UGCGGCUCGA AAUGAAGUGU AAGCUCAAAG CCCACAGUGA          50

UGUCCAGACG ACGAGCGGG                                             69

(2) INFORMATION FOR SEQ ID NO:186:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:186:

GGGAGGACGA UGCGGCAAUG CAAGCCUGCA UUGGUGUGAU GGGACUAUGC          50

CUGUACAGAC GACGAGCGGG A                                         71

(2) INFORMATION FOR SEQ ID NO:187:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:187:

GGGAGGACGA TGCGGCAGCG TCATTTAGGA TTCGTCAGGT TCTACCCGTA          50

GTGTGCAGAC GACGAGCGGG A                                         71

(2) INFORMATION FOR SEQ ID NO:188:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:188:

GGGAGGACGA TGCGGCCTGT GTTGGTTAGT TAACACGCGA AGCTTCCCCG          50

CTCCCCAGAC GACGAGCGGG A                                         71

(2) INFORMATION FOR SEQ ID NO:189:

(i) SEQUENCE CHARACTERISTICS:
        (A) LENGTH: 71 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO:189:

GGGAGGACGA TGCGGCACGT AAGTATCTAC GCGAGCAACA TGCTCTATCT        50

CTCCCCAGAC GACGAGCGGG A                                      71

(2) INFORMATION FOR SEQ ID NO:190:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:190:

GGGAGGACGA TGCGGCACGA CTTCCATGGC AGGGATTTCG GTGAGCCCCC        50

TTAATCAGAC GACGAGCGGG A                                      71

(2) INFORMATION FOR SEQ ID NO:191:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:191:

GGGAGGACGA TGCGGCAGGA ACAGGGGTG CACGGGGAAA TCATGCTTTA         50

TCATCCAGAC GACGAGCGGG A                                      71

(2) INFORMATION FOR SEQ ID NO:192:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:192:

GGGAGGACGA TGCGGCGACG AAGGTTCCAA CGTGGAATGG TTTTCACCCT        50

ACCCGCAGAC GACGAGCGGG A                                      71

(2) INFORMATION FOR SEQ ID NO:193:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:193:

GGGAGGACGA TGCGGCCTGC AGCTGATTCT GCGGGCACTA GCCTACATTC        50

GGTACAGACG ACGAGCGGGA                                        70

(2) INFORMATION FOR SEQ ID NO:194:

(i) SEQUENCE CHARACTERISTICS:
    (A) LENGTH: 71 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:194:

GGGAGGACGA TGCGGCAACG AAGGTTCCCC AGGAATGCGT TACGCTACAG            50

TTGACCAGAC GACGAGCGGG A                                          71

(2) INFORMATION FOR SEQ ID NO:195:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:195:

GGGAGGACGA TGCGGGGCGG TGTGAGAACA CGACACCTAG TGTCTACCAT            50

CTGACCAGAC GACGAGCGGG A                                          71

(2) INFORMATION FOR SEQ ID NO:196:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:196:

GGGAGGACGA TGCGGCAGNN GGNNCAGGTA ATGTGAGTAA CCTCTACTAC            50

TCTGCAGACG ACGAGCGGGA                                            70

(2) INFORMATION FOR SEQ ID NO:197:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:197:

GGGAGGACGA TGCGGCACGT AAGCTGTACC AATTGGTTAA TCACACACTC            50

CCCACAGACG ACGAGCGGGA                                            70

(2) INFORMATION FOR SEQ ID NO:198:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:198:

GGGAGGACGA TGCGGACCAC AGCCACTAGN NGCATCGTCC TCTGCGTCCA            50

```
GACGACGAGC GGGA                                                     64

(2) INFORMATION FOR SEQ ID NO:199:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:199:

GGGAGGACGA TGCGGCACGT CAGTGCTACT TCGGTTCTTT GTCAACCTAT              50

TCCACAGACG ACGAGCGGGA                                               70

(2) INFORMATION FOR SEQ ID NO:200:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:200:

GGGAGGACGA TGCGGTACGC AGAGGACGAT GCGGGCTACT GGCTGTGGTC              50

AGACGACGAG CGGGA                                                    65

(2) INFORMATION FOR SEQ ID NO:201:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:201:

GGGAGGACGA TGCGGCAGGA GACGCTACCC ACCGGTTACA TTGAATATCT              50

CTCCCCAGAC GACGAGCGGG A                                             71

(2) INFORMATION FOR SEQ ID NO:202:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:202:

GGGAGGACGA TGCGGGGGGC GTAGATGACT TAGAACCCTA TTAGTGGCAC              50

ACGCCAGACG ACGAGCGGGA                                               70

(2) INFORMATION FOR SEQ ID NO:203:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:203:

GGGAGGACGA TGCGGGCACA CAAACACAGT GCGAACGGTA GTTCTAATCC          50

TCCTGCAGAC GACGAGCGGG A                                         71

(2) INFORMATION FOR SEQ ID NO:204:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:204:

GGGAGGACGA TGCGGTAGCA GCGGAGGACG ATGCGGTCTT TTGCATCCCC          50

AGACGACGAG CGGGA                                                65

(2) INFORMATION FOR SEQ ID NO:205:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:205:

GGGAGGACGA TGCGGCTTGA CGACGGATGT AGCTACGCGT TGAGTCCACA          50

ACAGGCAGAC GACGAGCGGG A                                         71

(2) INFORMATION FOR SEQ ID NO:206:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:206:

GGGAGGACGA TGCGGGCGT TGCGTGACTC CAGTACTGGT CTATTTATCC           50

TCGTCCAGAC GACGAGCGGG A                                         71

(2) INFORMATION FOR SEQ ID NO:207:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:207:

GGGAGGACGA TGCGGCACGG TAGTGCTACC AGATGGTTAT GTTACTTCAA          50

TCTGCAGACG ACGAGCGGGA                                           70

(2) INFORMATION FOR SEQ ID NO:208:

(i) SEQUENCE CHARACTERISTICS:
        (A) LENGTH: 71 base pairs

```
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:208:

GGGAGGACGA TGCGGGGCGG GATCATGCTA CCAGTTGGTT ATCATCTACT          50

TACCCCAGAC GACGAGCGGG A                                        71

(2) INFORMATION FOR SEQ ID NO:209:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:209:

GGGAGGACGA TGCGGACGGT AGTGCTACCA GATGGTTATG TTACTTCAAT          50

TCTGCAGACG ACGAGCGGGA                                          70

(2) INFORMATION FOR SEQ ID NO:210:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:210:

GGGAGGACGA TGCGGCAGGG CGGAATTTGA GTGAGCAGTC TTAAAATGTC          50

GTCTGCAGAC GACGAGCGGG A                                        71

(2) INFORMATION FOR SEQ ID NO:211:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:211:

GGGAGGACGA TGCGGCACGG TAGTGCTACC AGATGGTTAT GTTACTTCAA          50

TTCTGCAGAC GACGAGCGGG A                                        71

(2) INFORMATION FOR SEQ ID NO:212:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:212:

GGGAGGACGA TGCGGCCTGC GTAACAACGC GGAGGAAACT TCCCTCCTAT          50

CTCTGCAGAC GACGAGCGGG A                                        71
```

151

-continued (2) INFORMATION FOR SEQ ID NO:213:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:213:

```
GGGAGGACGA TGCGGCAGGA CATGCTACCA ATCGGGTATA TCGACTTCTA         50

CTCTCCAGAC GACGAGCGGG A                                        71
```

(2) INFORMATION FOR SEQ ID NO:214:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:214:

```
GGGAGGACGA TGCGGCACCG TCATTTAGGA TTCGTCAGGC TCTACCCGTA         50

GTGTGCAGAC GACGAGCGGG A                                        71
```

(2) INFORMATION FOR SEQ ID NO:215:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:215:

```
GGGAGGACGA TGCGGTAGGA AACAGGGGTG CACGGGGAAA TCATGCTTTA         50

TCATCCAGAC GACGAGCGGG A                                        71
```

(2) INFORMATION FOR SEQ ID NO:216:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:216:

```
GGGAGGACGA TGCGGCAGGA CGACTCGTAG GCACCTAACC TAACAACTAA         50

CGCTACAGAC GACGAGCGGG A                                        71
```

(2) INFORMATION FOR SEQ ID NO:217:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:217:

GGGAGGACGA TGCGGGCCGA CGTAGTGTAC ATTTAAACCA GGGGCCTGCT       50

CTCTACAGAC GACGAGCGGG A                                     71

(2) INFORMATION FOR SEQ ID NO:218:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:218:

GGGAGGACGA TGCGGGGGGC AGATGATGTT GTTTGAACCC TAGTACTGGC       50

AGTGCCAGAC GACGAGCGGG A                                     71

(2) INFORMATION FOR SEQ ID NO:219:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:219:

GGGAGGACGA TGCGGGGGCA GAACCGACAT TTTGCCCTAC ATACGTAGCT       50

TTCCACAGAC GACGAGCGGG A                                     71

(2) INFORMATION FOR SEQ ID NO:220:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:220:

GGGAGGACGA TGCGGGGGGT CACGATTTGC GTCTCTCAGT GATTAGCATT       50

CTCGTCAGAC GACGAGCGGG A                                     71

(2) INFORMATION FOR SEQ ID NO:221:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:221:

GGGAGGACGA TGCGGCACGA CGGAATTTTT AAGTGAGCAA AGATTGTTAG       50

TGAGCAGACG ACGAGCGGGA                                       70

(2) INFORMATION FOR SEQ ID NO:222:

(i) SEQUENCE CHARACTERISTICS:
        (A) LENGTH: 70 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:222:

GGGAGGACGA TGCGGCACCT TAAGCGTACG CGGGACTTGT TACCTACTCT         50

ACTCCAGACG ACGAGCGGGA                                          70

(2) INFORMATION FOR SEQ ID NO:223:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:223:

GGGAGGACGA TGCGGCACCC GAAGATGCTA CCAATTGGTT CCAGTTTTAT         50

CCCTCCAGAC GACGAGCGGG A                                        71

(2) INFORMATION FOR SEQ ID NO:224:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:224:

GGGAGGACGA TGCGGCCACT GACGAGACAA CACTTCGGCA GGCGCACGTA         50

ACCCACAGAC GACGAGCGGG A                                        71

(2) INFORMATION FOR SEQ ID NO:225:

(i) SEQUENCE CHARACTERISTICS:
            (A) LENGTH: 37 nucleotides
            (B) TYPE: nucleic acid
            (C) STRANDEDNESS: single
            (D) TOPOLOGY: linear (ii) MOLECULE TYPE: RNA (xi) SEQUENCE DESCRIPTION: SEQ ID NO:225:

GGGUGCAUUG AGAAACACGU UUGUGGACUC UGUAUCU                       37

(2) INFORMATION FOR SEQ ID NO:226:

(i) SEQUENCE CHARACTERISTICS:
            (A) LENGTH: 29 nucleotides
            (B) TYPE: nucleic acid
            (C) STRANDEDNESS: single
            (D) TOPOLOGY: linear (ii) MOLECULE TYPE: RNA (xi) SEQUENCE DESCRIPTION: SEQ ID NO:226:

GGGGAUUAAC AGGCACACCU GUUAACCCU                                29